United States Patent
Ibrahim et al.

(10) Patent No.: US 10,717,735 B2
(45) Date of Patent: Jul. 21, 2020

(54) SOLID FORMS OF A COMPOUND FOR MODULATING KINASES

(71) Applicant: Plexxikon Inc., Berkeley, CA (US)

(72) Inventors: Prabha N. Ibrahim, Mountain View, CA (US); Hamid Rezaei, Berkeley, CA (US); Marika Nespi, Berkeley, CA (US); Ben Powell, Pleasant Hill, CA (US); Rashmin Patel, Fremont, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 16/158,107

(22) Filed: Oct. 11, 2018

(65) Prior Publication Data
US 2019/0161484 A1    May 30, 2019

Related U.S. Application Data

(60) Provisional application No. 62/572,099, filed on Oct. 13, 2017.

(51) Int. Cl.
| | |
|---|---|
| C07D 471/04 | (2006.01) |
| A61P 35/00 | (2006.01) |
| A61K 31/437 | (2006.01) |
| A61K 31/496 | (2006.01) |
| A61K 31/519 | (2006.01) |
| A61K 31/5377 | (2006.01) |
| A61K 45/06 | (2006.01) |

(52) U.S. Cl.
CPC .......... *C07D 471/04* (2013.01); *A61K 31/437* (2013.01); *A61K 31/496* (2013.01); *A61K 31/519* (2013.01); *A61K 31/5377* (2013.01); *A61K 45/06* (2013.01); *A61P 35/00* (2018.01); *C07B 2200/13* (2013.01)

(58) Field of Classification Search
CPC .. C07D 471/04; A61K 31/437; A61K 31/496; A61K 31/519; A61K 31/5377; A61K 45/06
USPC ........................................................ 546/113
See application file for complete search history.

(56) References Cited

U.S. PATENT DOCUMENTS

| | | | |
|---|---|---|---|
| 5,317,103 A | 5/1994 | Baker et al. | |
| 5,998,438 A | 12/1999 | Slassi et al. | |
| 6,358,992 B1 | 3/2002 | Pamukcu et al. | |
| 6,479,507 B2 | 11/2002 | Cheng et al. | |
| 6,906,084 B2 | 6/2005 | Nazare et al. | |
| 7,202,266 B2 | 4/2007 | Arnold et al. | |
| 7,348,338 B2 | 3/2008 | Arnold et al. | |
| 7,354,924 B2 | 4/2008 | Wang et al. | |
| 7,432,375 B2 | 10/2008 | Graczyk et al. | |
| 7,476,746 B2 | 1/2009 | Artis et al. | |
| 7,491,831 B2 | 2/2009 | Artis et al. | |
| 7,498,342 B2 | 3/2009 | Ibrahim et al. | |
| 7,504,509 B2 | 3/2009 | Ibrahim et al. | |
| 7,517,970 B2 | 4/2009 | West et al. | |
| 7,531,568 B2 | 5/2009 | Lin et al. | |
| 7,572,806 B2 | 8/2009 | Arnold et al. | |
| 7,585,859 B2 | 9/2009 | Ibrahim et al. | |
| 7,605,168 B2 | 10/2009 | Ibrahim et al. | |
| 7,696,229 B2 | 4/2010 | Dunn et al. | |
| 7,723,374 B2 | 5/2010 | Artis et al. | |
| 7,759,475 B2 | 7/2010 | West | |
| 7,846,941 B2 | 12/2010 | Zhang et al. | |
| 7,863,288 B2 | 1/2011 | Ibrahim et al. | |
| 7,863,289 B2 | 1/2011 | Spevak et al. | |
| 7,872,018 B2 | 1/2011 | Ibrahim et al. | |
| 7,893,075 B2 | 2/2011 | Zhang et al. | |
| 7,947,708 B2 | 5/2011 | Ibrahim et al. | |
| 7,956,082 B2 | 6/2011 | Kugimiya et al. | |

(Continued)

FOREIGN PATENT DOCUMENTS

| | | |
|---|---|---|
| EP | 2119703 | 11/2009 |
| WO | WO-2001/046178 | 6/2001 |

(Continued)

OTHER PUBLICATIONS

Matsumoto; Pharmaceutical Research, 1999, 16, 1722-1728. (Year: 1999).*

(Continued)

*Primary Examiner* — Daniel R Carcanague
(74) *Attorney, Agent, or Firm* — Sheppard Mullin Richter & Hampton LLP

(57) ABSTRACT

Forms of 4-(6-(3,5-dimethylisoxazol-4-yl)-1-[(1S)-1-(2-pyridyl)ethyl]pyrrolo[3,2-b]pyridin-3-yl)benzoic acid (Compound I) were prepared and characterized in the solid state:

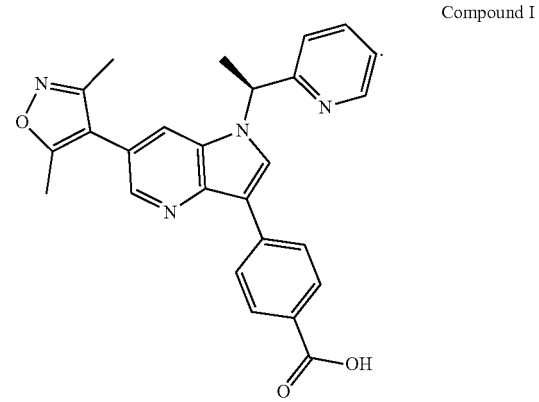

Compound I

Also provided are processes of manufacture and methods of using the forms of Compound I.

19 Claims, 24 Drawing Sheets

(56) References Cited

U.S. PATENT DOCUMENTS

| | | |
|---|---|---|
| 8,053,463 B2 | 11/2011 | Lin et al. |
| 8,067,434 B2 | 11/2011 | Ibrahim et al. |
| 8,071,581 B2 | 12/2011 | Smith et al. |
| 8,110,576 B2 | 2/2012 | Ibrahim et al. |
| 8,119,637 B2 | 2/2012 | Ibrahim et al. |
| 8,129,404 B2 | 3/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,198,273 B2 | 6/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Zhang et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,470,821 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |
| 8,865,735 B2 | 10/2014 | Diodone et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |
| 9,096,593 B2 | 8/2015 | Zhang et al. |
| 9,150,570 B2 | 10/2015 | Ibrahim et al. |
| 9,169,250 B2 | 10/2015 | Zhang et al. |
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 9,624,213 B2 | 4/2017 | Ibrahim et al. |
| 9,663,517 B2 | 5/2017 | Desai et al. |
| 9,676,748 B2 | 6/2017 | Wu et al. |
| 9,682,981 B2 | 6/2017 | Zhang et al. |
| 9,695,169 B2 | 7/2017 | Ibrahim |
| 9,718,847 B2* | 8/2017 | Zhang .................. C07D 413/04 |
| 9,730,918 B2 | 8/2017 | Bollag et al. |
| 9,745,298 B2 | 8/2017 | Ibrahim et al. |
| 9,771,363 B2 | 9/2017 | Ibrahim et al. |
| 9,771,369 B2 | 9/2017 | Lin et al. |
| 9,776,998 B2 | 10/2017 | Ibrahim et al. |
| 9,802,932 B2 | 10/2017 | Ibrahim et al. |
| 9,814,714 B2 | 11/2017 | Ibrahim et al. |
| 9,822,109 B2 | 11/2017 | Zhang et al. |
| 9,844,539 B2 | 12/2017 | Wu et al. |
| 9,856,259 B2 | 1/2018 | Shi et al. |
| 9,873,700 B2 | 1/2018 | Zhang et al. |
| 9,938,273 B2 | 4/2018 | Wu et al. |
| 1,016,075 A1 | 12/2018 | Lin et al. |
| 10,501,460 B2* | 12/2019 | Zhang .................. A61K 31/675 |
| 2004/0009983 A1 | 1/2004 | Cox et al. |
| 2004/0092569 A1 | 5/2004 | Demaine et al. |
| 2004/0142864 A1 | 7/2004 | Bremer et al. |
| 2004/0167188 A1 | 8/2004 | Xin et al. |
| 2004/0171062 A1 | 9/2004 | Hirth et al. |
| 2005/0048573 A1 | 3/2005 | Artis et al. |
| 2005/0079548 A1 | 4/2005 | Artis et al. |
| 2005/0164300 A1 | 7/2005 | Artis et al. |
| 2005/0170431 A1 | 8/2005 | Ibrahim et al. |
| 2006/0030583 A1 | 2/2006 | Arnold et al. |
| 2006/0058339 A1 | 3/2006 | Ibrahim et al. |
| 2006/0135540 A1 | 6/2006 | Lin et al. |
| 2006/0160135 A1 | 7/2006 | Wang et al. |
| 2006/0183758 A1 | 8/2006 | Beard et al. |
| 2007/0066641 A1 | 3/2007 | Ibrahim et al. |
| 2007/0072904 A1 | 3/2007 | Lin et al. |
| 2008/0171772 A1 | 7/2008 | Beard et al. |
| 2008/0221127 A1 | 9/2008 | Lin et al. |
| 2008/0234349 A1 | 9/2008 | Lin et al. |
| 2008/0249110 A1 | 10/2008 | Bonnert et al. |
| 2008/0249137 A1 | 10/2008 | Lin et al. |
| 2009/0047246 A1 | 2/2009 | Beigelman et al. |
| 2009/0069565 A1 | 3/2009 | Nazare et al. |
| 2009/0221608 A1 | 9/2009 | Cui et al. |
| 2009/0325970 A1 | 12/2009 | Yuan |
| 2010/0120739 A1 | 5/2010 | Smith et al. |
| 2010/0190777 A1 | 7/2010 | Wu et al. |
| 2011/0046370 A1 | 2/2011 | Sim et al. |
| 2011/0092538 A1 | 4/2011 | Spevak et al. |
| 2011/0112127 A1 | 5/2011 | Zhang et al. |
| 2011/0166174 A1 | 7/2011 | Ibrahim et al. |
| 2011/0183988 A1 | 7/2011 | Ibrahim et al. |
| 2011/0218198 A1 | 9/2011 | Wucherer-Plietker et al. |
| 2011/0281888 A1 | 11/2011 | Mulvihill et al. |
| 2012/0015966 A1 | 1/2012 | Lin et al. |
| 2012/0053177 A1 | 3/2012 | Ibrahim et al. |
| 2012/0122860 A1 | 5/2012 | Visor et al. |
| 2012/0165366 A1 | 6/2012 | Ibrahim et al. |
| 2012/0245174 A1 | 9/2012 | Ibrahim et al. |
| 2013/0237531 A1 | 9/2013 | Wu et al. |
| 2013/0261117 A1 | 10/2013 | Ibrahim et al. |
| 2013/0303534 A1 | 11/2013 | Ibrahim et al. |
| 2014/0038948 A1 | 2/2014 | Wu et al. |
| 2014/0128390 A1 | 5/2014 | Lin et al. |
| 2014/0303121 A1 | 10/2014 | Zhang et al. |
| 2014/0303187 A1 | 10/2014 | Wu et al. |
| 2015/0133400 A1* | 5/2015 | Zhang .................. C07D 413/14 514/63 |
| 2015/0290205 A1 | 10/2015 | Ibrahim et al. |
| 2016/0068528 A1* | 3/2016 | Zhang .................. C07F 7/0814 514/63 |
| 2016/0176865 A1 | 6/2016 | Ibrahim et al. |
| 2016/0340357 A1 | 11/2016 | Ibrahim et al. |
| 2017/0029413 A1 | 2/2017 | Holladay et al. |
| 2017/0157120 A1 | 6/2017 | Ibrahim et al. |
| 2017/0247370 A1 | 8/2017 | Zhang et al. |
| 2017/0267660 A1 | 9/2017 | Lin et al. |
| 2017/0283423 A1 | 10/2017 | Zhang et al. |
| 2017/0319559 A1 | 11/2017 | Wu et al. |
| 2017/0320899 A1 | 11/2017 | Zhang et al. |
| 2017/0334909 A1 | 11/2017 | Ibrahim et al. |
| 2017/0349572 A1 | 12/2017 | Wu et al. |
| 2017/0362231 A1 | 12/2017 | Ibrahim et al. |
| 2018/0002332 A1 | 1/2018 | Ibrahim et al. |
| 2018/0030051 A1 | 2/2018 | Ibrahim et al. |
| 2018/0055828 A1 | 3/2018 | Bollag |
| 2018/0072722 A1 | 3/2018 | Zhang et al. |
| 2018/0099939 A1 | 4/2018 | Zhang et al. |
| 2018/0099975 A1 | 4/2018 | Zhang et al. |
| 2018/0111929 A1 | 4/2018 | Ibrahim |
| 2018/0111930 A1 | 4/2018 | Desai |
| 2018/0215763 A1 | 8/2018 | Wu et al. |
| 2018/0265508 A1 | 9/2018 | Lin |
| 2018/0305358 A1 | 10/2018 | Ibrahim et al. |
| 2018/0327403 A1 | 11/2018 | Ibrahim et al. |
| 2018/0354946 A1 | 12/2018 | Zhang et al. |
| 2019/0031654 A1 | 1/2019 | Ibrahim et al. |
| 2019/0119273 A1 | 4/2019 | Ibrahim et al. |
| 2019/0125747 A1 | 5/2019 | Rezaei et al. |
| 2019/0161484 A1 | 5/2019 | Ibrahim et al. |
| 2019/0175567 A1 | 6/2019 | Wu |

FOREIGN PATENT DOCUMENTS

| | | |
|---|---|---|
| WO | WO-2003/082869 | 10/2003 |
| WO | WO-2004/014851 | 2/2004 |
| WO | WO-2004/078756 | 9/2004 |
| WO | WO-2006/015123 | 2/2006 |
| WO | WO 2007/013896 | 2/2007 |
| WO | WO-2008/051805 | 5/2008 |
| WO | WO-2008/110508 | 9/2008 |
| WO | WO-2008/155000 | 12/2008 |
| WO | WO-2009/152072 | 12/2009 |
| WO | WO-2009/155052 | 12/2009 |
| WO | WO-2010/068292 | 6/2010 |
| WO | WO 2010/111527 | 9/2010 |
| WO | WO 2010/129467 | 11/2010 |
| WO | WO-2012/069917 | 5/2012 |
| WO | WO-2012/104007 | 8/2012 |

(56) References Cited

FOREIGN PATENT DOCUMENTS

| WO | WO-2012/109075 | 8/2012 |
|---|---|---|
| WO | WO-2013/061977 | 5/2013 |
| WO | WO-2013/078254 | 5/2013 |
| WO | WO-2013/087744 | 6/2013 |
| WO | WO-2013/092463 | 6/2013 |
| WO | WO 2014/145051 | 9/2014 |
| WO | WO-2015/002754 | 1/2015 |
| WO | WO-2015/004533 | 1/2015 |
| WO | WO-2015/004534 | 1/2015 |

OTHER PUBLICATIONS

Thakral; Expert Opinion on Drug Delivery, 2013, 10, 131-149. (Year: 2013).*
U.S. Appl. No. 16/058,945, filed Aug. 8, 2018, Wu.
U.S. Appl. No. 16/123,612, filed Sep. 6, 2018, Desai et al.
U.S. Appl. No. 16/148,244, filed Oct. 1, 2018, Zhang et al.
U.S. Appl. No. 16/358,608, filed Mar. 19, 2019, filed Zhang et al.
U.S. Appl. No. 16/400,801, filed May 1, 2019, Ibrahim et al.
U.S. Appl. No. 16/441,610, filed Jun. 14, 2019, Ibrahim et al.
International Search Report and Written Opinion dated Feb. 12, 2019 for PCT/US2018/055473. 16 pages.
Newman. Basics of Amorphous and Amorphous Solid Dispersions. Seventh Street Development Group. Pharmaceutical Powder X-ray Diffraction Symposium. Feb. 22, 2010. 55 pages.
U.S. Appl. No. 16/510,617, filed Jul. 12, 2019, Ibrahim et al.
U.S. Appl. No. 16/510,764, filed Jul. 12, 2019, Ibrahim et al.
U.S. Appl. No. 16/510,757, filed Jul. 12, 2019, Ibrahim et al.
U.S. Appl. No. 16/563,656, filed Sep. 6, 2019, Zhang et al.
Alsarraj et al., "Bromodomain-Containing Protein 4: A Dynamic Regulator of Breast Cancer Metastasis through Modulation of the Extracellular Matrix", International Journal of Breast Cancer 2011, (7 pages).
Ambrosini et al., "BRD4-targeted therapy induces Myc-independent cytotoxicity in Gnaq/11-mutatant uveal melanoma cells", Oncotarget, 2015, vol. 6, No. 32, pp. 33397-33409.
Argollo, "Novel therapeutic targets for inflammatory bowel disease", Journal of Autoimmunity (2017), 85, 103-116.
Asangani et al., "Therapeutic targeting of BET bromodomain proteins in castration-resistant prostate cancer", Nature, 2014, vol. 510, pp. 278-282.
Babu "Emerging therapeutic strategies in COPD" Drug Discovery Today 2015 vol. 20, pp. 371-379.
Bandukwala et al., "Selective inhibition of CD4+ T-cell cytokine production and autoimmunity by BET protein and c-Myc inhibitors", PNAS 2012, vol. 109. No. 36, pp. 14532-14537.
Banker et al., "Modern Pharmacuetics, 3ed.," Marcel Dekker, New York, (1996), pp. 451 and 596.
Beaumont, "Design of Ester Prod rugs to Enhance Oral Absorption of Poorly Permeable Compounds: Challenges to the Discovery Scientist" Current Drug Metabolism, 2003, 4, 461-485.
Bendele, "Animal Models of Arthritis: Relevance to Human Disease" Toxicol Pathol 1999 27: 134-142.
Bendele, "Animal models of rheumatoid arthritis" J Musculoskel Neuron Interact 2001; 1(4):377-385.
Bobko et al., "Synthesis of 2,5-disubstituted-3-cyanoindoles," Tetrahedron Lett., 53(2): 200-202 (2011).
Boniface, "Multidisciplinary management for esophageal and gastric cancer", Cancer Management and Research, 2016:8 39-44.
Cain, "Bromodomain brake on AML", SciBX, 4(31); doi:10.1038/scibx.2011.867, Aug. 11, 2011, https://www.nature.com/scibx/journal/v4/n31/full/scibx.2011.867.html.
Chaidos et al., "Potent antimyeloma activity of the novel bromodomain inhibitors I-BET151 and I-BET762", Blood, 2014, 123, 5, pp. 697-705.
Cheung et al., "BET N-terminal bromodomain inhibition selectively blocks Th17 cell differentiation and ameliorates colitis in mice", PNAS, 2017, vol. 114, No. 11, pp. 2952-2957.
Cornish et al., "G-CSF and GM-CSF as therapeutic targets in rheumatoid arthritis", Nat. Rev. Rheumatol 2009, vol. 5, pp. 554-559.
Crawford et al., "Bromodomain 4 activation predicts breast cancer survival", PNAS, 2008, pp. 6380-6385.
Damia "Contemporary pre-clinical development of anticancer agents—What are the optimal preclinical models?" European Journal of Cancer 2009, 45, 2768-2781.
Database accession No. 7647302, 7665443 (XRNs) abstract & Chem. Pharm. Bull., 44(10): 1831-1839 (1996).
Database accession No. 8234793, 8235134 (XRNs) abstract & Zeitschrift Fur Naturforschung—Section B Journal of Chemical Sciences, 53(10): 1216-1222 (1998).
Estey, "New drug approvals in acute myeloid leukemia: what's the best end point?", Leukemia (2016), 30, 521-525.
Ex parte Ankush Argade et al., Appeal 2013-008708, U.S. Appl. No. 12/030,069 dated Aug. 12, 2016, (25 pages).
Ex parte Marin Gleave et al., Appeal 2012-009281, U.S. Appl. No. 12/845,521 dated Jan. 29, 2014, (9 pages).
Filippakopoulos et al., Selective inhibition of BET bromodomains, Nature 2010, vol. 468, pp. 1067-1073.
French, "Small-Molecule Targeting of BET Proteins in Cancer", Advances in Cancer Research, 2016, vol. 131, pp. 21-58.
Furdas et al., "Inhibition of bromodomain-mediated protein-protein interactions as a novel therapeutic strategy", 3(2): 123-134 (2012).
Garson, "Models of ovarian cancer—Are we there yet?", Molecular and Cellular Endocrinology 239 (2005) 15-26.
Gerratana, "Do platinum salts fit all triple negative breast cancers?", Cancer Treatment Reviews, 48, (2016) 34-41.
Hay et al., "The design and synthesis of 5- and 6-isoxazolylbenzimidazoles as selective inhibitors of the BET bromodomains," Medchemcomm, 4(1): 140-144 (2012).
Hay, "Discovery and Optimization of Small-Molecule Ligands for the CBP/p300 Bromodomains," J. Am. Chem. Soc., (2014), 136:9308-9319.
Heinemann et al., "Combining BET and HDAC inhibitors synergistically induces apoptosis of melanoma and suppresses AKT and YAP signaling", Oncotarget, 2015, vol. 6, No. 25, pp. 21507-21521.
Henssen et al., "BET bromodomain protein inhibition is a therapeutic option for medulloblastoma", Oncotarget, 2013, vol. 4, No. 11, pp. 2080-2095.
Henze et al., "The Number of Structurally Isomeric Alcohols of the Methanol Series" Journal of the American Chemical Society 1931, 3042.
Hewings et al., "3,5-Dimethylisoxazoles Act As Acetyl-lysine-mimetic Bromodomain Ligands," J. Med. Chem., 54(19): 6761-6770 (2011).
Hogg et al., "BET inhibition Induces Apoptosis in Aggressive B-Cell Lymphoma via Epigenetic Regulation of BCL-2 Family Members", Mol. Cancer Ther., 2016, 15(9), pp. 2030-2041.
Hohmann et al., "Sensitivity and engineered resistance of myeloid leukemia cells to BRD9 inhibition", Nature Chemical Biology, 2016, 12, pp. 672-679.
Howington, "Treatment of Stage I and II Non-small Cell Lung Cancer Diagnosis and Management of Lung Cancer, 3rd ed: American College of Chest Physicians Evidence-Based Clinical Practice Guidelines" CHEST 2013; 143(5)(Suppl):e278S-e313S.
Hu et al., "BRD4 Inhibitor Inhibits Colorectal Cancer Growth and Metastasis", Int. J. Mol. Sci., 2015, 16, pp. 1928-1948.
International Preliminary Report on Patentability for International Application No. PCT/US2014/029701 dated Sep. 15, 2015. (13 pages).
International Search Report for PCT/US2014/029701 dated Jul. 8, 2014, 13 pages.
Jett, "Treatment of Small Cell Lung Cancer Diagnosis and Management of Lung Cancer", 3rd ed: American College of Chest Physicians Evidence-Based Clinical Practice Guidelines, CHEST 2013; 143(5)(Suppl):e400S-e419S.
Johnson et. al. "Relationships between drug activity in NCI preclinical in vitro and in vivo models and early clinical trials", British Journal of Cancer 2001, 84, 1424-1431.
Jung et al., "Targeting BET bromodomains for cancer treatment", Epigenomics, 2015, 7(3), pp. 487-501.

(56) References Cited

OTHER PUBLICATIONS

Khan et al., "Brd4 is Essential for IL-1β-Induced Inflammation in Human Airway Epithelial Cells", PLOS One, 2014, vol. 9, Issue 4, e95051, pp. 1-17.

Kharenko et al., "RVX-297—a novel BD2 selective inhibitor of BET bromodomains", Biochemical and Biophysical Research Communications, 2016, 477, pp. 62-67.

Klingbeil et al., "Inhibition of BET bromodomain-dependent XIAP and FLIP expression sensitizes KRAS-mutated NSCLC to pro-apoptotic agents", Cell Death and Disease, 2016, 7, e2365, pp. 1-13. doi: 10.1038/cddis.2016.271.

Kottenhahn, "The ferric chloride oxidation of 5-substituted o-semidines and the polarographic properties of the products." Journal of Organic Chemistry 1963 28(11), 3114-20.

Krishnan, "Multiple myeloma and persistence of drug resistance in the age of novel drugs (Review)", International Journal of Oncology 49: 33-50, 2016.

Kurimchak et al., "Resistance to BET Bromodomain Inhibitors is Mediated by Kinome Reprogramming in Ovarian Cancer", Cell Reports, 2016, 16, pp. 1273-1286.

Larsson et al., "BET Bromodomain Inhibition Reduces Leukemic Burden and Prolongs Survival in the Eμ-TCL1 Transgenic Mouse Model of Chronic Lymphocytic Leukemia (CLL) Independent of TP53 Mutation Status", Blood 2013, 122:876; http://www.bloodjournal.org/content/122/21/876?sso-checked=true.

Ledford, "US cancer institute overhauls cell lines" Nature Feb. 25, 2016 vol. 530, p. 391.

Lee et al., "Nonselective inhibition of the epigenetic transcriptional regulator BET induces marked lymphoid and hematopoietic toxicity in mice", Toxicology and Applied Pharmacology, 2016, 300, pp. 47-54.

Lee et al., "Synergistic Effect of JQ1 and Rapamycin for Treatment of Human Osteosarcoma", Int. J. Cancer, 2015, 136, pp. 2055-2064.

Lockwood et al., "Sensitivity of human lung adenocarcinoma cell lines to targeted inhibition of BET epigenetic signaling proteins", PNAS, 2012, 109(47), pp. 19408-19413.

Loven et al., "Selective Inhibition of Tumor Oncogenes by Disruption of Super-Enhancers", Cell, 2013, 153, pp. 320-334.

Lu et al., "Hijacking the E3 Ubiquitin Ligase Cereblon to Efficiently Target BRD4", Chemistry & Biology, 2015, 22, pp. 755-763.

Mirguet et al., "From ApoA1 upregulation to BET family bromodomain inhibition: Discovery of I-BET151," Bioorg.Med. Chem. Lett., 22(8):2963-2967 (2012).

Montenegro et al., "BET inhibition as a new strategy for the treatment of gastric cancer", Oncotarget, 2016, 7(28), pp. 43997-44012.

Muller et al., "Bromodomains as therapeutic targets", doi:10.1017/S1462399411001992; vol. 13; e29; Sep. 2011, https://www.ncbi.nlm.nih.gov/pmc/articles/PMC3177561/pdf/S1462399411001992a.pdf.

Nicodeme et al., "Suppression of inflammation by a synthetic histone mimic", Nature, 2010, 468(7327):1119-1123, (13 pages).

Ocana, "Preclinical development of molecular targeted agents for cancer", Nat. Rev. Clin. Oneal., 2011, 8, 200-209.

Ott et al., "BET bromodomain inhibition targets both c-Myc and IL7R in high-risk acute lymphyoblastic leukemia", Blood, 2012, 120(14), pp. 2843-2852.

Ozer et al., "BRD4 Profiling Identifies Critical Chronic Lymphocytic Leukemia Oncogenic Circuits and Reveals Sensitivity to PLX51107, a Novel Structurally Distinct BET Inhibitor", Cancer Discovery 2018, pp. 458-477.

Papavassiliou et al., "Bromodomains: pockets with therapeutic potential", Trends in Molecular Medicine, 2014, vol. 20, No. 9, pp. 477-478.

Park-Min et al., "Inhibition of osteoclastogenesis and inflammatory bone resorption by targeting BET proteins and epigenetic regulation", Nature Communications, 2014, 5:5418, pp. 1-9.

Pastori et al., "The Bromodomain protein BRD4 controls HOTAIR, a long noncoding RNA essential for glioblastoma proliferation", PNAS, 2015, 112(27), pp. 8326-8331.

Patel et al., "BET Bromodomain Inhibition Triggers Apoptosis of NF1-Associated Malignant Peripheral Nerve Sheath Tumors through Bim Induction", Cell Reports, 2014, 6, pp. 81-92.

Patnaik et al., "Phase ib/2a study of PLX51107, a small molecule BET inhibitor, in subjects with advanced hematological malignancies and solid tumors", Journal of Clinical Oncology, 2018, 36, No. 15, Supplement 2550, (4 pages).

Pérez-Salvia et al., "Bromodomain inhibitors and cancer therapy: From structures to applications", Epigenetics, 2017, vol. 12, No. 5, pp. 323-339.

Pui, "Treatment of Acute Lymphoblastic Leukemia", New England Journal of Medicine, 2006, 354, 166-78.

Rautio et. al. "Prodrugs: design and clinical Applications", Nature Reviews Drug Discovery, 2008, 7, 255-270.

Rhyasen et al., "AZD5153: A Novel Bivalent BET Bromodomain Inhibitor Highly Active against Hematologic Malignancies", Mol Cancer Ther, 2016, 15(11), pp. 2563-2574.

Sale "Models of ovarian cancer metastasis: Murine models" Drug Discovery Today: Disease Models, 2006, 3, 150-154.

Sanz-Garcia, "Current and advancing treatments for metastatic colorectal cancer", Expert Opinion on Biological Therapy, 16:1, 2016, 93-110.

Schober, "New Advances in the Treatment of Metastatic Pancreatic Cancer", Digestion, 2015;92: 175-184.

Scribner et al., "Synthesis and biological activity of anticoccidial agents: 2,3-diarylindoles," Biorg. Med. Chem. Lett., 19(5): 1517-1521 (2009).

Segura et al., "Abstract 2185: BRD4 is a novel therapeutic target in melanoma", Cancer Research, 2012, (3 pages).

Sengupta et al., "Disruption of BRD4 at H3K27 Ac-enriched enhancer region correlates with decreased c-Myc expression in Merkel cell carcinoma", Epigenetics, 2015, 10(6), pp. 460-466.

Sharma, "Cell line-based platforms to evaluate the therapeutic efficacy of candidate anticancer agents", Nature Reviews Cancer, Apr. 2010, vol. 10, 241-253.

Shi et al., "Disrupting the Interaction of BRD4 with Diacetylated Twist Suppresses Tumorigenesis in Basal-like Breast Cancer", Cancer Cell, 2014, 25, pp. 210-225.

Simone, Oncology: Introduction, Cecil Textbook of Medicine, 20th Edition, 1996 vol. 1, pp. 1004-1010.

Socinski, "Treatment of Stage IV Non-small Cell Lung Cancer Diagnosis and Management of Lung Cancer, 3rd ed: American College of Chest Physicians Evidence-Based Clinical Practice Guideline" CHEST 2013; 143(5)(Suppl):e341S-e368S.

Solanki, "Evolving targets for the treatment of atherosclerosis" Pharmacology & Therapeutics (2018), Online: "https://doi. org/10.1016/j .pharmthera.2018.02.002".

Stewart, "Novel therapeutics in multiple myeloma", Hematology 2012, 17(S1), s105-s108.

Vardiman, "The World Health Organization (WHO) classification of the myeloid neoplasms", Blood (2002), 100(7), 2292-2302.

Wolff, "Burger's Medicinal Chemistry, Sed Part I," John Wiley & Sons, (1995), pp. 975-977.

Wu et al., "Phospho Switch Triggers Brd4 Chromatin Binding and Activator Recruitment for Gene-Specific Targeting", Molecular Cell, 2013, 49, pp. 843-857.

Wyce et al., "BET Inhibition Silences Expression of MYCN and BCL2 and Induces Cytotoxicity in Neuroblastoma Tumor Models", PLOS One, 2013, vol. 8, Issue 8, e72967, (16 pages).

Wyce et al., "Inhibition of BET bromodomain proteins as a therapeutic approach in prostate cancer", Oncotarget, 2013, vol. 4, No. 12. pp. 2419-2429.

Yoo, "New drugs in prostate cancer", Prostate Int, 4 (2016) 37-42.

Zhang et al., "RAF inhibitors that evade paradoxical MAPK pathway activation", Nature 2015, vol. 526. (16 pages).

* cited by examiner

SOLID FORMS OF A COMPOUND FOR MODULATING KINASES

CROSS-REFERENCE TO RELATED PATENT APPLICATIONS

This application claims the benefit under 35 U.S.C. § 119(e) of U.S. Provisional Application 62/572,099, filed Oct. 13, 2017, which is hereby incorporated by reference in its entirety.

FIELD

The present disclosure relates generally to solid forms of compounds that modulate or inhibit the activity of bromodomain proteins, pharmaceutical compositions thereof, therapeutic uses thereof, and processes for making the solid forms. The present disclosure also provides embodiments directed to methods of treating myelodysplastic syndromes (MDS) or acute myeloid leukemia (AML) in a subject in need thereof by administering to the subject an effective amount of any one of the solid forms of Compound I in combination with an effective amount of a hypomethylating agent (HMA).

BACKGROUND

There remains a need to develop effective treatments for subjects suffering from or at risk of protein kinase mediated disease or condition. Suitable compounds, including Compound I, for the treatment of such diseases and conditions are disclosed in U.S. Patent Publication No. 2015/0133400, the disclosure of which is hereby incorporated by reference in its entirety.

There also remains a need for high purity solid forms of Compound I that are efficacious for the treatment of diseases modulated by bromodomain proteins.

SUMMARY

The present disclosure provides solid forms of Compound I of the formula:

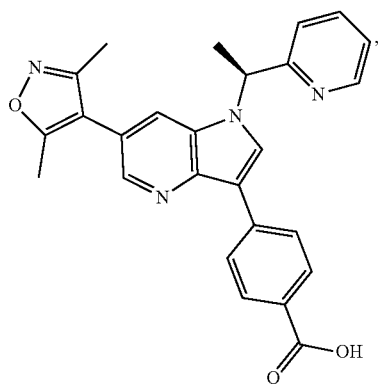

I and salts, co-crystals, solvates, and hydrates thereof. Also described herein are processes for making the forms of Compound I, pharmaceutical compositions comprising solid forms of Compound I, and methods for using such forms and pharmaceutical compositions in the treatment of diseases mediated by bromodomain proteins.

Accordingly, the present disclosure provides, in one embodiment, a free acid amorphous form of Compound I.

In some embodiments, the free acid amorphous form of Compound I is characterized by an X-ray powder diffractogram as substantially shown in FIG. 18.

In some embodiments, the free acid amorphous form of Compound I is characterized by a thermogravimetric analysis (TGA) thermogram showing a weight loss of about 17% up to about 250° C. In some embodiments, the free acid amorphous form of Compound I is characterized by the TGA thermogram as substantially shown in FIG. 19.

In some embodiments, the free acid amorphous form of Compound I is characterized by a differential scanning calorimetry (DSC) curve that comprises an exotherm with a peak maximum at about 237° C. In some embodiments, the free acid amorphous form of Compound I according to claim 5 characterized by the DSC curve as substantially shown in FIG. 20.

In some embodiments, the free acid amorphous form of Compound I is a free acid amorphous salt form of Compound I molecularly dispersed in polymer matrix. In some embodiments, the polymer matrix comprises hypromellose acetate succinate, hydroxypropyl methylcellulose phthalate, Eudragit®, or combinations thereof.

The present disclosure provides, in one embodiment, a crystalline form of Compound I.

In some embodiments, the crystalline form of Compound I is Compound I Form A characterized by an X-ray powder diffractogram comprising peaks (±0.2°) at 17.1, 19.4, and 23.5°2θ as determined on a diffractometer using Cu-Kα radiation. In some embodiments, Compound I Form A is further characterized by one or more of the following:
  i) one or more peaks at 6.7, 9.7, 10.3, 12.1, 12.5, 15.8, 19.0, and 21.4°2θ±0.2°; and
  ii) a differential scanning calorimetry (DSC) thermogram comprising an endotherm with a peak maximum at about 238.0° C.

In some embodiments, the crystalline form of Compound I is Compound I Form B characterized by an X-ray powder diffractogram comprising peaks (±0.2°) at 16.8, 17.4, and 21.1°2θ±0.2°2θ as determined on a diffractometer using Cu-Kα radiation. In some embodiments, Compound I Form B is further characterized by one or more of the following:
  i) one or more peaks at 13.7, 14.0, 14.2, 15.7, 19.7, 22.4, 23.2, and 24.6°2θ±0.2°; and
  ii) a differential scanning calorimetry (DSC) thermogram comprising an endotherm with a peak maximum at about 277° C.

In some embodiments, the crystalline form of Compound I is Compound I Form C characterized by an X-ray powder diffractogram comprising peaks (±0.2°) at 13.7, 14.6, and 22.6°2θ as determined on a diffractometer using Cu-Kα radiation. In some embodiments, Compound I Form C is further characterized by one or more of the following:
  i) one or more peaks at 10.0, 11.2, 12.4, 13.7, 14.6, 15.6, 18.6, 20.2, 21.3, 21.9, 22.6, and 23.8°2θ±0.2°; and
  ii) a differential scanning calorimetry (DSC) thermogram comprising an endotherm with a peak maximum at about 235° C.

In some embodiments, the crystalline form of Compound I is Compound I Form D characterized by an X-ray powder diffractogram comprising peaks (±0.2°) at 3.5, 18.0, and 19.1°2θ as determined on a diffractometer using Cu-Kα radiation. In some embodiments, Compound I Form D is further characterized by one or more of the following:
  i) peaks at 7.0, 10.8, 11.4, 13.1, 15.5, 17.4, 17.5, 18.5, 19.7, and 21.2°2θ±0.2°; and ii) a differential scanning calorimetry (DSC) thermogram comprising an endotherm with a peak maximum at about 235.0° C.

The present disclosure provides, in one embodiment, a pharmaceutical composition comprising one or more pharmaceutically acceptable carriers, and a free acid amorphous form of Compound I as described herein.

The present disclosure provides, in one embodiment, a pharmaceutical composition comprising one or more pharmaceutically acceptable carriers, and one or more compounds selected from Compound I Form A, Compound I Form B, Compound I Form C, and Compound I Form D as described herein.

The present disclosure provides, in one embodiment, a method for modulating bromodomain in a subject in need thereof, the method comprising administering to the subject an effective amount of a free acid amorphous form of Compound I as described herein.

The present disclosure provides, in one embodiment, a method for treating a subject suffering from, or at risk of, a disease or condition mediated by a bromodomain, the method comprising administering to the subject in need thereof an effective amount of: a free acid amorphous form of Compound I as described herein.

In some embodiments, the disease or condition treated by the methods described herein is a cancer, a neurological condition, an autoimmune condition, an inflammatory condition, a metabolic disease, or combinations thereof. In some embodiment, the disease or condition is rheumatoid arthritis, uveal melanoma, chronic lymphocytic leukemia, acute myeloid leukemia, synovial sarcoma, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes, or acute rejection of transplanted organs.

The present disclosure provides, in one embodiment, a method for treating a subject suffering from, or at risk of, a disease or condition mediated by a bromodomain, the method comprising administering to the subject in need thereof an effective amount of a free acid amorphous form of Compound I as described herein, wherein the disease or condition is rheumatoid arthritis, uveal melanoma, chronic lymphocytic leukemia, acute myeloid leukemia, synovial sarcoma, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes, or acute rejection of transplanted organs.

The present disclosure provides, in one embodiment, a method of treating chronic lymphocytic leukemia (CLL) or Richter's Syndrome in a subject in need thereof by administering to the subject an effective amount of a free acid amorphous form of Compound I as described herein. In one embodiment, the subject is also optionally administered a Bruton's Tyrosine Kinase (BTK) inhibitor. In one embodiment, the BTK inhibitor is ibrutinib.

The present disclosure provides, in one embodiment, a method of treating myelodysplastic syndromes (MDS) or acute myeloid leukemia (AML) in a subject in need thereof by administering to the subject an effective amount of a free acid amorphous form of Compound I as described herein, in combination with an effective amount of a hypomethylating agent (HMA).

The present disclosure provides, in one embodiment, a method of treating chronic lymphocytic leukemia (CLL) or Richter's Syndrome in a subject in need thereof by administering to the subject an effective amount of a free acid amorphous form of Compound I as described herein, in combination with an effective amount of a Bruton's Tyrosine Kinase (BTK) inhibitor. In one embodiment, the BTK inhibitor is ibrutinib.

The present disclosure provides, in one embodiment, a method of treating chronic lymphocytic leukemia (CLL) in a subject in need thereof by administering to the subject an effective amount of a free acid amorphous form of Compound I as described herein, in combination with an effective amount of a B-cell lymphoma 2 (BCL-2) inhibitor.

The present disclosure provides, in one embodiment, a method of treating chronic lymphocytic leukemia (CLL) in a subject in need thereof by administering to the subject an effective amount of a free acid amorphous form of Compound I as described herein, in combination with an effective amount of a phosphatidylinositol-4,5-bisphosphate 3-kinase (PI3K) inhibitor.

The present disclosure provides, in one embodiment, a method of treating uveal melanoma in a subject in need thereof by administering to the subject an effective amount of a free acid amorphous form of Compound I as described herein, in combination with an effective amount of a CTLA-4 inhibitor or a checkpoint inhibitor.

The present disclosure provides, in one embodiment, a method of treating acute myeloid leukemia in a subject in need thereof by administering to the subject an effective amount of a free acid amorphous form of Compound I as described herein, in combination with an effective amount of quizartinib.

BRIEF DESCRIPTION OF THE DRAWINGS

FIG. 24 panels A-C illustrate data related to the pharmacodynamic evaluation of antitumor effects of Compound I Free Acid Amorphous in Eµ-TCL1 with advanced leukemia. Mice were stratified according to leukemic peripheral blood lymphocytes (PBLs) and spleen palpation score to receive either vehicle or Compound I Free Acid Amorphous (20 mg/kg, qd, oral gavage) for 8 days. Compound I Free Acid Amorphous reduced leukemic cells in systemic circulation (FIG. 24A) and locally in spleen (FIG. 24B), where the red line in FIGS. 24A-24B represents average values.

FIG. 24 panels D-G: using an adaptive transfer model of Eµ-TCL1, recipient wild type mice were randomized to receive vehicle (n=12) or Compound I Free Acid Amorphous (20 mg/kg, qd, oral gavage, n=10) at leukemia onset and disease progression was measured by flow cytometry as % CD19/CD5/CD45 positive PBL. Treatment was ended at 150 days.

DETAILED DESCRIPTION

Figure 1:
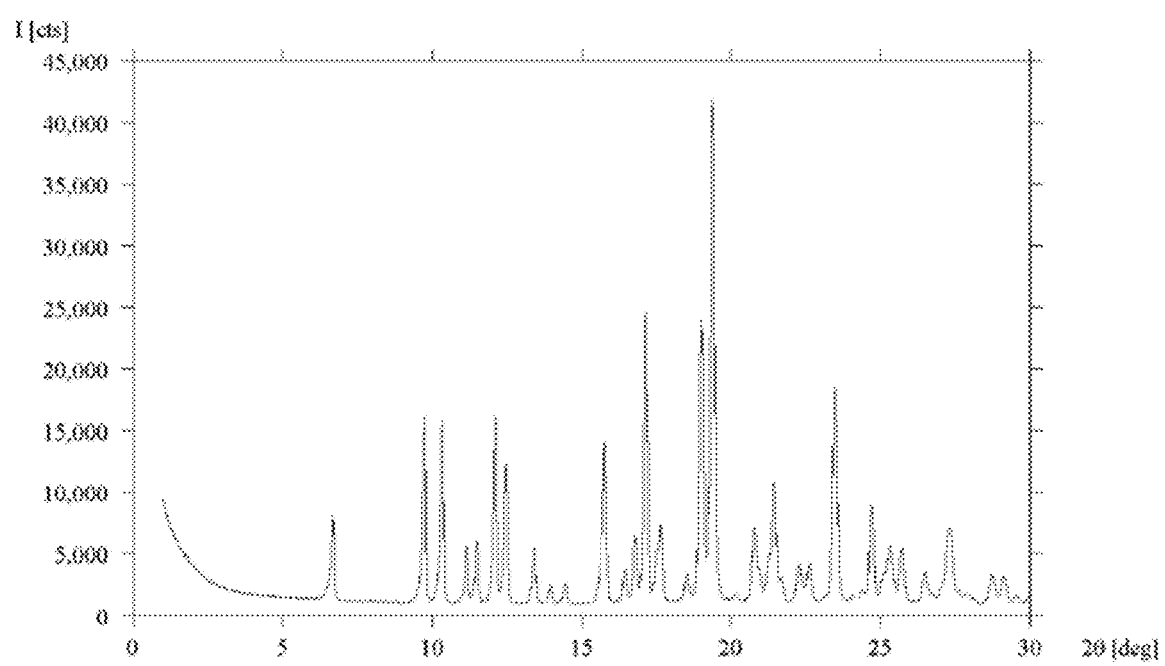
FIG. 1 is an X-ray powder diffractogram of Compound I Form A.

The compound 4-(6-(3,5-dimethylisoxazol-4-yl)-1-[(1S)-1-(2-pyridyl)ethyl]pyrrolo[3,2-b]pyridin-3-yl) benzoic acid, designated herein as Compound I or Compound I (free acid), has the following formula:

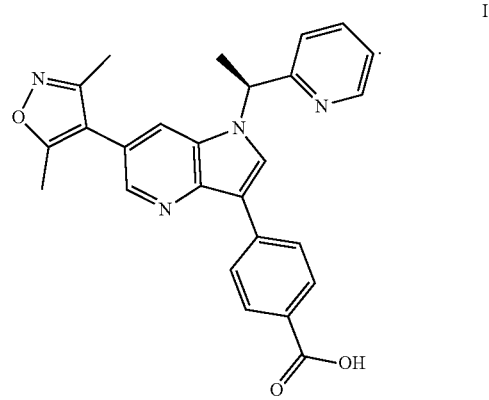 [SMILES: Cc1noc(C)c1-c1cnc2c(-c3ccc(C(=O)O)cc3)cn([C@@H](C)c3ccccn3)c2c1]

Compound I is an inhibitor or modulator of bromodomain proteins. The synthesis and method of use thereof is described in U.S. Patent Publication No. 2015/0133400, which is herein incorporated by reference in its entirety.

The present disclosure relates to various solid forms of Compound I and processes for making such solid forms.

Additional solid forms of Compound I are also described herein, as well as the processes of making such forms. For instance, in some embodiments, solid forms of Compound I may include salts or co-crystals of Compound I. In some embodiments, solid forms of Compound I may include an amorphous form of Compound I.

1. Definitions

As used in the present specification, the following words and phrases are generally intended to have the meanings as set forth below, except to the extent that the context in which they are used indicates otherwise.

The term "comprise" and variations thereof, such as, "comprises" and "comprising" are to be construed in an open, inclusive sense, that is, as "including, but not limited to." Further, the singular forms "a," "an," and "the" include plural references unless the context clearly dictates otherwise. Thus, reference to "the compound" includes a plurality of such compounds, and reference to "the assay" includes reference to one or more assays and equivalents thereof known to those skilled in the art.

Reference to "about" a value or parameter herein includes (and describes) embodiments that are directed to that value or parameter per se. In some embodiments, the term "about" includes the indicated amount ±10%. In some embodiments, the term "about" includes the indicated amount ±5%. In some other embodiments, the term "about" includes the indicated amount ±1%. Also, the term "about X" includes description of "X".

In some embodiments, the term "about," when applied to a thermogravimetric analysis (TGA) thermogram, includes a variation of ±2% in weight loss. In some embodiments, the term "about," when applied to a differential scanning calorimetry (DSC) curve, includes a variation of ±3° C.

In some embodiments, the phrase "substantially as shown in Figure" as applied to DSC curves is meant to include a variation of ±3° Celsius, and as applied to TGA thermograms is meant to include a variation of ±2% in weight loss.

Recitation of numeric ranges of values throughout the disclosure is intended to serve as a shorthand notation of referring individually to each separate value falling within the range inclusive of the values defining the range, and each separate value is incorporated in the specification as it were individually recited herein.

Forms of Compound I or salts, co-crystals, solvates, or hydrates thereof are provided herein. In one embodiment, reference to a form of Compound I or a salt, co-crystal, solvate, or hydrate thereof means that at least 50% to 99% (e.g., at least 50%, at least 55%, at least 60%, at least 65%, at least 70%, at least 75%, at least 80%, at least 85%, at least 90%, at least 95%, or at least 99%) of Compound I or a salt, co-crystal, solvate, or hydrate thereof present in a composition is in the designated form. For instance, in one embodiment, reference to Compound I Form A means that at least 50%, at least 55%, at least 60%, at least 65%, at least 70%, at least 75%, at least 80%, at least 85%, at least 90%, at least 95%, or at least 99% of Compound I present in a composition is in Form A. Reference to Compound I Free Acid Amorphous means that at least 50%, at least 55%, at least 60%, at least 65%, at least 70%, at least 75%, at least 80%, at least 85%, at least 90%, at least 95%, or at least 99% of Compound I present in a composition is in the free acid amorphous form as described herein.

The term "solid form" refers to a type of solid-state material that includes amorphous as well as crystalline forms. The term "crystalline form" refers to polymorphs as well as solvates, hydrates, etc. The term "polymorph" refers to a particular crystal structure having particular physical properties such as X-ray diffraction, melting point, and the like.

The term "co-crystal" refers to a molecular complex of a compound disclosed herein and one or more non-ionized co-crystal formers connected via non-covalent interactions. In some embodiments, the co-crystals disclosed herein may include a non-ionized form of Compound I (e.g., Compound I free acid) and one or more non-ionized co-crystal formers, where non-ionized Compound I and the co-crystal former(s) are connected through non-covalent interactions. In some embodiments, co-crystals disclosed herein may include an ionized form of Compound I (e.g., a salt of Compound I) and one or more non-ionized co-crystals formers, where ionized Compound I and the co-crystal former(s) are connected through non-covalent interactions. Co-crystals may additionally be present in anhydrous, solvated or hydrated forms. In some embodiments, co-crystals may have improved properties as compared to the parent form (i.e., the free molecule, zwitterion, etc.) or a salt of the parent compound. Improved properties can be increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like. Methods for making and characterizing co-crystals are known to those of skill in the art.

The term "co-crystal former" or "co-former" refers to one or more pharmaceutically acceptable bases or pharmaceutically acceptable acids disclosed herein in association with Compound I, or any other compound disclosed herein.

The term "solvate" refers to a complex formed by combination of solvent molecules with molecules or ions of the solute. The solvent can be an organic compound, an inorganic compound, or a mixture of both. As used herein, the term "solvate" includes a hydrate (i.e., a complex formed by combination of water molecules with molecules or ions of the solute), hemi-hydrate, channel hydrate, etc. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure.

The term "desolvated" refers to a Compound I form that is a solvate as described herein, and from which solvent molecules have been partially or completely removed. Desolvation techniques to produce desolvated forms include, without limitation, exposure of a Compound I form (solvate) to a vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially solvated wherein solvent molecules are present in stoichiometric or non-stoichiometric amounts.

The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order (glass transition).

The term "solid dispersion" refers to any solid composition having at least two components. In certain embodiments, a solid dispersion as disclosed herein includes an active ingredient (for example Compound I, or a solid or amorphous form of Compound I); preferably dispersed among at least one other component, for example a polymer. In certain embodiments, a solid dispersion as disclosed herein is a pharmaceutical dispersion that includes at least one pharmaceutically or biologically active ingredient (for example Compound I, or a solid or amorphous form of Compound I). In some embodiments, a solid dispersion includes Compound I molecularly dispersed with a polymer. In some embodiments, a solid dispersion includes a free acid amorphous form of Compound I, as disclosed herein, molecularly dispersed with a polymer. In some embodiments, a solid dispersion includes a free acid amorphous salt form of Compound I, as described herein, molecularly dispersed with a polymer. In some embodiments, the solid dispersion exists as a one phase system.

The term "molecularly dispersed", as used herein, refers to the random distribution of a compound (e.g., Compound I, a solid or amorphous form of Compound I) with a polymer. In certain embodiments the compound is present in the polymer in a final state of subdivision. See, e.g., M. G. Vachon et al., J. Microencapsulation, 14:281-301 (1997) and Vandelli et al., J. Microencapsulation, 10: 55-65 (1993). In some embodiments, a compound (for example, Compound I) may be dispersed within a matrix formed by the polymer in its solid state such that the compound is immobilized in its amorphous form. Whether a compound is molecularly dispersed in a polymer may be evidenced in a variety of ways, e.g., by the resulting solid molecular complex having a single glass transition temperature.

The term "immobilize", as used herein with reference to the immobilization of the active compound in the polymer matrix, means that molecules of the compound interact with molecules of the polymer in such a way that the molecules of the compound are held in the aforementioned matrix and prevented from crystal nucleation due to lack of mobility. In some embodiments the polymer may prevent intermolecular hydrogen bonding or weak dispersion forces between two or more drug molecules of Compound I. See, for example, Matsumoro and Zografi, Pharmaceutical Research, Vo. 16, No. 11, p 1722-1728, 1999.

Any formula or structure given herein, including Compound I, is also intended to represent unlabeled forms as well as isotopically labeled forms of the compounds. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1H$, $^2H$, $^3H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$; and the like.

As used herein, the terms "treat," "treating," "therapy," "therapies," and like terms refer to the administration of material, e.g., any one or more solid or amorphous forms of Compound I as described herein in an amount effective to prevent, alleviate, or ameliorate one or more symptoms of a disease or condition, e.g., indication, and/or to prolong the survival of the subject being treated.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

As used herein, the term "protein kinase mediated disease or condition," refers to a disease or condition in which the biological function of a protein kinase, including any mutations thereof, affects the development, course, and/or symptoms of the disease or condition, and/or in which modulation of the protein kinase alters the development, course, and/or symptoms of the disease or condition. The protein kinase mediated disease or condition includes a disease or condition for which inhibition provides a therapeutic benefit, e.g. wherein treatment with protein kinase inhibitor(s), including one or more solid or amorphous forms of Compound I as described herein, provides a therapeutic benefit to the subject suffering from or at risk of the disease or condition.

As used herein, the term "composition" refers to a pharmaceutical preparation suitable for administration to an intended subject for therapeutic purposes that contains at least one pharmaceutically active compound, including any solid or amorphous form thereof. The composition may include at least one pharmaceutically acceptable component to provide an improved formulation of the compound, such as a suitable carrier or excipient.

Other embodiments of this disclosure include compositions of any of the crystalline or amorphous forms of Compound I in combination with nanoparticles (such as naturally-equipped nanocarriers, for example, exosomes) and the like. It is known that exosomes can be highly effective drug carriers, and there are various ways in which drugs can be loaded into exosomes, including those techniques described in J Control Release, 2015 Dec. 10; 219: 396-405, the contents of which are incorporated by reference in its entirety.

As used herein, the term "subject" or "patient" refers to a living organism that is treated with compounds as described herein, including, but not limited to, any mammal, such as a human, other primates, sports animals, animals of commercial interest such as cattle, farm animals such as horses, or pets such as dogs and cats.

The term "pharmaceutically acceptable" indicates that the indicated material does not have properties that would cause a reasonably prudent medical practitioner to avoid administration of the material to a subject, taking into consideration the disease or conditions to be treated and the respective route of administration. For example, it is commonly required that such a material be essentially sterile, e.g., for injectables.

The term "pharmaceutically acceptable salt" refers to a salt which is acceptable for administration to a subject, such as a mammal (e.g., salts having acceptable mammalian safety for a given dosage regime). Such salts can be derived from pharmaceutically acceptable inorganic or organic bases and from pharmaceutically-acceptable inorganic or organic acids, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically acceptable organic bases include salts of primary, secondary, tertiary and quaternary amines, including substituted amines, cyclic amines, naturally-occurring amines and the like, such as arginine, betaine, caffeine, choline, N, N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, N,N'-dibenzylethylenediamine, chloroprocaine, choline, diethanolamine, meglumine (N-methyl-glucamine) and the like. When compounds of the present disclosure contain relatively basic functionalities, acid addition salts can be obtained by contacting the neutral form of such compounds with a sufficient amount of the desired acid, either neat or in a suitable inert solvent. Salts derived from pharmaceutically acceptable acids include acetic, trifluoroacetic, propionic, ascorbic, benzenesulfonic, benzoic, camphosulfonic, citric, ethanesulfonic, fumaric, glycolic, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, hydroiodic, carbonic, tartaric, p-toluenesulfonic, pyruvic, aspartic, benzoic, anthranilic, mesylic, salicylic, p-hydroxybenzoic, phenylacetic, embonic (pamoic), ethanesulfonic, benzenesulfonic, 2-hydroxyethanesulfonic, sulfanilic, stearic, cyclohexylaminosulfonic, algenic, hydroxybutyric, galactaric and galacturonic acid and the like.

Also included are salts of amino acids such as arginate and the like, and salts of organic acids like glucuronic or galactunoric acids and the like (see, for example, Berge, S. M. et al., "Pharmaceutical Salts", J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated. The therapeutically effective amount will vary depending on the compound, the disorder or condition and its severity and the age, weight, etc., of the mammal to be treated. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

In addition, abbreviations as used herein have respective meanings as follows:

| | |
|---|---|
| ACN | acetonitrile |
| DCM | dichloromethane |
| DMF | dimethylformamide |
| DMSO | dimethylsulfoxide |
| DSC | differential scanning calorimetry |
| EtOAc | ethyl acetate |
| EtOH | ethanol |
| IPA | isopropanol |
| MeOH | methanol |
| RH | relative humidity |
| RT | room temperature |
| TGA | thermogravimetric analysis |
| THF | tetrahydrofuran |
| v/v | volume to volume |
| Wt | weight |
| w/w | weight to weight |
| XRPD | X-ray powder diffraction |

2. Forms of Compound I

As described generally above, the present disclosure provides crystalline forms of Compound I and salts, co-crystals, solvates, or hydrates thereof. Additional forms (including amorphous forms) are also discussed further herein. It is of note that the crystalline forms of Compound I and salts, co-crystals, solvates, or hydrates thereof, and other forms (e.g., amorphous forms) of Compound I and salts, co-crystals, solvates, or hydrates thereof are collectively referred to herein as "forms of Compound I" or "solid forms of Compound I."

It has been found that the crystalline forms of Compound I have surprisingly poor solubility as shown in Table A below, which provides solubility data of the active pharmaceutical ingredient of Compound I.

TABLE A

| Solubility of Active Pharmaceutical Ingredient of Compound I | |
|---|---|
| Acetone | 3 mg/mL |
| Acetonitrile | <1 mg/mL |
| Dichloromethane | <1 mg/mL |
| Dimethyl sulfoxide | >93 mg/mL |
| Ethyl acetate | <1 mg/mL |
| Ethanol | <1 mg/mL |
| Isopropanol | <1 mg/mL |
| Methanol | 1 mg/mL |
| Tetrahydrofuran | 19 mg/mL |
| Water | <1 mg/mL |

Thus, in some embodiments disclosed herein, techniques, methods and compositions for improving the solubility and/or bioavailability of Compound I are provided. In some embodiments, provided are compositions and methods involving Compound I in a composition, form, or formulation having improved solubility and/or bioavailability as compared to Compound I in a crystalline form. Accordingly, in some embodiments, provided are compositions and methods involving a free acid amorphous form of Compound I or a free acid amorphous salt form of Compound I, as disclosed herein. In some embodiments, provided are compositions and methods involving a free acid amorphous form of Compound I or a free acid amorphous salt form of Compound I molecularly dispersed within a polymer matrix.

a. Compound I Form A

The present disclosure provides, in one embodiment, a crystalline form of 4-(6-(3,5-dimethylisoxazol-4-yl)-1-[(1S)-1-(2-pyridyl)ethyl]pyrrolo[3,2-b]pyridin-3-yl)benzoic acid (Compound I Form A) characterized by an X-ray powder diffractogram comprising the following peaks: 17.1, 19.4, and 23.5°2θ±0.2°2θ, as determined on a diffractometer using Cu-Kα radiation. In one embodiment, the diffractogram of Compound I Form A further comprises one or more peaks at: 6.7, 9.7, 10.3, 12.1, 12.5, 15.8, 19.0, and 21.4, °2θ±0.2°2θ. In one embodiment, the diffractogram of Compound I Form A comprises at least two of the following peaks: 6.7, 9.7, 10.3, 12.1, 12.5, 15.8, 17.1, 19.0, 19.4, 21.4, and 23.5°2θ±0.2°2θ. In one embodiment, the diffractogram of Compound I Form A comprises at least four of the following peaks: 6.7, 9.7, 10.3, 12.1, 12.5, 15.8, 17.1, 19.0, 19.4, 21.4, and 23.5°2θ±0.2°2θ. In one embodiment, the diffractogram of Compound I Form A comprises at least six of the following peaks: 6.7, 9.7, 10.3, 12.1, 12.5, 15.8, 17.1, 19.0, 19.4, 21.4, and 23.5°2θ±0.2°2θ. In one embodiment, the diffractogram of Compound I Form A comprises at least eight of the following peaks: 6.7, 9.7, 10.3, 12.1, 12.5, 15.8, 17.1, 19.0, 19.4, 21.4, and 23.5°2θ±0.2°2θ. In one embodiment, the diffractogram of Compound I Form A comprises each of the following peaks: 6.7, 9.7, 10.3, 12.1, 12.5, 15.8, 17.1, 19.0, 19.4, 21.4, and 23.5°2θ±0.2°2θ. In one embodiment, Compound I Form A is characterized by the full X-ray powder diffractogram as substantially shown in FIG. 1.

Figure 2:
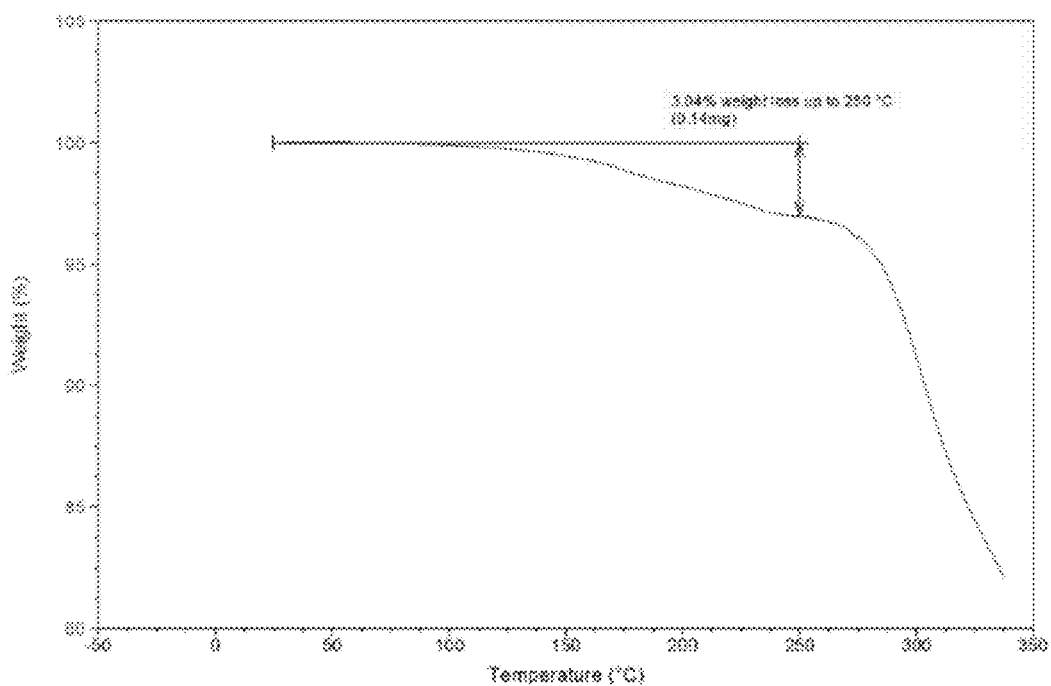
FIG. 2 is a thermogravimetric analysis (TGA) of Compound I Form A.

In one embodiment, Compound I Form A is characterized by a thermogravimetric analysis (TGA) thermogram showing a weight loss of about 3.0% up to about 250° C. In one embodiment, Compound I Form A is characterized by the thermogram as substantially shown in FIG. 2.

Figure 3:
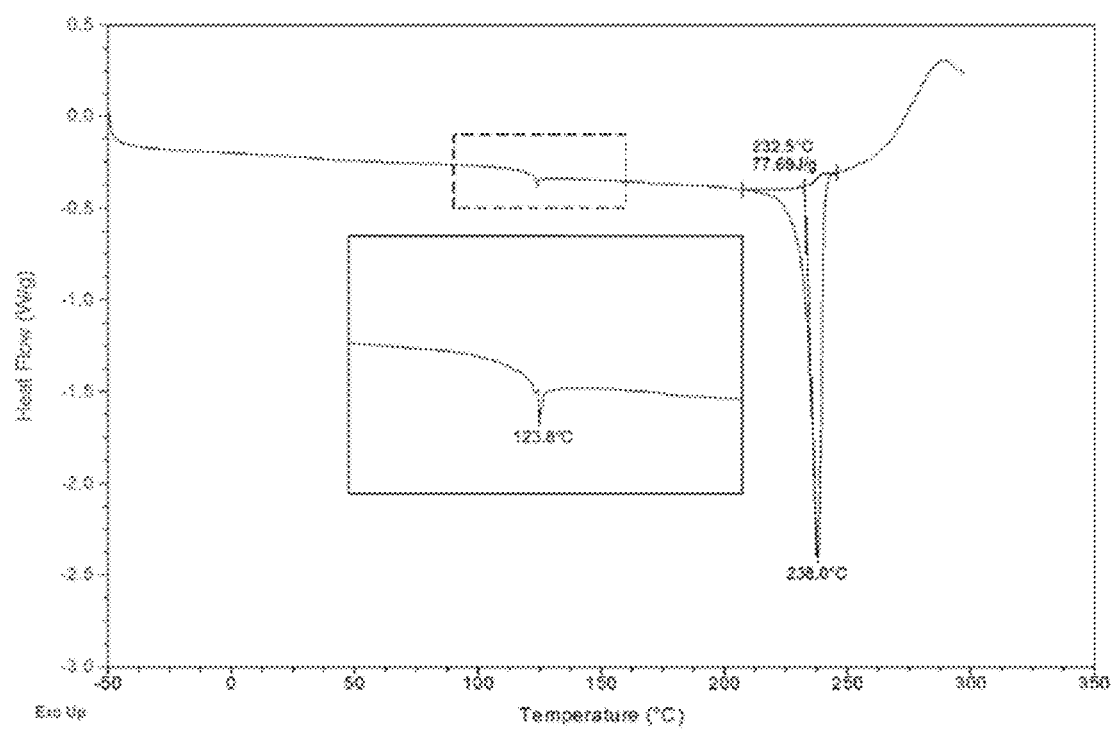
FIG. 3 is a differential scanning calorimeter (DSC) curve of Compound I Form A.

In one embodiment, Compound I Form A is characterized by a differential scanning calorimetry (DSC) curve that comprises an endotherm with a peak maximum at about 238° C. In one embodiment, the DSC curve of Compound I Form A comprises an additional endotherm with a peak maximum at about 124° C. In one embodiment, Compound I Form A is characterized by the full DSC curve as substantially shown in FIG. 3.

Figure 4:
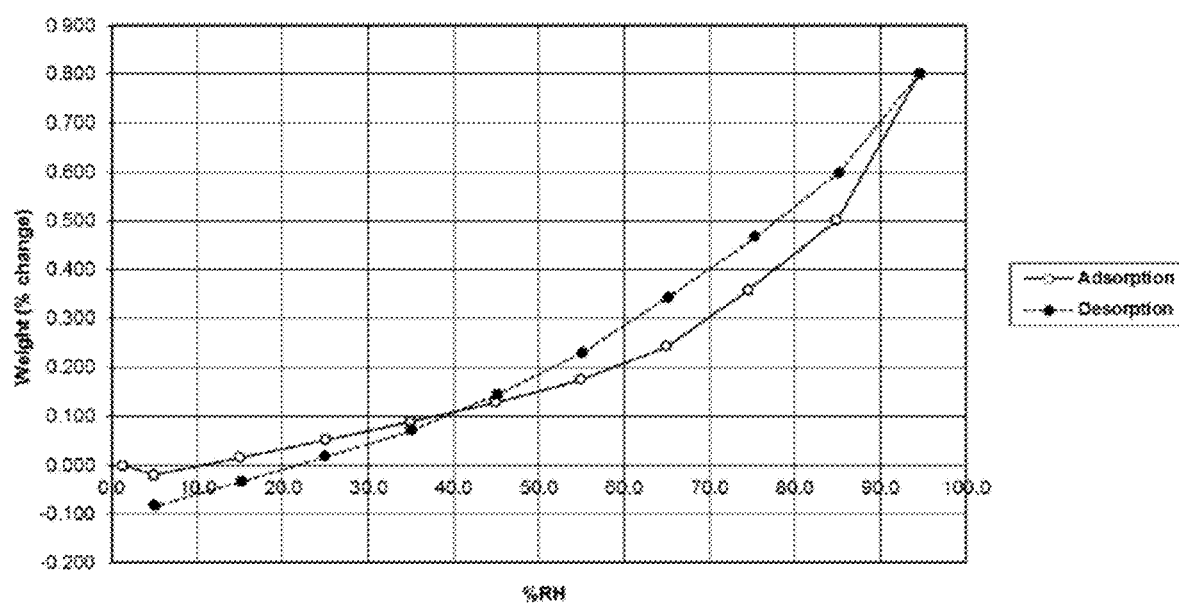
FIG. 4 is a dynamic vapor sorption (DVS) curve of Compound I Form A.

In one embodiment, Compound I Form A is characterized by a dynamic vapor sorption (DVS) analysis showing minimal weight loss upon equilibrium at about 5% RH, and a weight gain of about 0.8% from about 5% to about 95% RH corresponding to about 0.2 moles of water. In one embodiment, Compound I Form A is characterized by the full DVS sorption curve as substantially shown in FIG. 4.

In one embodiment, Compound I Form A is characterized as a hydrate.

b. Compound I Form B

Figure 5:
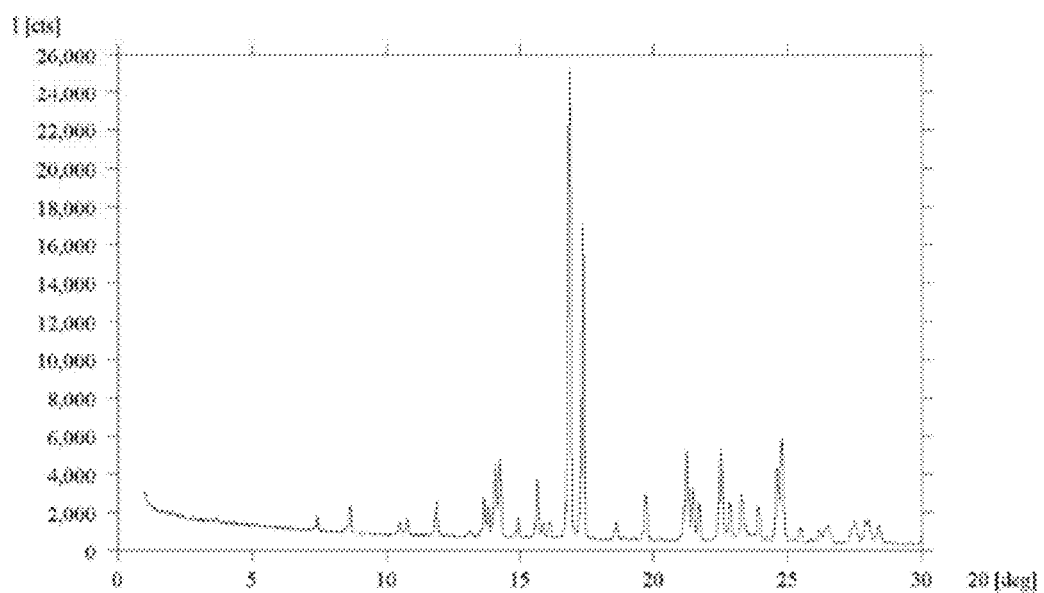
FIG. 5 is an X-ray powder diffractogram of Compound I Form B.

The present disclosure provides, in one embodiment, a crystalline form of 4-(6-(3,5-dimethylisoxazol-4-yl)-1-[(1S)-1-(2-pyridyl)ethyl]pyrrolo[3,2-b]pyridin-3-yl)benzoic acid (Compound I Form B) characterized by an X-ray powder diffractogram comprising the following peaks: 16.8, 17.4, and 21.1°2θ±0.2°2θ, as determined on a diffractometer using Cu-Kα radiation. In one embodiment, the diffractogram of Compound I Form B further comprises one or more peaks at: 13.7, 14.0, 14.2, 15.7, 19.7, 22.4, 23.2, and 24.6°2θ±0.2°2θ. In one embodiment, the diffractogram of Compound I Form B comprises at least two of the following peaks: 13.7, 14.0, 14.2, 15.7, 19.7, 22.4, 23.2, and 24.6°2θ±0.2°2θ. 13.7, 14.0, 14.2, 15.7, 16.8, 17.4, 19.7, 21.1, 22.4, 23.2, and 24.6°2θ±0.2°2θ. In one embodiment, the diffractogram of Compound I Form B comprises at least four of the following peaks: 13.7, 14.0, 14.2, 15.7, 19.7, 22.4, 23.2, and 24.6°2θ±0.2°2θ. 13.7, 14.0, 14.2, 15.7, 16.8, 17.4, 19.7, 21.1, 22.4, 23.2, and 24.6°2θ±0.2°2θ. In one embodiment, the diffractogram of Compound I Form B comprises at least six of the following peaks: 13.7, 14.0, 14.2, 15.7, 19.7, 22.4, 23.2, and 24.6°2θ±0.2°2θ. 13.7, 14.0, 14.2, 15.7, 16.8, 17.4, 19.7, 21.1, 22.4, 23.2, and 24.6°2θ±0.2°2θ. In one embodiment, the diffractogram of Compound I Form B comprises at least eight of the following peaks: 13.7, 14.0, 14.2, 15.7, 19.7, 22.4, 23.2, and 24.6°2θ±0.2°2θ. 13.7, 14.0, 14.2, 15.7, 16.8, 17.4, 19.7, 21.1, 22.4, 23.2, and 24.6°2θ±0.2°2θ. In one embodiment, the diffractogram of Compound I Form B comprises each of the following peaks: 13.7, 14.0, 14.2, 15.7, 19.7, 22.4, 23.2, and 24.6°2θ±0.2°2θ. 13.7, 14.0, 14.2, 15.7, 16.8, 17.4, 19.7, 21.1, 22.4, 23.2, and 24.6°2θ±0.2°2θ. In one embodiment, Compound I Form B is characterized by the full X-ray powder diffractogram as substantially shown in FIG. 5.

Figure 6:
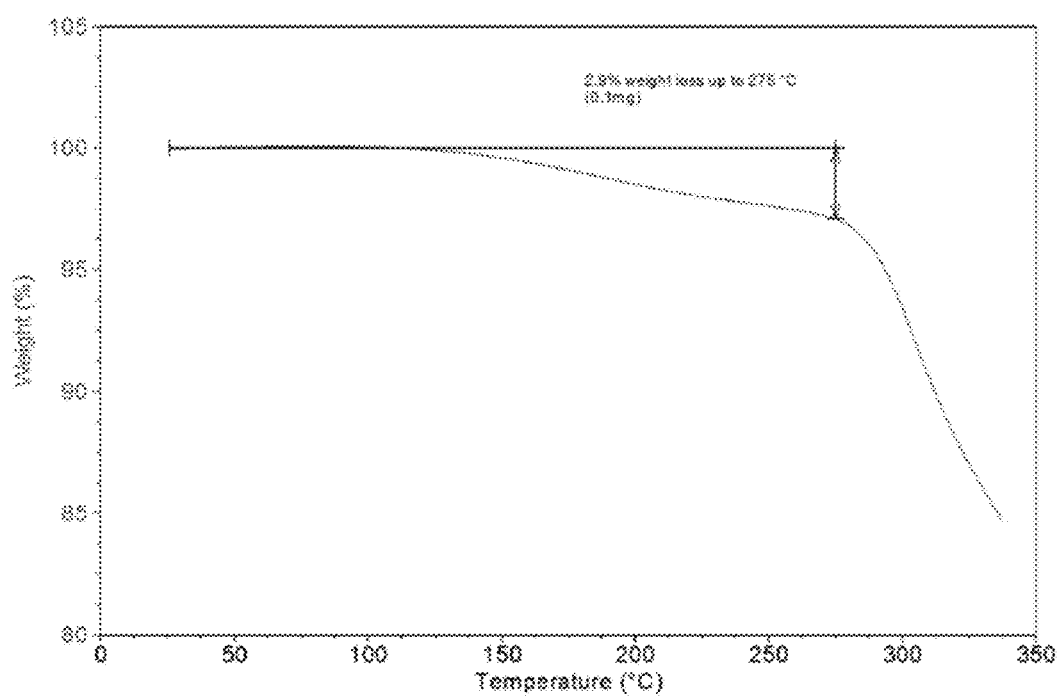
FIG. 6 is a thermogravimetric analysis (TGA) of Compound I Form B.

In one embodiment, Compound I Form B is characterized by a thermogravimetric analysis (TGA) thermogram showing a weight loss of about 2.9% up to about 275° C. In one embodiment, Compound I Form B is characterized by the thermogram as substantially shown in FIG. 6.

Figure 7:
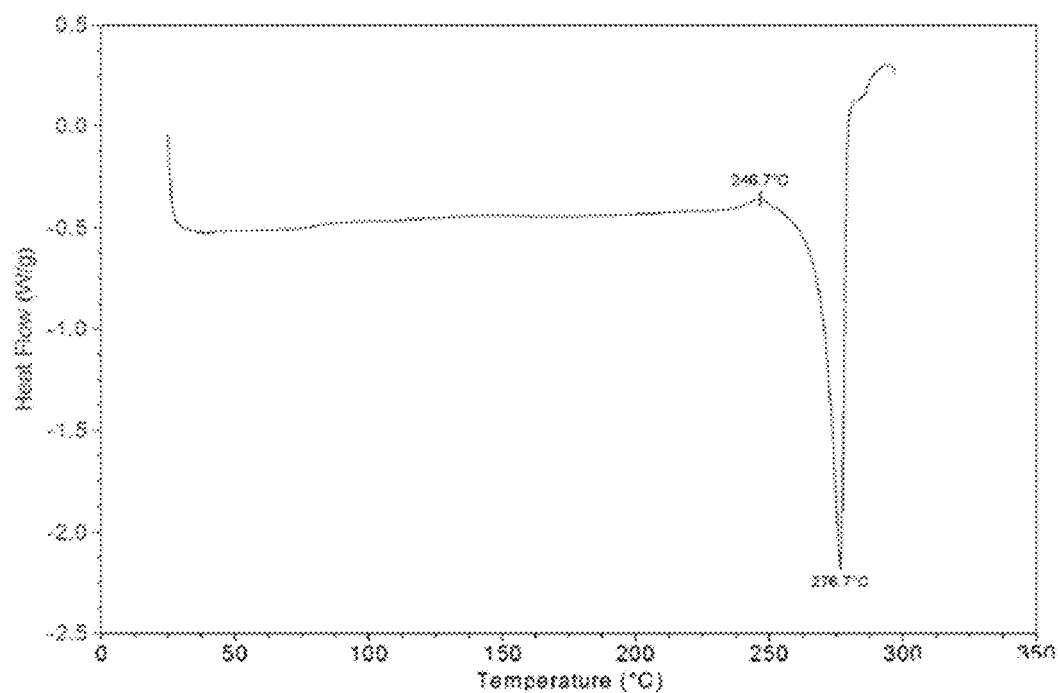
FIG. 7 is a differential scanning calorimeter (DSC) curve of Compound I Form B.

In one embodiment, Compound I Form B is characterized by a differential scanning calorimetry (DSC) curve that comprises an endotherm with a peak maximum at about 277° C. In one embodiment, the DSC curve of Compound I Form B additionally comprises an exotherm with a peak maximum at about 247° C. In one embodiment, Compound I Form B is characterized by the full DSC curve as substantially shown in FIG. 7.

In one embodiment, Compound I Form B is characterized as a racemic mixture comprising about an equal amount (50:50) of the R and S enantiomers of 4-(6-(3,5-dimethylisoxazol-4-yl)-1-[1-(2-pyridyl)ethyl]pyrrolo[3,2-b]pyridin-3-yl)benzoic acid. As indicated above, Compound I is the S enantiomer of 4-(6-(3,5-dimethylisoxazol-4-yl)-1-[1-(2-pyridyl)ethyl]pyrrolo[3,2-b]pyridin-3-yl)benzoic acid.

In one embodiment, Compound I Form B may exist as a solid solution comprising about an equal amount (50:50) of the R and S enantiomers of Compound I.

c. Compound I Form C

Figure 8:
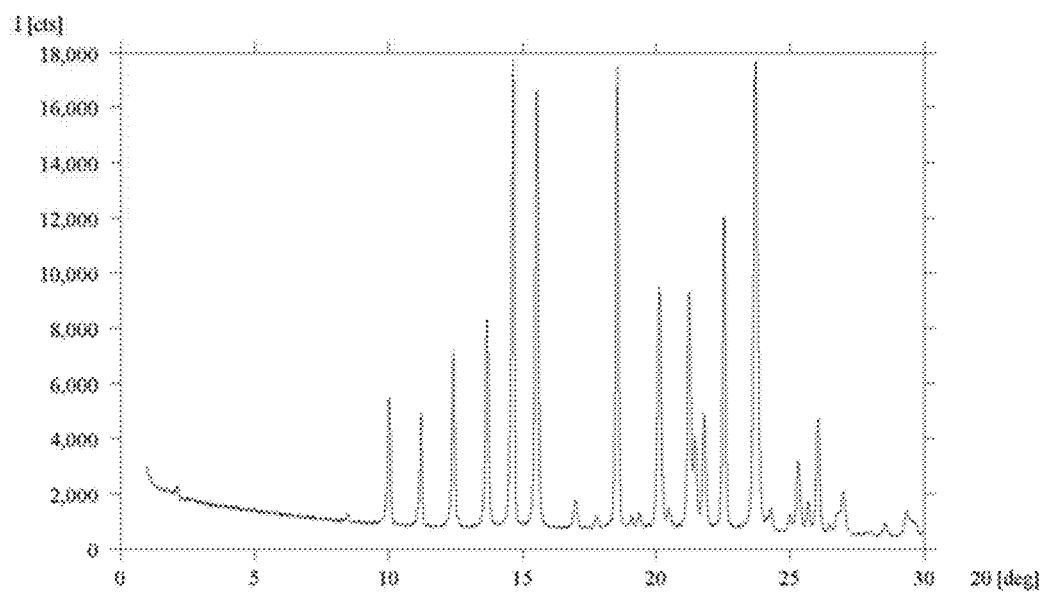
FIG. 8 is an X-ray powder diffractogram of Compound I Form C.

The present disclosure provides, in one embodiment, a crystalline form of 4-(6-(3,5-dimethylisoxazol-4-yl)-1-[(1S)-1-(2-pyridyl)ethyl]pyrrolo[3,2-b]pyridin-3-yl)benzoic acid (Compound I Form C) characterized by an X-ray powder diffractogram comprising the following peaks: 13.7, 14.6, and 22.6°2θ±0.2°2θ, as determined on a diffractometer using Cu-Kα radiation. In one embodiment, the diffractogram of Compound I Form C further comprises one or more peaks at: 10.0, 11.2, 12.4, 13.7, 14.6, 15.6, 18.6, 20.2, 21.3, 21.9, 22.6, and 23.8°2θ±0.2°2θ. In one embodiment, the diffractogram of Compound I Form C comprises at least two of the following peaks: 10.0, 11.2, 12.4, 13.7, 14.6, 15.6, 18.6, 20.2, 21.3, 21.9, 22.6, and 23.8°2θ±0.2°2θ. In one embodiment, the diffractogram of Compound I Form C comprises at least four of the following peaks: 10.0, 11.2, 12.4, 13.7, 14.6, 15.6, 18.6, 20.2, 21.3, 21.9, 22.6, and 23.8°2θ±0.2°2θ. In one embodiment, the diffractogram of Compound I Form C comprises at least six of the following peaks: 10.0, 11.2, 12.4, 13.7, 14.6, 15.6, 18.6, 20.2, 21.3, 21.9, 22.6, and 23.8°2θ±0.2°2θ. In one embodiment, the diffractogram of Compound I Form C comprises at least eight of the following peaks: 10.0, 11.2, 12.4, 13.7, 14.6, 15.6, 18.6, 20.2, 21.3, 21.9, 22.6, and 23.8°2θ±0.2°2θ. In one embodiment, the diffractogram of Compound I Form C comprises each of the following peaks: 10.0, 11.2, 12.4, 13.7, 14.6, 15.6, 18.6, 20.2, 21.3, 21.9, 22.6, and 23.8°2θ±0.2°2θ. In one embodiment, Compound I Form C is characterized by the full X-ray powder diffractogram as substantially shown in FIG. 8.

Figure 9:
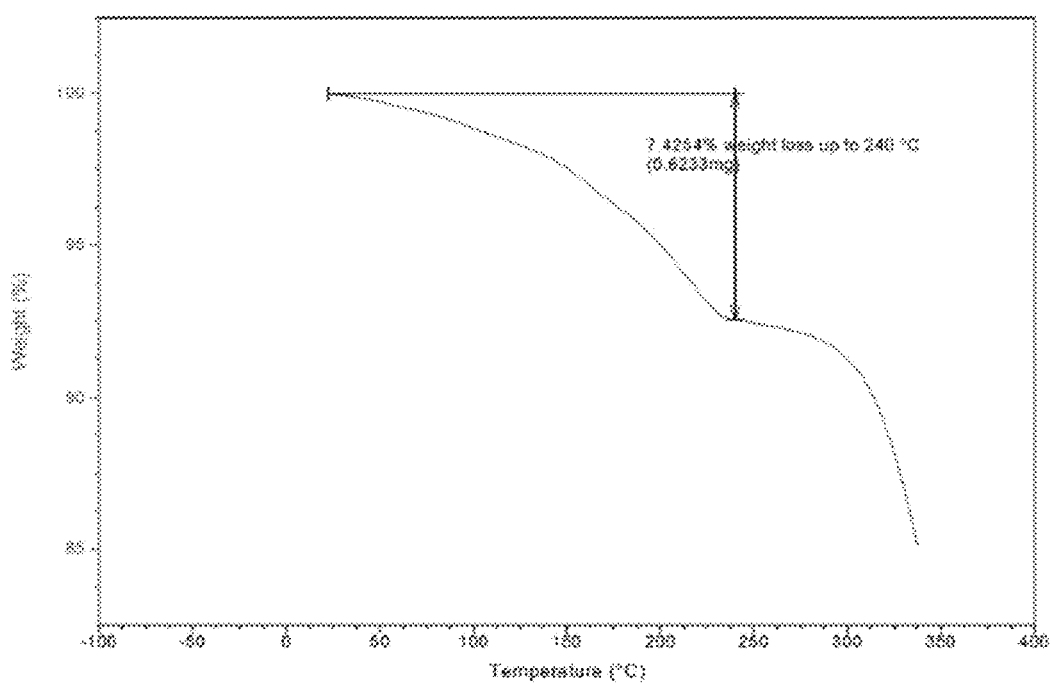
FIG. 9 is a thermogravimetric analysis (TGA) of Compound I Form C.

In one embodiment, Compound I Form C is characterized by a thermogravimetric analysis (TGA) thermogram showing a weight loss of about 7.4% up to about 240° C. In one embodiment, Compound I Form C is characterized by the thermogram as substantially shown in FIG. 9.

Figure 10:
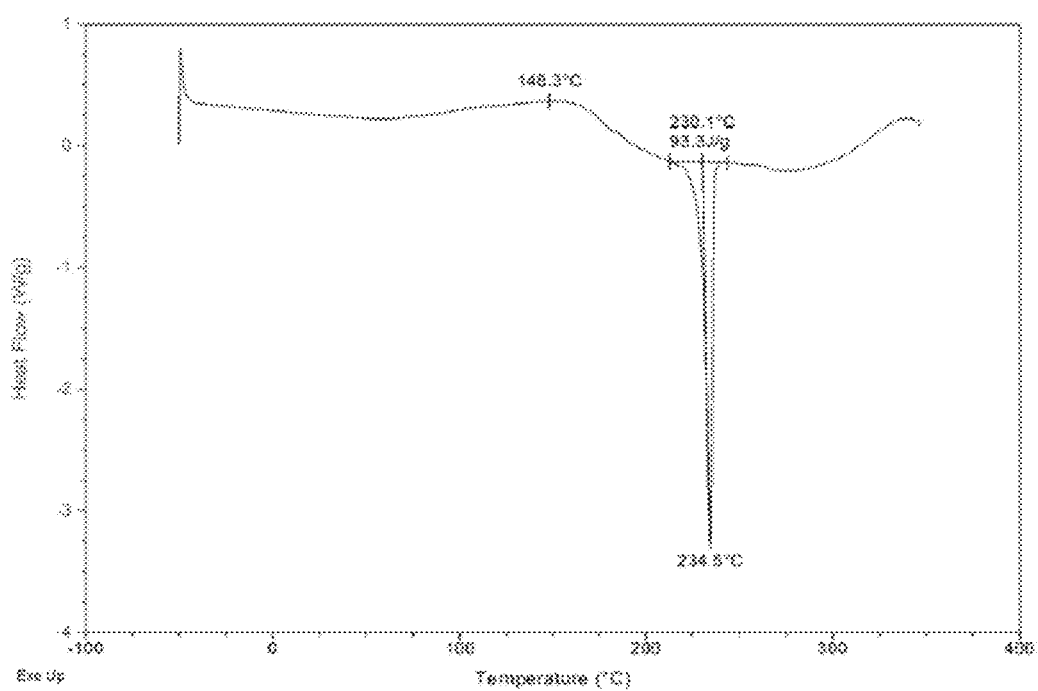
FIG. 10 is a differential scanning calorimeter (DSC) curve of Compound I Form C.

In one embodiment, Compound I Form C is characterized by a differential scanning calorimetry (DSC) curve that comprises an endotherm with a peak maximum at about 234.5° C. In one embodiment, the DSC curve of Compound I Form C additionally comprises an exotherm with a peak maximum at about 148° C. In one embodiment, Compound I Form C is characterized by the full DSC curve as substantially shown in FIG. 10.

In one embodiment, Compound I Form C is characterized as anhydrous.

d. Compound I Form D

Figure 11:
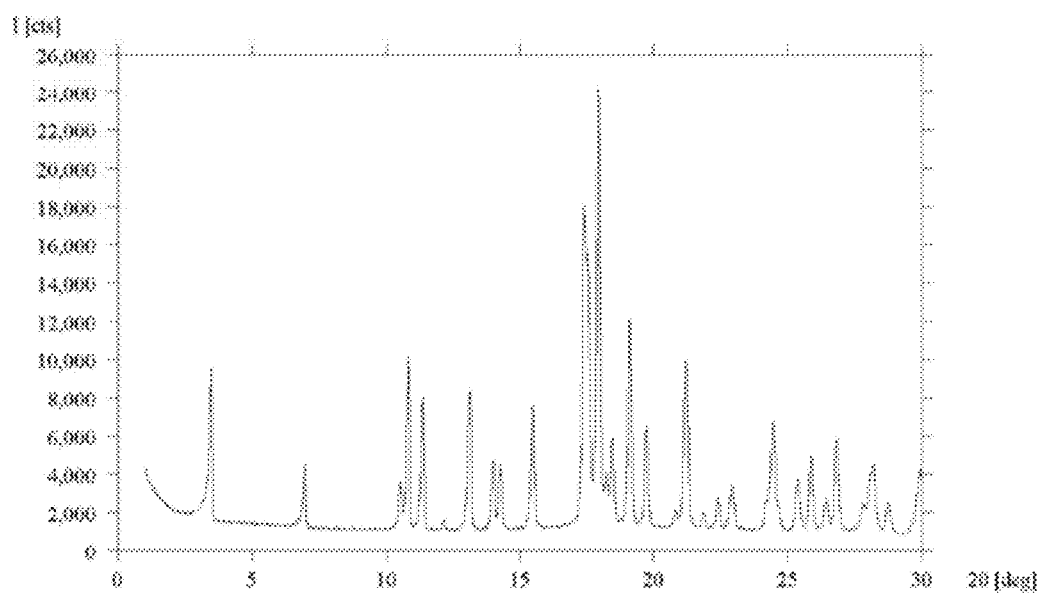
FIG. 11 is an X-ray powder diffractogram of Compound I Form D.

The present disclosure provides, in one embodiment, a crystalline form of 4-(6-(3,5-dimethylisoxazol-4-yl)-1-[(1S)-1-(2-pyridyl)ethyl]pyrrolo[3,2-b]pyridin-3-yl)benzoic acid (Compound I Form D) characterized by an X-ray powder diffractogram comprising the following peaks: 3.5, 18.0, and 19.1°2θ±0.2°2θ, as determined on a diffractometer using Cu-Kα radiation. In one embodiment, the diffractogram of Compound I Form D further comprises one or more peaks at: 7.0, 10.8, 11.4, 13.1, 15.5, 17.4, 17.5, 18.5, 19.7, and 21.2°2θ±0.2°2θ. In one embodiment, the diffractogram of Compound I Form D comprises at least two of the following peaks: 3.5, 7.0, 10.8, 11.4, 13.1, 15.5, 17.4, 17.5, 18.0, 18.5, 19.1, 19.7, and 21.2°2θ±0.2°2θ. In one embodiment, the diffractogram of Compound I Form D comprises at least four of the following peaks: 3.5, 7.0, 10.8, 11.4, 13.1, 15.5, 17.4, 17.5, 18.0, 18.5, 19.1, 19.7, and 21.2°2θ±0.2°2θ. In one embodiment, the diffractogram of Compound I Form D comprises at least six of the following peaks: 3.5, 7.0, 10.8, 11.4, 13.1, 15.5, 17.4, 17.5, 18.0, 18.5, 19.1, 19.7, and 21.2°2θ±0.2°2θ. In one embodiment, the diffractogram of Compound I Form D comprises at least eight of the following peaks: 3.5, 7.0, 10.8, 11.4, 13.1, 15.5, 17.4, 17.5, 18.0, 18.5, 19.1, 19.7, and 21.2°2θ±0.2°2θ. In one embodiment, the diffractogram of Compound I Form D comprises each of the following peaks: 3.5, 7.0, 10.8, 11.4, 13.1, 15.5, 17.4, 17.5, 18.0, 18.5, 19.1, 19.7, and 21.2°2θ±0.2°2θ. In one embodiment, Compound I Form D is characterized by the full X-ray powder diffractogram as substantially shown in FIG. 11.

Figure 12:
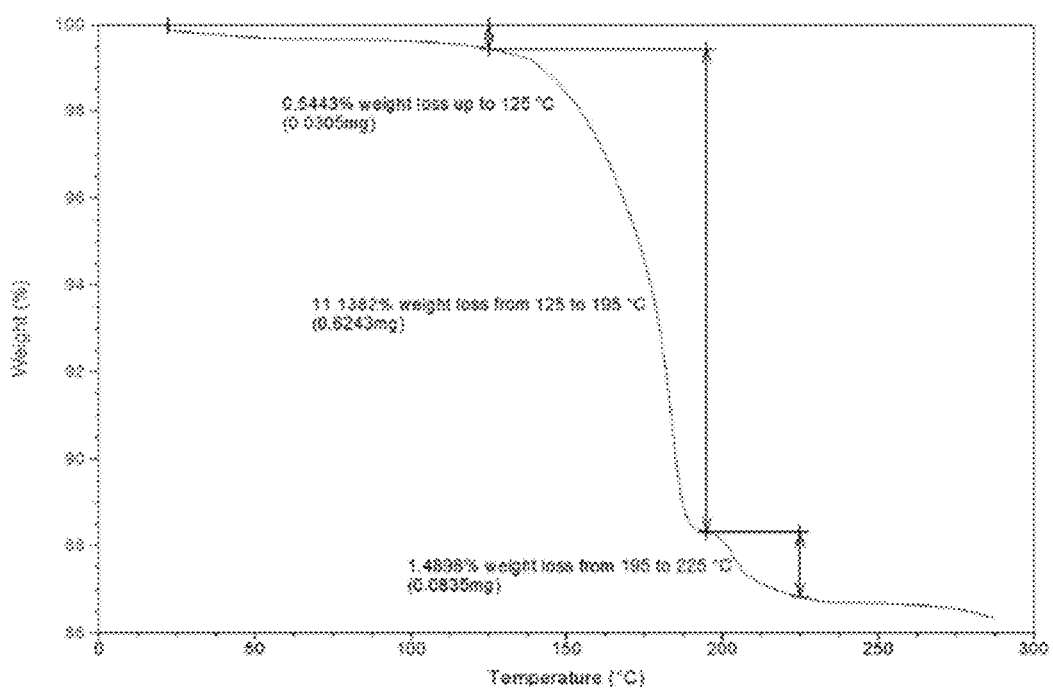
FIG. 12 is a thermogravimetric analysis (TGA) of Compound I Form D.

In one embodiment, Compound I Form D is characterized by a thermogravimetric analysis (TGA) thermogram showing a weight loss of about 0.5% up to about 125° C. In one embodiment, the TGA thermogram of Compound I Form D may additionally show a weight loss of about 11.1% from about 125° C. to about 195° C. In one embodiment, the TGA thermogram of Compound I Form D may further show a weight loss of about 1.5% from about 195° C. to about 225° C. In one embodiment, Compound I Form D is characterized by the thermogram as substantially shown in FIG. 12.

Figure 13:
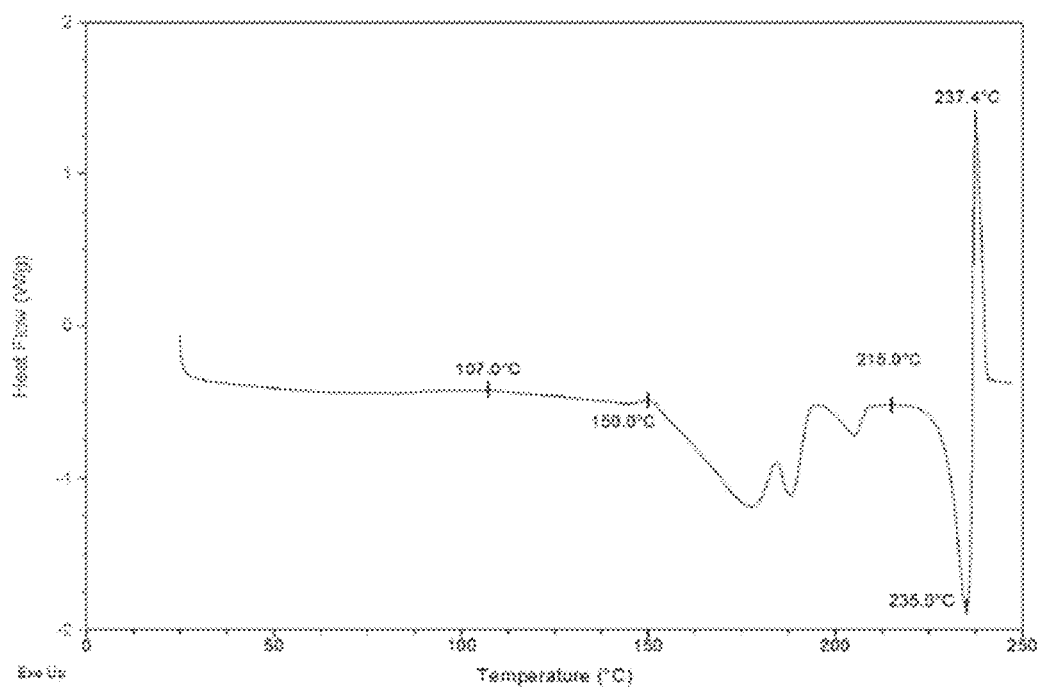
FIG. 13 is a differential scanning calorimeter (DSC) curve of Compound I Form D.

In one embodiment, Compound I Form D is characterized by a differential scanning calorimetry (DSC) curve that comprises an endotherm with a peak maximum at about 235° C. In one embodiment, the DSC curve of Compound I Form C additionally comprises exotherms with peak maxima at about 107° C. and 237° C. In one embodiment, Compound I Form C is characterized by the full DSC curve as substantially shown in FIG. 13.

In one embodiment, Compound I Form D is characterized as a solvate. In one embodiment, Compound I Form D is characterized as an isopropanol solvate.

e. Compound I Material E

The present disclosure provides, in one embodiment, a crystalline form of 4-(6-(3,5-dimethylisoxazol-4-yl)-1-[(1S)-1-(2-pyridyl)ethyl]pyrrolo[3,2-b]pyridin-3-yl)benzoic acid (Compound I Material E) characterized by an X-ray powder diffractogram comprising the following peaks: 6.4, 22.4, and 25.1°2θ±0.2°2θ, as determined on a diffractometer using Cu-Kα radiation. In one embodiment, the diffractogram of Compound I Material E further comprises one or more peaks at: 9.2, 10.6, 13.1, 19.0, 22.9, and 23.4°2θ±0.2°2θ. In one embodiment, the diffractogram of Compound I Material E comprises at least two of the following peaks: 6.4, 9.2, 10.6, 13.1, 19.0, 22.4, 22.9, 23.4, and 25.1°2θ±0.2°2θ. In one embodiment, the diffractogram of Compound I Material E comprises at least four of the following peaks: 6.4, 9.2, 10.6, 13.1, 19.0, 22.4, 22.9, 23.4, and 25.1°2θ±0.2°2θ. In one embodiment, the diffractogram of Compound I Material E comprises at least six of the following peaks: 6.4, 9.2, 10.6, 13.1, 19.0, 22.4, 22.9, 23.4, and 25.1°2θ±0.2°2θ. In one embodiment, the diffractogram of Compound I Material E comprises at least eight of the following peaks: 6.4, 9.2, 10.6, 13.1, 19.0, 22.4, 22.9, 23.4, and 25.1°2θ±0.2°2θ. In one embodiment, the diffractogram of Compound I Material E comprises each of the following peaks: 6.4, 9.2, 10.6, 13.1, 19.0, 22.4, 22.9, 23.4, and 25.1°2θ±0.2°2θ.

Figure 14:
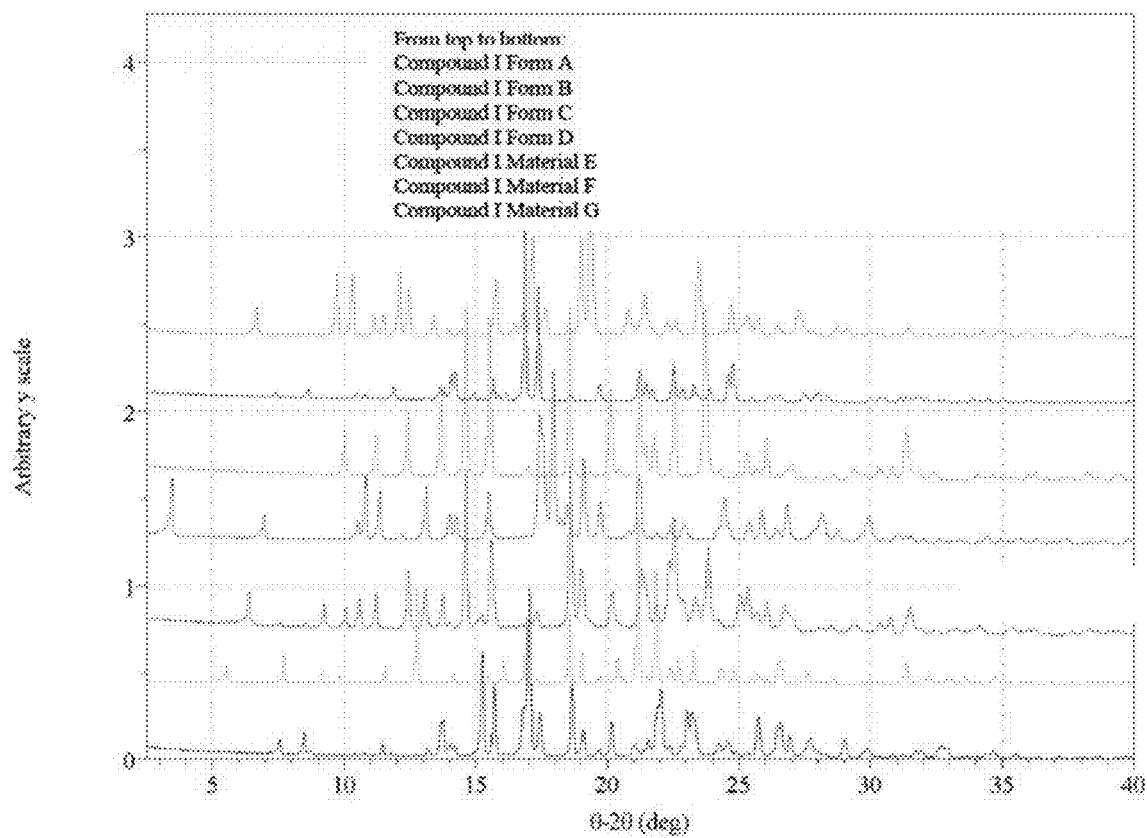
FIG. 14 are X-ray powder diffractograms of Compound I Form A, Compound I Form B, Compound I Form C, Compound I Form D, Compound I Material E, Compound I Material F and Compound I Material G.

In one embodiment, Compound I Material E is present as a mixture with Form C. In one embodiment, Compound I Material E is characterized by the full X-ray powder diffractogram as substantially shown in FIG. 14. FIG. 14 also includes the X-ray powder diffractograms of Compound I Form A, Compound I Form B, Compound I Form C, Compound I Form D, Compound I Material F (discussed in detail below) and Compound I Material G (discussed in detail below) for reference.

f Compound I Material F

The present disclosure provides, in one embodiment, a crystalline form of 4-(6-(3,5-dimethylisoxazol-4-yl)-1-[(1S)-1-(2-pyridyl)ethyl]pyrrolo[3,2-b]pyridin-3-yl)benzoic acid (Compound I Material F) characterized by an X-ray powder diffractogram comprising the following peaks: 12.8, 18.6, and 21.1°2θ±0.2°2θ, as determined on a diffractometer using Cu-Kα radiation. In one embodiment, the diffractogram of Compound I Material F further comprises one or more peaks at: 5.5, 7.7, 11.6, 16.1, 16.9, 19.0, 20.4, 21.9, and 23.3°2θ±0.2°2θ. In one embodiment, the diffractogram of Compound I Material F comprises at least two of the following peaks: 5.5, 7.7, 11.6, 12.8, 16.1, 16.9, 18.6, 19.0, 20.4, 21.1, 21.9, and 23.3°2θ±0.2°2θ. In one embodiment, the diffractogram of Compound I Material F comprises at least four of the following peaks: 5.5, 7.7, 11.6, 12.8, 16.1, 16.9, 18.6, 19.0, 20.4, 21.1, 21.9, and 23.3°2θ±0.2°2θ. In one embodiment, the diffractogram of Compound I Material F comprises at least six of the following peaks: 5.5, 7.7, 11.6, 12.8, 16.1, 16.9, 18.6, 19.0, 20.4, 21.1, 21.9, and 23.3°2θ±0.2°2θ. In one embodiment, the diffractogram of Compound I Material F comprises at least eight of the following peaks: 5.5, 7.7, 11.6, 12.8, 16.1, 16.9, 18.6, 19.0, 20.4, 21.1, 21.9, and 23.3°2θ±0.2°2θ. In one embodiment, the diffractogram of Compound I Material F comprises each of the following peaks: 5.5, 7.7, 11.6, 12.8, 16.1, 16.9, 18.6, 19.0, 20.4, 21.1, 21.9, and 23.3°2θ±0.2°2θ.

In one embodiment, Compound I Material F is present as a mixture with Form C. In one embodiment, Compound I Material F is characterized by the full X-ray powder diffractogram as substantially shown in FIG. 14.

g. Compound I Material G

The present disclosure provides, in one embodiment, a crystalline form of 4-(6-(3,5-dimethylisoxazol-4-yl)-1-[(1S)-1-(2-pyridyl)ethyl]pyrrolo[3,2-b]pyridin-3-yl)benzoic acid (Compound I Material G) characterized by an X-ray powder diffractogram comprising the following peaks: 15.3, 17.0, and 23.0°2θ±0.2°2θ, as determined on a diffractometer using Cu-Kα radiation. In one embodiment, the diffractogram of Compound I Material G further comprises one or more peaks at: 15.7, 18.7, 20.2, 21.9, 22.1, and 25.7, °2θ±0.2°2θ. In one embodiment, the diffractogram of Compound I Material G comprises at least two of the following peaks: 15.3, 15.7, 17.0, 18.7, 20.2, 21.9, 22.1, 23.0, and 25.7, °2θ±0.2°2θ. In one embodiment, the diffractogram of Compound I Material G comprises at least four of the following peaks: 15.3, 15.7, 17.0, 18.7, 20.2, 21.9, 22.1, 23.0, and 25.7, °2θ±0.2°2θ. In one embodiment, the diffractogram of Compound I Material G comprises at least six of the following peaks: 15.3, 15.7, 17.0, 18.7, 20.2, 21.9, 22.1, 23.0, and 25.7, °2θ±0.2°2θ. In one embodiment, the diffractogram of Compound I Material G comprises at least eight of the following peaks: 15.3, 15.7, 17.0, 18.7, 20.2, 21.9, 22.1, 23.0, and 25.7, °2θ±0.2°2θ. In one embodiment, the diffractogram of Compound I Material G comprises each of the following peaks: 15.3, 15.7, 17.0, 18.7, 20.2, 21.9, 22.1, 23.0, and 25.7, °2θ±0.2°2θ.

Figure 15:
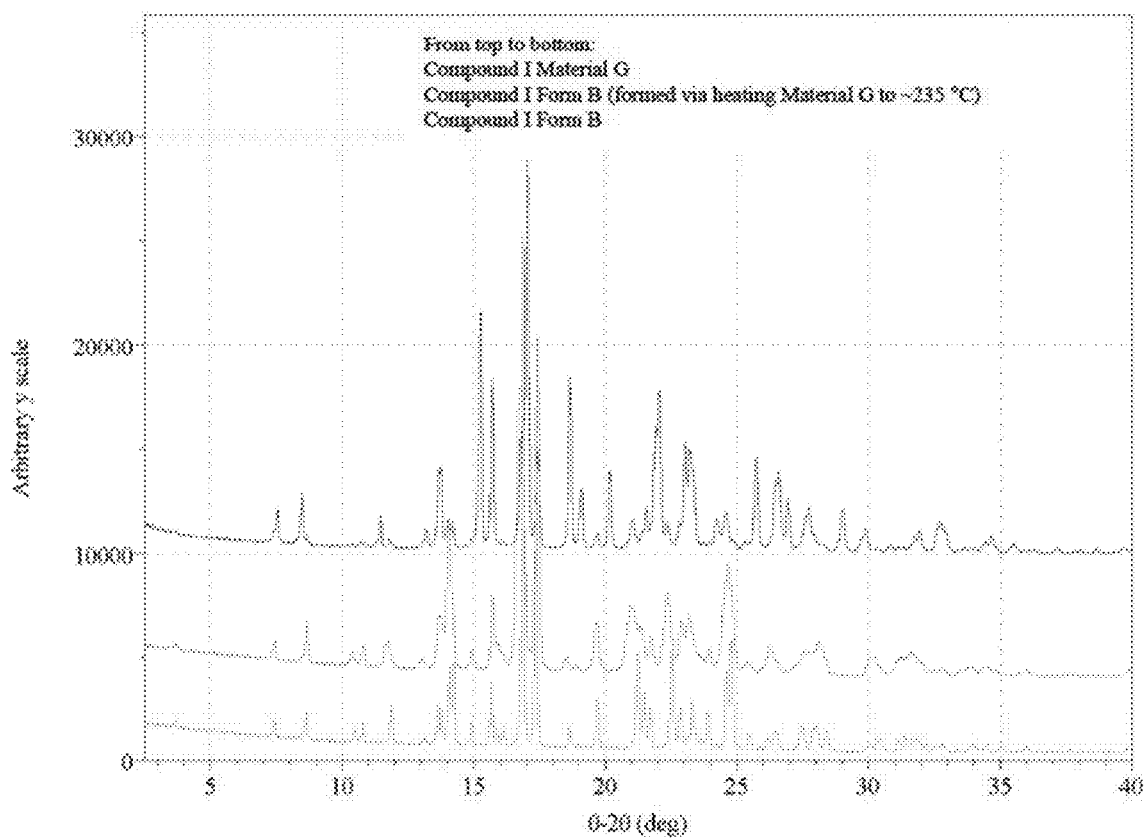
FIG. 15 are X-ray powder diffractograms of Compound I Material G and Compound I Form B.

In one embodiment, Compound I Material G is present as a mixture with Form B. In one embodiment, Compound I Material G is characterized by the full X-ray powder diffractogram as substantially shown in FIG. 15. FIG. 15 also includes the X-ray powder diffractogram of Compound I Form B for reference.

Figure 16:
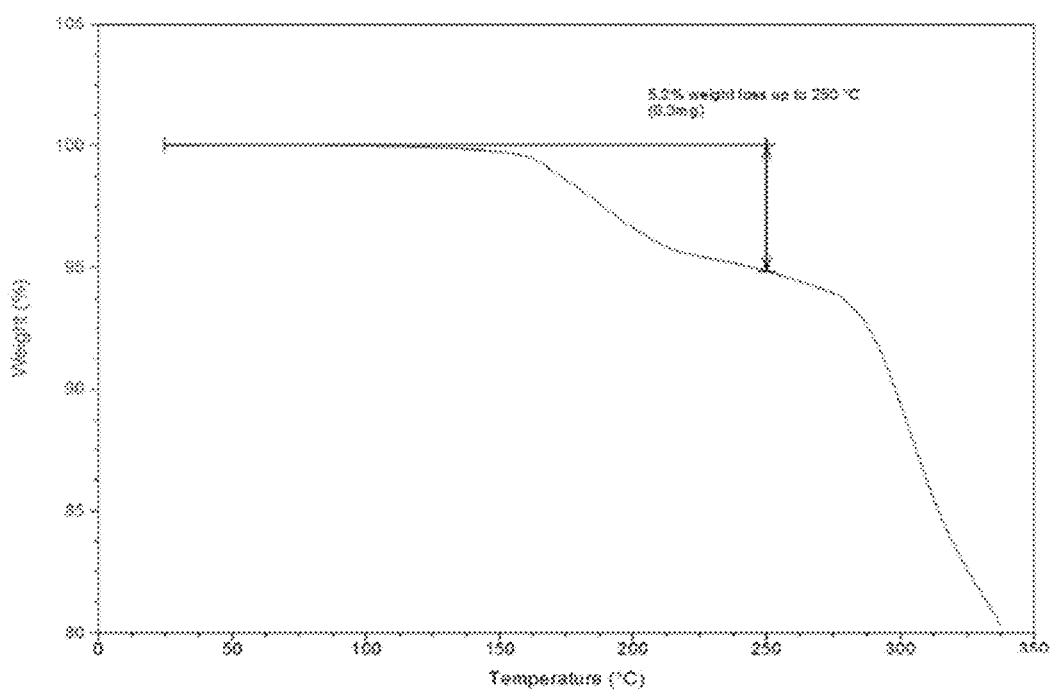
FIG. 16 is a thermogravimetric analysis (TGA) of Compound I Material G.

In one embodiment, Compound I Material G is characterized by a thermogravimetric analysis (TGA) thermogram showing a weight loss of about 5.2% up to about 250° C. In one embodiment, Compound I Material G is characterized by the thermogram as substantially shown in FIG. 16. In one embodiment, heating Compound I Material G up to about 235° C. results in a weight loss of about 4.2% and the formation of Compound I Form B. The X-ray powder diffractogram of Compound I Form B formed via heating Material G to about 235° C. is also shown in FIG. 15.

Figure 17:
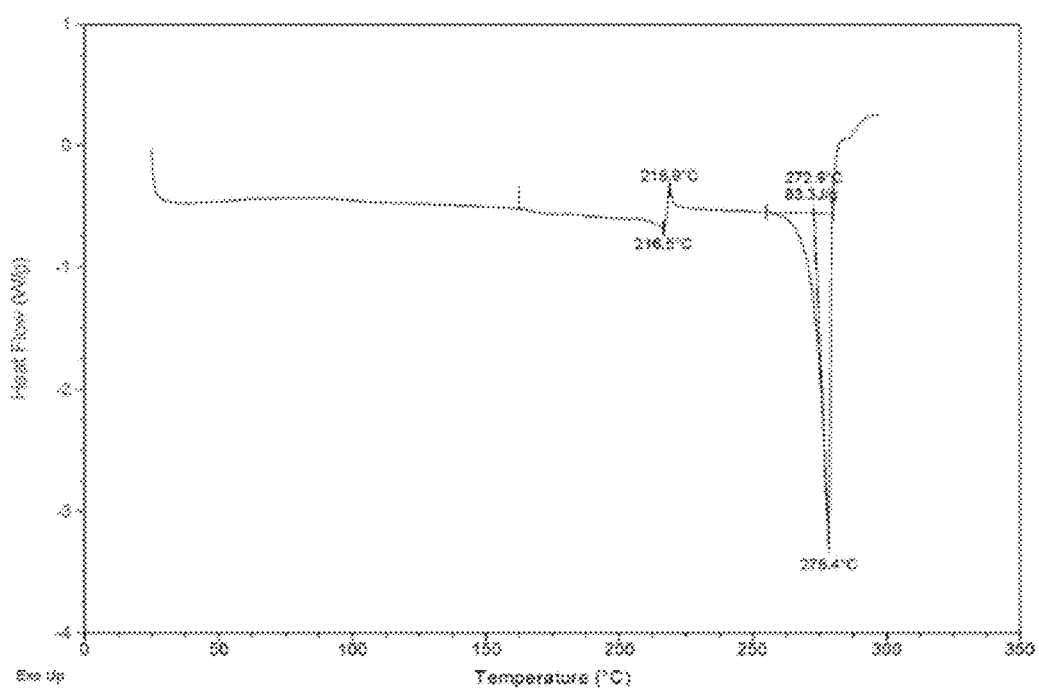
FIG. 17 is a differential scanning calorimeter (DSC) curve of Compound I Material G.

In one embodiment, Compound I Material G is characterized by a differential scanning calorimetry (DSC) curve that comprises an endotherm with a peak maximum at about 278° C. In one embodiment, the DSC curve of Compound I Material G comprises an additional endotherm with a peak maximum at about 217° C. In one embodiment, the DSC curve of Compound I Material G further comprises an exotherm with a peak maximum at about 219° C. In one embodiment, Compound I Material G is characterized by the full DSC curve as substantially shown in FIG. 17.

h. Compound I Free Acid Amorphous

Figure 18:
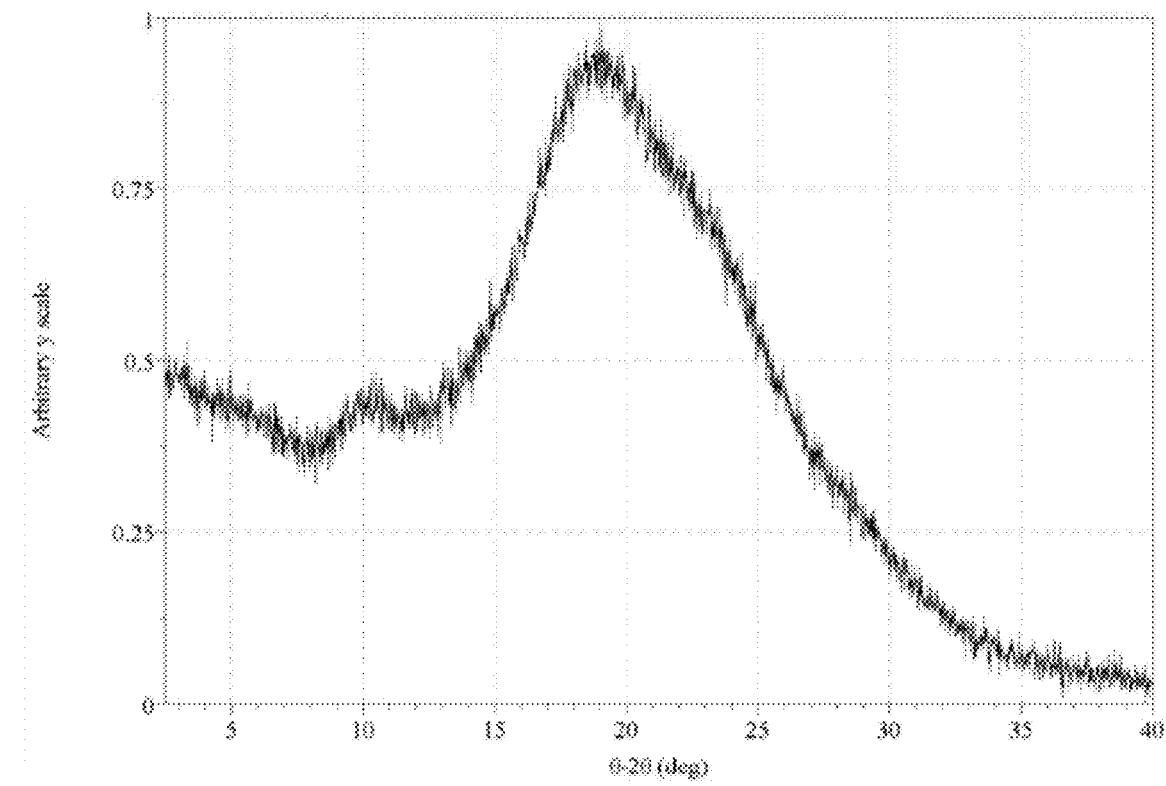
FIG. 18 is a X-ray powder diffractogram of Compound I Free Acid Amorphous.

The present disclosure provides, in one embodiment, a crystalline form of 4-(6-(3,5-dimethylisoxazol-4-yl)-1-[(1S)-1-(2-pyridyl)ethyl]pyrrolo[3,2-b]pyridin-3-yl)benzoic acid (Compound I Free Acid Amorphous, also referred to herein as the free acid amorphous form of Compound I) characterized by an X-ray powder diffractogram as substantially shown in FIG. 18.

Figure 19:
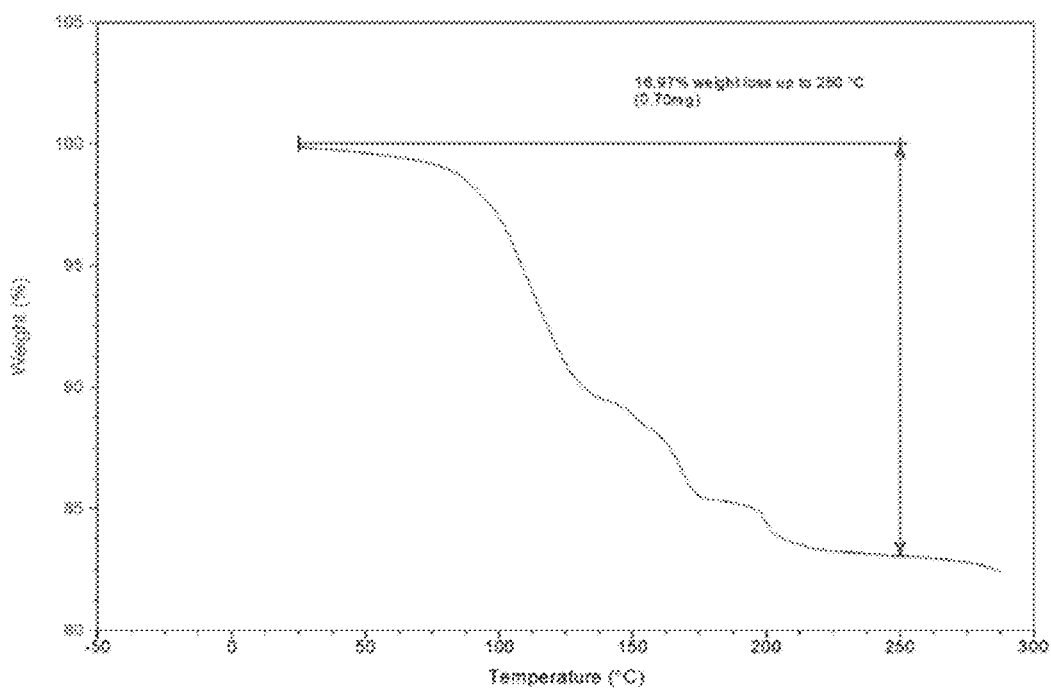
FIG. 19 is a thermogravimetric analysis (TGA) of Compound I Free Acid Amorphous.

In one embodiment, Compound I Free Acid Amorphous is characterized by a thermogravimetric analysis (TGA) thermogram showing a weight loss of about 17% up to about 250° C. In one embodiment, Compound I Free Acid Amorphous is characterized by the thermogram as substantially shown in FIG. 19.

Figure 20:
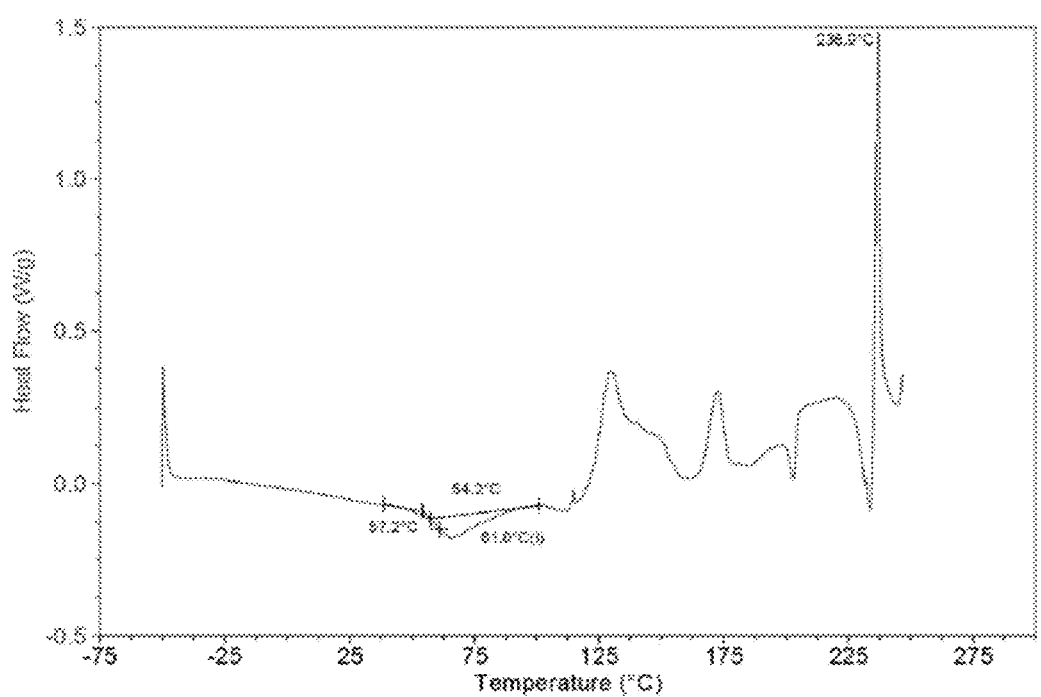
FIG. 20 is a differential scanning calorimeter (DSC) curve of Compound I Free Acid Amorphous.

In one embodiment, Compound I Free Acid Amorphous is characterized by a differential scanning calorimetry (DSC) curve that comprises an exotherm with a peak maximum at about 237° C. In one embodiment, the DSC curve of Compound I Free Acid Amorphous indicates a potential glass transition at about 57° C. In one embodiment, Compound I Free Acid Amorphous is characterized by the full DSC curve as substantially shown in FIG. 20.

i. Sodium Salt of Compound I

Figure 21:
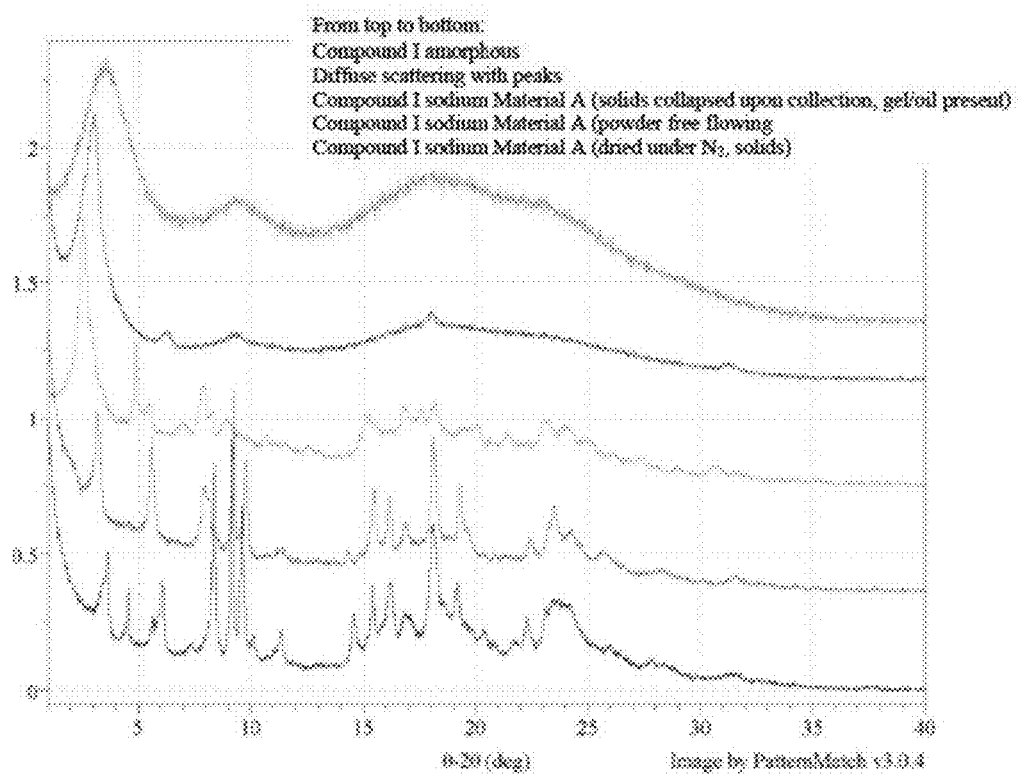
FIG. 21 are X-ray powder diffractogram of Compound I sodium Material A and Compound I Free Acid Amorphous.

The present disclosure provides, in one embodiment, a crystalline form of a sodium salt of 4-(6-(3,5-dimethylisoxazol-4-yl)-1-[(1S)-1-(2-pyridyl)ethyl]pyrrolo[3,2-b]pyridin-3-yl)benzoic acid (Compound I sodium Material A) characterized by an X-ray powder diffractogram as substantially shown in FIG. 21.

Figure 22:
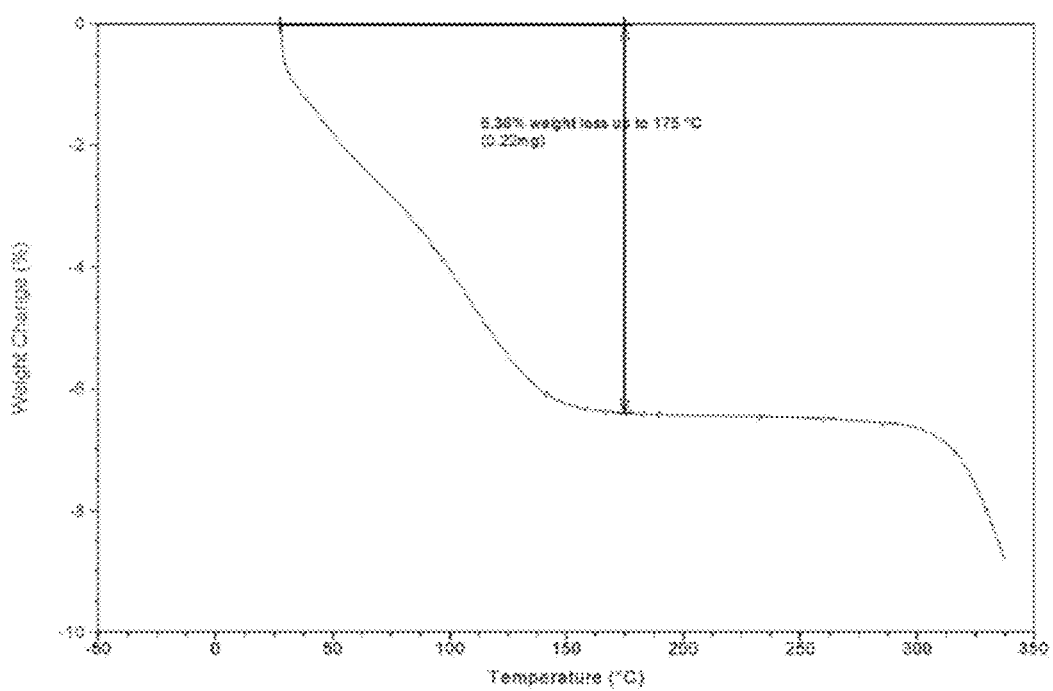
FIG. 22 is a thermogravimetric analysis (TGA) of Compound I sodium Material A.

In one embodiment, Compound I sodium Material A is characterized by a thermogravimetric analysis (TGA) thermogram showing a weight loss of about 6.4% up to about 175° C. In one embodiment, Compound I sodium Material A is characterized by the thermogram as substantially shown in FIG. 22.

Figure 23:
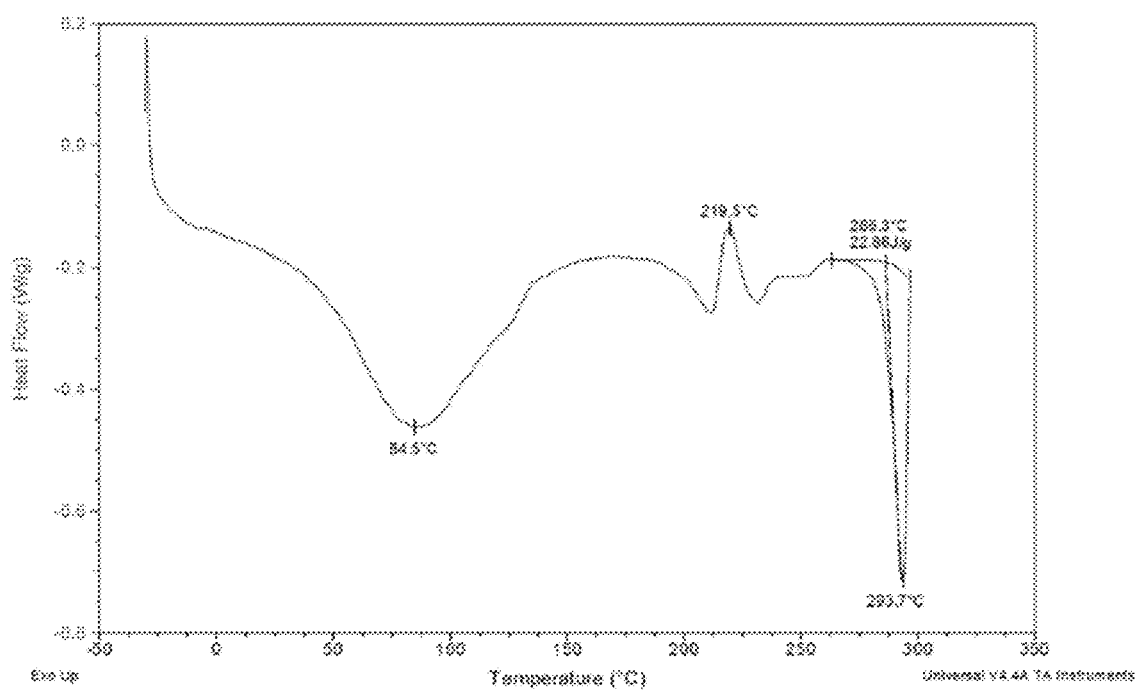
FIG. 23 is a differential scanning calorimeter (DSC) curve of Compound I sodium Material A.

In one embodiment, Compound I sodium Material A is characterized by a differential scanning calorimetry (DSC) curve that comprises an endotherm with a peak maximum at about 85° C. In one embodiment, the DSC curve of Compound I sodium Material A additionally comprises an endotherm with a peak maximum at about 294° C. In one embodiment, Compound I sodium Material A is characterized by the full DSC curve as substantially shown in FIG. 23.

3. Pharmaceutical Compositions and Modes of Administration

Compound I, and the forms thereof as described herein may be administered in a pharmaceutical composition. Thus, provided herein are pharmaceutical compositions comprising Compound I or a salt thereof, or one or more of the forms of Compound I described herein, and one or more pharmaceutically acceptable vehicles such as carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.). The pharmaceutical compositions may be administered alone or in combination with other therapeutic agents.

Some embodiments are directed to pharmaceutical compositions comprising Compound I. Some embodiments are directed to pharmaceutical compositions comprising a salt of Compound I.

Some embodiments are directed to pharmaceutical compositions comprising a crystalline form of Compound I as described herein. In one embodiment, a pharmaceutical composition comprises Compound I, wherein at least 95% of Compound I is in a crystalline form as described herein. In one embodiment, a pharmaceutical composition comprises Compound I, wherein at least 95% of Compound I is in Form A. In one embodiment, a pharmaceutical composition comprises Compound I, wherein at least 95% of Compound I is in Form B. In one embodiment, a pharmaceutical composition comprises Compound I, wherein at least 95% of Compound I is in Form C. In one embodiment, a pharmaceutical composition comprises Compound I, wherein at least 95% of Compound I is in Form D. In one embodiment, a pharmaceutical composition comprises Compound I, wherein at least 95% of Compound I is Compound I Material E. In one embodiment, a pharmaceutical composition comprises Compound I, wherein at least 95% of Compound I is Compound I Material F. In one embodiment, a pharmaceutical composition comprises Compound I, wherein at least 95% of Compound I is Compound I Material G.

In one embodiment, a pharmaceutical composition comprises Compound I, wherein at least 97% of Compound I is in a crystalline form as described herein. In one embodiment, a pharmaceutical composition comprises Compound I, wherein at least 97% of Compound I is in Form A. In one embodiment, a pharmaceutical composition comprises Compound I, wherein at least 97% of Compound I is in Form B. In one embodiment, a pharmaceutical composition comprises Compound I, wherein at least 97% of Compound I is in Form C. In one embodiment, a pharmaceutical composition comprises Compound I, wherein at least 97% of Compound I is in Form D. In one embodiment, a pharmaceutical composition comprises Compound I, wherein at least 97% of Compound I is Compound I Material E. In one embodiment, a pharmaceutical composition comprises Compound I, wherein at least 97% of Compound I is Compound I Material F. In one embodiment, a pharmaceutical composition comprises Compound I, wherein at least 97% of Compound I is Compound I Material G.

In one embodiment, a pharmaceutical composition comprises Compound I, wherein at least 99% of Compound I is in a crystalline form as described herein. In one embodiment, a pharmaceutical composition comprises Compound I, wherein at least 99% of Compound I is in Form A. In one embodiment, a pharmaceutical composition comprises Compound I, wherein at least 99% of Compound I is in Form B. In one embodiment, a pharmaceutical composition comprises Compound I, wherein at least 99% of Compound I is in Form C. In one embodiment, a pharmaceutical composition comprises Compound I, wherein at least 99% of Compound I is in Form D. In one embodiment, a pharmaceutical composition comprises Compound I, wherein at least 99% of Compound I is Compound I Material E. In one embodiment, a pharmaceutical composition comprises Compound I, wherein at least 99% of Compound I is Compound I Material F. In one embodiment, a pharmaceutical composition comprises Compound I, wherein at least 99% of Compound I is Compound I Material G.

In one embodiment, a pharmaceutical composition comprises an amorphous form of Compound I as described herein. In one embodiment, a pharmaceutical composition comprises a free acid amorphous form of Compound I as described herein. In one embodiment, a pharmaceutical composition comprises Compound I, where at least 95% of Compound I is Compound I Free Acid Amorphous. In one embodiment, a pharmaceutical composition comprises Compound I, where at least 97% of Compound I is Compound I Free Acid Amorphous. In one embodiment, a pharmaceutical composition comprises Compound I, wherein at least 99% of Compound I is Compound I Free Acid Amorphous.

In one embodiment, a pharmaceutical composition comprises a free acid amorphous salt form of Compound I (an amorphous form of a salt of Compound I) as described herein. In one embodiment, a pharmaceutical composition comprises Compound I, where at least 95% of Compound I is a free acid amorphous salt form of Compound I, as described herein. In one embodiment, a pharmaceutical composition comprises Compound I, where at least 97% of Compound I is a free acid amorphous salt form of Compound I, as described herein. In one embodiment, a pharmaceutical composition comprises Compound I, wherein at least 99% of Compound I is a free acid amorphous salt form of Compound I, as described herein.

In some embodiments, a pharmaceutical composition comprises Compound I Free Acid Amorphous molecularly dispersed in a polymer matrix. In some embodiments, a pharmaceutical composition comprises a free acid amorphous salt form of Compound I molecularly dispersed in a polymer matrix. Non-limiting examples of a polymer matrix that can be used include, but are not limited to, hypromellose Acetate Succinate (HPMCAS), hydroxypropyl methylcellulose phthalate (HPMCP), and Eudragit®.

Some embodiments are directed to pharmaceutical compositions comprising a salt of Compound I in a crystalline form as described herein. In one embodiment, a pharmaceutical composition comprises a sodium salt of Compound I, wherein at least 95% of Compound I is Compound I sodium Material A. In one embodiment, a pharmaceutical composition comprises a sodium salt of Compound I, wherein at least 97% of Compound I is Compound I sodium Material A. In one embodiment, a pharmaceutical composition comprises a sodium salt of Compound I, wherein at least 99% of Compound I is Compound I sodium Material A.

Some embodiments are directed to pharmaceutical compositions comprising a therapeutically effective amount of a compound selected from: Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, and Compound I sodium Material A as described herein; and one or more pharmaceutically acceptable carriers.

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-β-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the present disclosure (as a free-acid, solvate (including hydrate) or salt, in any form), depending on the condition being treated, the route of administration, and the age, weight and condition of the subject. Preferred unit dosage formulations are those containing a daily dose, weekly dose, monthly dose, a sub-dose or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including capsules, tablets, liquid-filled capsules, disintegrating tablets, immediate, delayed and controlled release tablets, oral strips, solutions, syrups, buccal and sublingual), rectal, nasal, inhalation, topical (including transdermal), vaginal or parenteral (including subcutaneous, intramuscular, intravenous or intradermal) route. Such formulations may be prepared by any method known in the art of pharmacy, for example by bringing into association the active ingredient with the carrier(s), excipient(s) or diluent. Generally, the carrier, excipient or diluent employed in the pharmaceutical formulation is "non-toxic," meaning that it/they is/are deemed safe for consumption in the amount delivered in the pharmaceutical composition, and "inert" meaning that it/they does/do not appreciably react with or result in an undesired effect on the therapeutic activity of the active ingredient.

In some embodiments, oral administration may be used. Pharmaceutical preparations for oral use can be formulated into conventional oral dosage forms such as discreet units capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethylcellulose, sodium carboxymethylcellulose (CMC), and/or polyvinylpyrrolidone (PVP: povidone); oily excipients, including vegetable and animal oils, such as sunflower oil, olive oil, or cod-liver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations, such as unit dosages. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures. Oral fluids such as solutions, syrups and elixirs can be prepared in dosage unit form so that a given quantity contains a predetermined amount of the compound.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use.

In some embodiments, transmucosal, topical or transdermal administration may be used. In such formulations of compounds described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, the compounds as disclosed herein (e.g., Compound I or a salt thereof, or one or more solid or amorphous forms of Compound I) are administered as inhalants. Compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds described herein (e.g., Compound I or a salt thereof, or one or more solid or amorphous forms of Compound I) may also be used in combination with other therapies, drugs, medical procedures, etc. for treating the same disease. In some embodiments, such combination use includes administration of one or more other therapies, drugs, or medical procedures at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. In some embodiments, use in combination includes use with at least one other therapy, drug or medical procedure that is administered once or infrequently, such as surgery, along with a compound described herein administered within a short time or longer time before or after the other therapy, drug or procedure. In some embodiments, use in combination includes delivery of a compound described herein and one or more other drug therapeutics by the same route or different routes of administration. In some embodiments, a compound described herein and one or more other drug therapeutics may be delivered together in any formulation by the same route of administration, including formulations where the compounds and other drug therapeutic(s) are chemically linked in such a way that they maintain their therapeutic activity when administered. In some embodiments, the other drug therapeutic(s) may be co-administered with a compound described herein. In some embodiments, co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapeutics delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components. In some embodiments, the compounds as disclosed herein may be used in adjuvant or neoadjuvant therapy in combination with other therapies or therapeutic agents as described herein. In some embodiments involving combination use, dosage may be modified for one or more of the compounds of the present disclosure or other therapeutics used in combination, e.g., reduction in the amount dosed relative to a compound or therapy used alone, by methods well known to those of ordinary skill in the art. Exemplary combination therapies are discussed below.

4. Disease Indications and Modulations of Bromodomain

Members of the BET (Bromodomain and Extra Terminal) family of bromodomain proteins (BRD2, BRD3, BRD4 and BRDT) have been associated with a variety of disorders including neurological diseases, autoimmune and inflammatory diseases, metabolic diseases (Muller et al. Expert Rev. Mol. Med. 2011, September 13; 13:e29; Prinjha et al. Trends Pharmacol. Sci. 2012, 33, 146-153; Belkina et al. J. Immunol. 2013, 190, 3670-3678; and Belkina et al. Nature Rev. Cancer 2012, 12, 465-477) and cancers (Alsarraj et al. International Journal of Breast Cancer 2012, 1-7; Barbieri et al. Briefings in Functional Genomics 2013, 1-12; Blobel et al. Cancer Cell 2011, 20, 287-288; Dang Cell 2012, 149, 22-35). In addition, some viruses make use of these proteins to tether their genomes to the host cells chromatin, as part of the process of viral replication (You et al. Cell, 2004 117, 349-60).

The compounds as described herein (e.g., Compound I or a salt thereof, or one or more solid or amorphous forms of Compound I) are useful for treating disorders related to one or more proteins involved in epigenetic regulation, such as proteins containing acetyl-lysine recognition motifs, i.e., bromodomains (e.g., BET proteins, such as BRD2, BRD3, BRD4, and/or BRDT), and e.g., diseases related to abnormal expression of bromodomains, including cell proliferative disorders, cancers, chronic autoimmune, inflammatory conditions, among others.

The presence of bromodomains has been associated with a number of different types of cancers, and other diseases and conditions, as described below. Bromodomain inhibitors are useful in the treatment of systemic or tissue inflammation, inflammatory responses to infection or hypoxia, cellular activation and proliferation, lipid metabolism, fibrosis and in the prevention and treatment of viral infections.

Bromodomain inhibitors such as the compounds described herein (e.g., Compound I or a salt thereof, or one or more solid or amorphous forms of Compound I) are useful in the prevention and treatment of chronic autoimmune and inflammatory conditions such as rheumatoid arthritis, uveal melanoma, chronic lymphocytic leukemia, acute myeloid leukemia, synovial sarcoma, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes, and acute rejection of transplanted organs.

Bromodomain inhibitors such as the compounds described herein (e.g., Compound I or a salt thereof, or one or more solid or amorphous forms of Compound I) are useful in the prevention and treatment of acute inflammatory conditions, including, but not limiting to, acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement and acute rejection of transplanted organs.

Bromodomain inhibitors such as the compounds described herein (e.g., Compound I or a salt thereof, or one or more solid or amorphous forms of Compound I) are useful in the prevention and treatment of autoimmune and inflammatory diseases or conditions which involve inflammatory responses to infections with bacteria, viruses, such as herpes virus, human papilloma virus, adenovirus and poxvirus and other DNA viruses; fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors such as the compounds described herein (e.g., Compound I or a salt thereof, or one or more solid or amorphous forms of Compound I) are useful in the prevention and treatment of diseases or conditions associated with ischemia-reperfusion injury, including, but not limiting to, myocardial infarction, cerebrovascular ischemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors such as the compounds described herein (e.g., Compound I or a salt thereof, or one or more solid or amorphous forms of Compound I) are useful in the prevention and treatment of hypercholesterolemia, atherosclerosis and Alzheimer's disease.

Bromodomain inhibitors such as the compounds described herein (e.g., Compound I or a salt thereof, or one or more solid or amorphous forms of Compound I) are useful in the prevention and treatment of cancers including, but not limiting to, hematological, epithelial including lung, breast and colon carcinomas, midline carcinomas, mesenchymal, hepatic, renal, neurological tumors, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation (also known as Richter's Syndrome), rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

5. Methods for Treating Conditions Mediated by Bromodomain

The present disclosure provides, in some embodiments, a method for modulating or inhibiting a bromodomain (e.g., a BET protein or BRD4 protein) or mutant thereof, wherein modulation or inhibition of bromodomain plays a role or provides some benefits. For instance, in some embodiments, the present disclosure provides a method for modulating or inhibiting a bromodomain or mutant thereof by contacting any one or more solid or amorphous forms of Compound I as described herein (e.g., Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), or a composition comprising any one or more solid or amorphous forms of Compound I as described herein, with a cell or a bromodomain protein in vitro or in vivo. In some embodiments, the present disclosure provides a method for modulating or inhibiting a bromodomain or mutant thereof by contacting Compound I or a salt thereof, or a composition comprising Compound I or a salt thereof, with a cell or a bromodomain protein in vitro or in vivo.

In some embodiments, the present disclosure provides a method for treating a subject suffering from or at risk of a bromodomain mediated disease or condition by administering to the subject an effective amount of any one or more solid or amorphous forms of Compound I as described herein (e.g., Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), or a composition comprising a compound as described herein. In some embodiments, the present disclosure provides a method for treating a subject suffering from or at risk of a bromodomain mediated disease or condition by administering to the subject an effective amount of Compound I or a salt thereof, or a composition comprising Compound I or a salt thereof. In some embodiments, the subject is a human. In some embodiments, the subject is a non-human animal.

In some embodiments, the present disclosure provides a method of suppressing undesired proliferation of tumor cells mediated by bromodomain. The method includes contacting tumor cells with an effective amount of a compound as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), or a composition comprising a compound as described herein. In some instances, the tumor cells are mediated by BET protein, BRD4 protein or a mutant thereof.

In some embodiments, the diseases or conditions treatable with one or more compounds as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A) include a cancer, a neurological condition, an autoimmune condition, an inflammatory condition, a metabolic disease, or combinations thereof.

In some embodiments, the diseases or conditions treatable with one or more compounds as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A) include, but are not limited to, a cancer, e.g., hematological, epithelial including lung, breast and colon carcinomas, midline carcinomas, mesenchymal, hepatic, renal, neurological tumors, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation (also known as Richter's Syndrome), rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, chronic lymphocytic leukemia, uterine cancer, verrucous carcinoma, visual pathway glioma, vulvar cancer, vaginal cancer, Waldenstrom's macroglobulinemia, Warthin's tumor, and Wilms' tumor.

In some embodiments, the cancer treatable with the compounds of the present disclosure (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A) is selected from adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

In some embodiments, the cancers or tumors treatable with the compounds of the present disclosure (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A) include benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratosis, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

In some embodiments, the diseases or conditions treatable with the compounds of the present disclosure (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A) include non-small cell lung cancer, small cell lung cancer, ovarian cancer, melanoma, midline carcinomas, breast cancer, lymphomas, neuroblastoma, or castration resistant prostate cancer, myelofibrosis, myelodysplastic syndromes, or acute myeloid leukemia.

In some embodiments, the diseases or conditions treatable with the compounds of the present disclosure (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A) include non-small cell lung cancer, small cell lung cancer, ovarian cancer, melanoma, neuroblastoma, and castration resistant prostate cancer.

In some embodiments, the present disclosure provides a method for treating a subject suffering or at risk of a disease or condition mediated by a bromodomain, or mutant thereof, by administering to the subject in need thereof an effective amount of any one or more solid or amorphous forms of Compound I as described herein (e.g., Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), or a composition comprising any one or more solid or amorphous forms of Compound I as described herein, where the disease or condition is chronic lymphocytic leukemia (CLL), Ricther's Syndrome, uveal melanoma, acute myeloid leukemia (AML), or myelodysplastic syndromes (MDS). In some embodiments, the present disclosure provides a method for treating a subject suffering or at risk of a disease or condition mediated by a bromodomain, or mutant thereof, by administering to the subject in need thereof an effective amount of Compound I or a salt thereof, or a composition comprising Compound I or a salt thereof, where the disease or condition is chronic lymphocytic leukemia (CLL), Ricther's Syndrome, uveal melanoma, acute myeloid leukemia (AML), or myelodysplastic syndromes (MDS). In one embodiment, the disease is chronic lymphocytic leukemia (CLL). In one embodiment, the disease or condition is Ricther's Syndrome. In one embodiment, the disease or condition is uveal cancer. In one embodiment, the disease or condition is myeloid leukemia. In one embodiment, the disease or condition is myelodysplastic syndromes (MDS).

In some embodiments, the present disclosure provides a method for treating a subject suffering or at risk of a disease or condition mediated by a bromodomain, or mutant thereof, by administering to the subject in need thereof an effective amount of any one or more solid or amorphous forms of Compound I as described herein (e.g., Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), or a composition comprising any one or more solid or amorphous forms of Compound I as described herein, where the disease or condition is chronic lymphocytic leukemia (CLL) or Ricther's Syndrome. In some embodiments, the present disclosure provides a method for treating a subject suffering or at risk of a disease or condition mediated by a bromodomain, or mutant thereof, by administering to the subject in need thereof an effective amount of Compound I or a salt thereof, or a composition comprising Compound I or a salt thereof, where the disease or condition is chronic lymphocytic leukemia (CLL) or Ricther's Syndrome. In one embodiment, the disease is chronic lymphocytic leukemia (CLL). In one embodiment, the disease or condition is Ricther's Syndrome.

In some embodiments, the present disclosure provides a method for treating a subject suffering or at risk of a disease or condition mediated by a bromodomain, or mutant thereof, by administering to the subject in need thereof an effective amount of any one or more solid or amorphous forms of Compound I as described herein (e.g., Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), or a composition comprising any one or more solid or amorphous forms of Compound I as described herein, where the disease or condition is acute myeloid leukemia (AML) or myelodysplastic syndromes (MDS). In some embodiments, the present disclosure provides a method for treating a subject suffering or at risk of a disease or condition mediated by a bromodomain, or mutant thereof, by administering to the subject in need thereof an effective amount of Compound I or a salt thereof, or a composition comprising Compound I or a salt thereof, where the disease or condition is acute myeloid leukemia (AML) or myelodysplastic syndromes (MDS). In one embodiment, the disease or condition is acute myeloid leukemia (AML). In one embodiment, the disease or condition is myelodysplastic syndromes (MDS).

In some embodiments, the diseases or conditions treatable with one or more compounds disclosed herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A) include autoimmune or inflammatory diseases or conditions. These autoimmune or inflammatory diseases or conditions may be chronic or acute and include, but are not limited to, inflammatory pelvic disease, urethritis, skin sunburn, sinusitis, pneumonitis, encephalitis, meningitis, myocarditis, pericarditis, nephritis including lupus nephritis, osteomyelitis, myositis, eczema, hepatitis, gastritis, enteritis, dermatitis, gingivitis, appendicitis, pancreatitis, primary biliary cirrhosis, cholecystitis, sclerosing cholangitis, agammaglobulinemia, psoriasis, allergy, Crohn's disease, irritable bowel syndrome, ulcerative colitis, Sjogren's disease, tissue graft rejection such as acute graft-versus-host disease, hyperacute rejection of transplanted organs, asthma, chronic obstructive airways disease, allergic rhinitis, chronic obstructive pulmonary disease (COPD), autoimmune polyglandular disease (also known as autoimmune polyglandular syndrome), autoimmune alopecia, pernicious anemia, vasculitis, glomerulonephritis, giant cell arteritis, Wegener's granulomatosis, Polyarteritis nodosa, dermatomyositis, multiple sclerosis, scleroderma, autoimmune hemolytic and thrombocytopenic states, Goodpasture's syndrome, atherosclerosis, Addison's disease, hypophysitis, Parkinson's disease, Alzheimer's disease, Kawasaki disease, Takayasu's Arteritis, depression, retinitis, uveitis, scleritis, Type I diabetes, septic shock, systemic lupus erythematosus (SLE), rheumatoid arthritis, psoriatic arthritis, juvenile arthritis, osteoarthritis, gout, chronic idiopathic thrombocytopenic purpura, Waldenstrom macroglobulinemia, myasthenia gravis, Hashimoto's thyroiditis, atopic dermatitis, degenerative joint disease, vitiligo, bullous skin diseases, autoimmune hypopituitarism, Guillain-Barre syndrome, Behcet's disease, scleracierma, mycosis fungoides, acute inflammatory responses (such as acute respiratory distress syndrome and ischemia/reperfusion injury), and Graves' disease. In some embodiments, the autoimmune and inflammatory diseases and conditions may also include systemic or tissue inflammation, inflammatory responses to hypoxia, cellular activation and proliferation, lipid metabolism, fibrosis, infections with bacteria, infections with viruses (e.g., herpes virus, human papilloma virus, adenovirus, poxvirus and other DNA viruses), fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

In some embodiments, the present disclosure provides methods for treating a subject suffering or at risk of ischemia-reperfusion injury by administering to the subject in need thereof an effective amount of a compound as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), or a composition comprising a compound as described herein. The ischemia-reperfusion injury, includes, but is not limited to, myocardial infarction, cerebro-vascular ischemia (stroke), acute coronary syndromes, renal reperfusion injury, organ transplantation, coronary artery bypass grafting, cardio-pulmonary bypass procedures, pulmonary, renal, hepatic, gastro-intestinal and peripheral limb embolism.

In some embodiments, the present disclosure provides a method for treating a subject suffering or at risk of a disease or condition mediated by a bromodomain, or mutant thereof, by administering to the subject in need thereof an effective amount of any one or more solid or amorphous forms of Compound I as described herein (e.g., Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), or a composition comprising any one or more solid or amorphous forms of Compound I as described herein, where the disease or condition is rheumatoid arthritis, uveal melanoma, chronic lymphocytic leukemia, acute myeloid leukemia, synovial sarcoma, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes, or acute rejection of transplanted organs. In some embodiments, the present disclosure provides a method for treating a subject suffering or at risk of a disease or condition mediated by a bromodomain, or mutant thereof, by administering to the subject in need thereof an effective amount of Compound I or a salt thereof, or a composition comprising Compound I or a salt thereof, where the disease or condition is rheumatoid arthritis, uveal melanoma, chronic lymphocytic leukemia, osteoarthritis, acute myeloid leukemia, synovial sarcoma, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes, or acute rejection of transplanted organs. In one embodiment, the disease or condition is rheumatoid arthritis. In one embodiment, the disease or condition is osteoarthritis. In one embodiment, the disease or condition is acute gout. In one embodiment, the disease or condition is psoriasis. In one embodiment, the disease or condition is systemic lupus. In one embodiment, the disease or condition is systemic lupus. In one embodiment, the disease or condition iserythematosus. In one embodiment, the disease or condition is multiple sclerosis. In one embodiment, the disease or condition is inflammatory bowel disease. In one embodiment, the disease or condition is Crohn's disease. In one embodiment, the disease or condition is ulcerative colitis. In one embodiment, the disease or condition is asthma. In one embodiment, the disease or condition is chronic obstructive airways disease. In one embodiment, the disease or condition is pneumonitis. In one embodiment, the disease or condition is myocarditis. In one embodiment, the disease or condition is pericarditis. In one embodiment, the disease or condition is myositis. In one embodiment, the disease or condition is eczema. In one embodiment, the disease or condition is dermatitis. In one embodiment, the disease or condition is alopecia. In one embodiment, the disease or condition is vitiligo. In one embodiment, the disease or condition is bullous skin diseases. In one embodiment, the disease or condition is nephritis. In one embodiment, the disease or condition is vasculitis. In one embodiment, the disease or condition is atherosclerosis. In one embodiment, the disease or condition is Alzheimer's disease. In one embodiment, the disease or condition is depression. In one embodiment, the disease or condition is retinitis. In one embodiment, the disease or condition is uveitis. In one embodiment, the disease or condition is scleritis. In one embodiment, the disease or condition is hepatitis. In one embodiment, the disease or condition is pancreatitis. In one embodiment, the disease or condition is primary biliary cirrhosis. In one embodiment, the disease or condition is sclerosing cholangitis. In one embodiment, the disease or condition is Addison's disease. In one embodiment, the disease of condition is hypophysitis. In one embodiment, the disease or condition is thyroiditis. In one embodiment, the disease or condition is Type I diabetes. In one embodiment, the disease or condition is acute rejection of transplanted organs.

In some embodiments, the present disclosure provides methods for treating a subject suffering or at risk of hypercholesterolemia by administering to the subject in need thereof an effective amount of any one or more solid or amorphous forms of Compound I as described herein (e.g., Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), or a composition comprising any one or more solid or amorphous forms of Compound I as described herein. In some embodiments, the present disclosure provides methods for treating a subject suffering or at risk of hypercholesterolemia by administering to the subject in need thereof an effective amount of Compound I or a salt thereof, or a composition comprising Compound I or a salt thereof.

In some embodiments, the present disclosure provides use of a compound as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), or a composition comprising a compound as described herein, in the manufacture of a medicament for the treatment of a disease or condition as described herein. In some embodiments, the present disclosure provides a compound as described herein, or a composition comprising a compound as described herein, for use in treating a disease or condition as described herein.

As discussed in detail below, the present disclosure provides combination therapies for treating a subject suffering from or at risk of the diseases or conditions described herein, where such combination therapies comprise administering to the subject in need thereof any one or more of the compounds disclosed herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), or a composition comprising any one or more of the compounds as described herein, in combination with one or more other therapeutic agents including, but not limited to, a BCL-2 inhibitor, a PI3K inhibitor, BTK inhibitor, a CTLA-4 inhibitor, a checkpoint inhibitor, or quizartinib.

The following literature publications describe just some examples of these uses for bromodomain inhibitors.

Since compounds described herein have been shown to be bromodomain inhibitors, then the following publications confirm utilities of the claimed compounds.

Cancer

Bromodomain inhibitors have been administered to humans in clinical trials for breast cancer, non-small cell lung cancer, small cell lung cancer, acute myeloid leukemia, myelodysplastic neoplasm, myelodysplastic syndrome, midline carcinoma, castration resistant prostate cancer, pancreatic cancer, multiple myeloma, colorectal cancer, and neuroblastoma (C. A. French, Small-Molecule Targeting of BET Proteins in Cancer, Advances in Cancer Research, (2016), 131, 21-58).

Bromodomain 4 (BRD4) inhibitor inhibits colorectal cancer growth and metastasis colorectal cancer (Y. Hu, et al., BRD4 Inhibitor Inhibits Colorectal Cancer Growth and Metastasis, Int. J. Mol. Sci. (2015), 16, 1928-1948).

Bromodomain inhibitors inhibits castration-resistant prostate cancer (I. A. Asangani, et al., Therapeutic targeting of BET bromodomain proteins in castration-resistant prostate cancer, Nature (2014), 510, 278-282).

A panel of neuroblastoma cell lines were administered bromodomain inhibitors which resulted in potent growth inhibition and cytotoxicity in most cell lines (A. Wyce, et al., BET Inhibition Silences Expression of MYCN and BCL2 and Induces Cytotoxicity in Neuroblastoma Tumor Models, PLOS ONE (2013), 8, 8, 1-16).

Bromodomain inhibitors potently reduces the viability in acute lymphoblastic leukemia (C. J. Ott, et al., BET bromodomain inhibition targets both c-MYC and IL7R in high-risk acute lymphyoblastic leukemia, Blood Journal (2012), 1-23).

Bromodomain inhibitors selectively suppress proliferation of mouse and human AML cell lines. (A. F. Hohmann et al., Sensitivity and engineered resistance of myeloid leukemia cells to BRD9 inhibition, Nature Chemical Biology (2016), 12, 672-679).

Compound I of this disclosure was found to be a structurally distinct BET inhibitor with novel in vitro and in vivo pharmacologic properties that emulatesor exceeds the efficacy of B-cell receptor (BCR) signaling agents in preclinical models of CLL. (H. G. Ozer et al., BRD4 profiling identifies critical Chronic Lymphocytic Leukemia oncogenic circuits and reveals sensitivity to PLX51107, a novel structurally distinct BET inhibitor, Cancer Discovery, Published Online Mar. 14, 2018 doi: 10.1158/2159-8290.CD-17-0902).

In mouse xenograft models of uveal melanoma (UM) Compound I of this disclosure significantly inhibited tumor growth. (G. Ambrosini et al., Cytotoxic Effects of a Novel BRD4 Inhibitor in Uveal Melanoma Cells with Gnaq/11 Mutations, Molecular and Cellular Biology, Genetics, DOI: 10.1158/1538-7445.AM2016-4462 Published July 2016).

Several bromodomain inhibitor drug candidates have progressed into clinical trials for myelodysplastic syndrome, AML, multiple myeloma, and Glioblastoma Multiform (G. W. Rhyasen, et al., AZD5153: A Novel Bivalent BET Bromodomain Inhibitor Highly Active against Hematologic Malignancies, Mol. Cancer Ther. (2016), 15, 11, 2563-2574).

Bromodomain 4 (BRD4) inhibitors have been found to lead to selective inhibition of MYC oncogene in multiple myeloma (J. Loven, et al., Selective Inhibition of Tumor Oncogenes by Disruption of Super-Enhancers, Cell (2013), 153, 320-334).

Potent antimyeloma activity was observed with bromodomain inhibitors (A. Chaidos, et al., Potent antimyeloma activity of the novel bromodomain inhibitors I-BET151 and I-BET762, Blood (2014), 123, 5, 697-705).

Bromodomain inhibitors were found induce cell cycle arrest in Glioblastoma Multiforme cells (C. Pastori, et al., The Bromodomain protein BRD4 controls HOTAIR, a long noncoding RNA essential for glioblastoma proliferation, PNAS (2015), 1-6).

It has been demonstrated that suppression of BRD4 correlates with suppression of Merkel Cell Carcinoma xenograft tumor growth (D. Sengupta, et al., Disruption of BRD4 at H3K27Ac-enriched enhancer region correlates with decreased c-Myc expression in Merkel cell carcinoma, Epigenetics (2015), 10, 6, 460-466).

BRD4 inhibitors have suppressed breast cancer cell growth (J. Shi, et al., Disrupting the Interaction of BRD4 with Diacetylated Twist Suppresses Tumorigenesis in Basal-like Breast Cancer, Cancer Cell (2014), 25, 210-225).

It has been demonstrated that bromodomain inhibition primes NSCLC cells for induction of apoptosis, and BRD inhibitors show differential anti-proliferative activity in a panel of NSCLC cell lines (O. Klingbeil, et al., Inhibition of BET bromodomain-dependent XIAP and FLIP expression sensitizes KRAS-mutated NSCLC to pro-apoptic agents, Cell Death and Disease (2016), 7, e2365, doi:10.1038/cddis.2016.271, 1-13).

BRD4 inhibitors significantly inhibit the proliferation and survival of osteosarcoma cells (D. H. Lee et al., Synergistic Effect of JQ1 2014 and Rapamycin for Treatment of Human Osteosarcoma, Int. J. Cancer (2015), 135, 2055-2064).

Bromodomain inhibitors demonstrated inhibitory effects on ovarian cancer cell lines (A. M Kurimchak, et al., Resistance to BET Bromodomain Inhibitors is Mediated by Kinome Reprogramming in Ovarian Cancer, Cell Reports (2016), 16, 1273-1286).

Bromodomain inhibitors potently inhibit gastric cancer cell growth (R. C. Montenegro, et al., BET inhibition as a new strategy for the treatment of gastric cancer, Oncotarget (2016), 7, 28, 43997-44012).

Certain LAC cell lines are acutely susceptible to bromodomain inhibition (W. W. Lockwood, et al., Sensitivity of human lung adenocarcinoma cell lines to targeted inhibition of BET epigenetic signaling proteins, PNAS (2012), 109, 47, 19408-19413)

BRD4 is a promising target for midline carcinoma (J. Lu et al., Hijacking the E3 Ubiquitin Ligase Cereblon to Efficiently Target BRD4, Chemistry & Biology (2015), 22, 755-763).

It has been found that BRD4 inhibitors suppress both growth and tumorigenesis of malignant peripheral nerve sheath tumors (MPNST) (A. J. Patel et al., BET Bromodomain Inhibition Triggers Apoptosis of NF1-Associated Malignant Peripheral Nerve Sheath Tumors through Bim Induction, Cell Reports (2014), 6, 1-12).

Bromodomain inhibitors have been found to cause apoptosis and reduce growth of melanoma cells (A. Heinemann et al., Combining BET and HDAC inhibitors synergistically induces apoptosis of melanoma and suppresses AKT and YAP signaling, Oncotarget (2015) 6, 25, 21507-21521).

BRD4 inhibition has been characterized as a novel therapeutic intervention against uveal melanoma (G. Ambrosini et al., BRD4-targeted therapy induces Myc-independent cytotoxicity in Gnaq/11-mutant uveal melanoma cells, Oncotarget (2015), 6, 32, 33397-33409).

Mice harboring medulloblastoma xenografts exhibited prolonged survival when treated with bromodomain inhibitors (A. Hennsen et al., BET bromodomain protein inhibition is a therapeutic option for medulloblastoma, Oncotarget (2013), 4, 11, 2080-2095).

Lymphoma

Bromodomain inhibitors inhibit the proliferation of lymphoma cell lines of different origins (M. Jung, et al., Targeting BET bromodomains for cancer treatment, Epigenomics (2015), 7(3), 487-501).

Bromodomain inhibitors have been shown to be affective against Burkitt's Lymphoma (S. Wu, et al., Phospho Switch Triggers Brd4 Chromotin Binding and Activator Recruitment for Gene-Specific Targeting, Molecular Cell (2013), 49, 1-15; J. Lu et al., Hijacking the E3 Ubiquitin Ligase Cereblon to Efficiently Target BRD4, Chemistry & Biology (2015), 22, 755-763).

Bromodomain inhibition induces apoptosis in B-cell lymphoma (S. J. Hogg et al., BET inhibition Induces Apoptosis in Aggressive B-Cell Lymphoma via Epigenetic Regulation of BCL-2 Family Members, Mol Cancer Ther (2016), 15, 9, 2030-2041).

Inflammation and Autoimmune Disorders

Bromodomain inhibitors have been shown to be effective for the treatment of disease indications such as autoimmune diseases and inflammation (O. A. Kharenko, et al., RVX-297-a novel BD2 selective inhibitor of BET bromodomains, Biochemical and Biophysical Research Communication (2016), 477, 62-67).

It has been found that bromodomain inhibition provides beneficial activity for the disease area of autoimmunity (D. U. Lee et al., Nonselective inhibition of the epigenetic transcriptional regulator BET induces marked lymphoid and hematopoietic toxicity in mice, Toxicology and Applied Pharmacology (2016), 300, 47-54).

It has been found that bromodomain inhibition ameliorates colitis in mice (K. Cheung et al., BET N-terminal bromodomain inhibition selectively blocks Th17 cell differentiation and ameliorates colitis in mice, PNAS (2017), 114, 11, 2952-2957).

BRD4 inhibitors reduces IL-1β-induced inflammation in human airway epithelial cells and may be effective for treating chronic obstructive pulmonary disease (Y. M. Khan, et al., Brd4 is Essential for IL-1β-Induced Inflammation in Human Airway Epithelial Cells, PLOS ONE (2014), 9, 4, 1-17).

Bromodomain inhibition provides beneficial activity for atherosclerosis (D. U. Lee et al., Nonselective inhibition of the epigenetic transcriptional regulator BET induces marked lymphoid and hematopoietic toxicity in mice, Toxicology and Applied Pharmacology (2016), 300, 47-54).

Arthritic/Joint Related Diseases

Bromodomain inhibitors decreases joint swelling and inflammation and helps to prevent bone loss, which can be useful for treating rheumatoid arthritis and osteoarthritis (K. Park-Min, et al., Inhibition of osteoclastogenesis and inflammatory bone resorption by targeting BET proteins and epigenetic regulation, Nature Communications (2014), 5:5418, 1-9).

Bromodomains mediate inflammatory-related pathologies such as rheumatoid arthritis (K. A. Papavassiliou, et al., Bromodomains: pockets with therapeutic potential, Trends in Molecular Medicine (2014), 20, 9, 477-478).

6. Combination Therapy

Bromodomain modulators may be usefully combined with another pharmacologically active compound, or with two or more other pharmacologically active compounds, particularly in the treatment of cancer and other diseases and indications described herein. In one embodiment, the composition includes any one or more compound(s) as described (e.g., Compound I or a salt thereof, or any one or more solid or amorphous forms of Compound I) along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In some embodiments, the present disclosure provides a composition, e.g., a pharmaceutical composition comprising any one or more solid or amorphous forms of Compound I as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A) and one or more other therapeutic agents. In some embodiments, the present disclosure provides a composition, e.g., a pharmaceutical composition comprising Compound I or a salt thereof and one or more other therapeutic agents. In some embodiments, the one or more other therapeutic agents are selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limiting to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limiting to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, and vidarabine; an immunotherapy, an antibody therapy, including, but not limiting to, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab and anti-CTLA-4 antibodies; a hormone or hormone antagonist, including, but not limiting to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limiting to, DJ-927, docetaxel, TPI 287, larotaxel, ortataxel, paclitaxel, DHA-paclitaxel, and tesetaxel; a retinoid, including, but not limiting to, alitretinoin, bexarotene, fenretinide, isotretinoin, and tretinoin; an alkaloid, including, but not limiting to, demecolcine, homoharringtonine, vinblastine, vincristine, vindesine, vinflunine, and vinorelbine; an anti-angiogenic agent, including, but not limiting to, AE-941 (GW786034, Neovastat), ABT-510, 2-methoxyestradiol, lenalidomide, and thalidomide; a topoisomerase inhibitor, including, but not limiting to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not liming to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), vemurafenib, dabrafenib, selumetinib, LGX818, BGB-283, PLX3397 and vatalanib; a targeted signal transduction inhibitor including, but not limiting to bortezomib, geldanamycin, and rapamycin; a biological response modifier, including, but not limiting to, imiquimod, interferon-α, and interleukin-2; and other chemotherapeutics, including, but not limiting to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. sirolimus, temsirolimus, everolimus, deforolimus), BCL-2 inhibitors (e.g., venetocalx), PI3K inhibitors (e.g. BEZ235, venetocalx, idelalisib, IDH1, IDH2, EZH2, GDC-0941, XL147, XL765), BTK inhibitor s (e.g., ibrutinib, alacabrutinib), Cdk4 inhibitors (e.g. PD-332991), Akt inhibitors, CTLA-4 inhibitors (ipilimumab), Hsp90 inhibitors (e.g. geldanamycin, radicicol, tanespimycin), checkpoint inhibitors (PD-1 inhibitors such as nivolumab, or PDL-1 inhibitors such as pembrolizumab), farnesyltransferase inhibitors (e.g. tipifarnib), and Aromatase inhibitors (anastrozole letrozole exemestane).

In some embodiments, the present disclosure provides a composition, e.g., a pharmaceutical composition comprising any one or more solid or amorphous forms of Compound I as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A) and one or more other therapeutic agents selected from an alkylating agent, including, but not limiting to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limiting to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limiting to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, and vidarabine; an immunotherapy, an antibody therapy, including, but not limiting to, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab and anti-CTLA-4 antibodies; a hormone or hormone antagonist, including, but not limiting to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limiting to, DJ-927, docetaxel, TPI 287, larotaxel, ortataxel, paclitaxel, DHA-paclitaxel, and tesetaxel; a retinoid, including, but not limiting to, alitretinoin, bexarotene, fenretinide, isotretinoin, and tretinoin; an alkaloid, including, but not limiting to, demecolcine, homoharringtonine, vinblastine, vincristine, vindesine, vinflunine, and vinorelbine; an antiangiogenic agent, including, but not limiting to, AE-941 (GW786034, Neovastat), ABT-510, 2-methoxyestradiol, lenalidomide, and thalidomide; a topoisomerase inhibitor, including, but not limiting to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not liming to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), vemurafenib, dabrafenib, selumetinib, paradox breakers (such as PLX8394 or PLX7904), LGX818, BGB-283, pexidartinib (PLX3397) and vatalanib; a targeted signal transduction inhibitor including, but not limiting to bortezomib, geldanamycin, and rapamycin; a biological response modifier, including, but not limiting to, imiquimod, interferon-α, and interleukin-2; and other chemotherapeutics, including, but not limiting to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. sirolimus, temsirolimus, everolimus, deforolimus, INK28, AZD8055, PI3K inhibitors (e.g. BEZ235, GDC-0941, XL147, XL765, BMK120), Cdk4 inhibitors (e.g. PD-332991), Akt inhibitors, Hsp90 inhibitors (e.g. geldanamycin, radicicol, tanespimycin), farnesyltransferase inhibitors (e.g. tipifarnib), and Aromatase inhibitors (anastrozole letrozole exemestane).

In some embodiments, the present disclosure provides a composition, e.g., a pharmaceutical composition comprising Compound I or a salt thereof, and one or more other therapeutic agents selected from an alkylating agent, including, but not limiting to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limiting to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limiting to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, and vidarabine; an immunotherapy, an antibody therapy, including, but not limiting to, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab and anti-CTLA-4 antibodies; a hormone or hormone antagonist, including, but not limiting to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limiting to, DJ-927, docetaxel, TPI 287, larotaxel, ortataxel, paclitaxel, DHA-paclitaxel, and tesetaxel; a retinoid, including, but not limiting to, alitretinoin, bexarotene, fenretinide, isotretinoin, and tretinoin; an alkaloid, including, but not limiting to, demecolcine, homoharringtonine, vinblastine, vincristine, vindesine, vinflunine, and vinorelbine; an anti-angiogenic agent, including, but not limiting to, AE-941 (GW786034, Neovastat), ABT-510, 2-methoxyestradiol, lenalidomide, and thalidomide; a topoisomerase inhibitor, including, but not limiting to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not liming to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), vemurafenib, dabrafenib, selumetinib, paradox breakers (such as PLX8394 or PLX7904), LGX818, BGB-283, pexidartinib (PLX3397) and vatalanib; a targeted signal transduction inhibitor including, but not limiting to bortezomib, geldanamycin, and rapamycin; a biological response modifier, including, but not limiting to, imiquimod, interferon-α, and interleukin-2; and other chemotherapeutics, including, but not limiting to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. sirolimus, temsirolimus, everolimus, deforolimus, INK28, AZD8055, PI3K inhibitors (e.g. BEZ235, GDC-0941, XL147, XL765, BMK120), Cdk4 inhibitors (e.g. PD-332991), Akt inhibitors, Hsp90 inhibitors (e.g. geldanamycin, radicicol, tanespimycin), farnesyltransferase inhibitors (e.g. tipifarnib), and Aromatase inhibitors (anastrozole letrozole exemestane).

In some embodiments, the present disclosure provides a composition, e.g., a pharmaceutical composition comprising any one or more solid or amorphous forms of Compound I as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A) and one or more other therapeutic agents selected from i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, panitumumab, pembrolizumab, pertuzumab, rituximab, tositumomab, trastuzumab, and 90 Y ibritumomab tiuxetan; v) a hormone or hormone antagonist selected from anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) an IDO inhibitor; and xv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor (anastrozole letrozole exemestane); xvi) a Mek inhibitor; xvii) a tyrosine kinase inhibitor; xviii) a c-Kit mutant inhibitor, xix) an EGFR inhibitor, or xx) an epigenetic modulator. In further embodiments, a bromodomain modulator, particularly a solid or amorphous form of Compound I as described herein (e.g., Compound I Form A, Compound I Form B, Compound I Form C, Compound I Form D, Compound I Material E, Compound I Material F, Compound I Free Acid Amorphous, a free acid amorphous salt form of Compound I, or the sodium salt of Compound I), may be administered simultaneously, sequentially or separately in combination with one or more agents as described above.

In some embodiments, the present disclosure provides a composition, e.g., a pharmaceutical composition comprising Compound I or a salt thereof, and one or more other therapeutic agents selected from i) an alkylating agent selected from adozelesin, altretamine, bizelesin, busulfan, carboplatin, carboquone, carmustine, chlorambucil, cisplatin, cyclophosphamide, dacarbazine, estramustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, panitumumab, pembrolizumab, pertuzumab, rituximab, tositumomab, trastuzumab, and 90 Y ibritumomab tiuxetan; v) a hormone or hormone antagonist selected from anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxycamptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) an IDO inhibitor; and xv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor (anastrozole letrozole exemestane); xvi) a Mek inhibitor; xvii) a tyrosine kinase inhibitor; xviii) a c-Kit mutant inhibitor, xix) an EGFR inhibitor, or xx) an epigenetic modulator. In further embodiments, a bromodomain modulator, particularly Compound I or a salt thereof, may be administered simultaneously, sequentially or separately in combination with one or more agents as described above.

Epigenetic modulators include DNA methylating agents and agents that modulate posttranslational modification of histones and/or proteins by the activity of chromatin modifiers. Non-limiting examples of Epigenetic modulators include:

(a) DNA methyltransferases (for example, azacytidine, decitabine or zebularine);

(b) histone and protein methyltransferases, including, but not limited to, DOT1L inhibitors such as EPZ004777 (7-[5-Deoxy-5-[[3-[[[[4-(1,1-dimethylethyl)phenyl]amino]carbonyl]amino]propyl](1-methylethyl)amino]-β-D-ribofuranosyl]-7H-pyrrolo[2,3-d]pyrimidin-4-amine), EZH1 inhibitors, EZH2 inhibitors or EPX5687;

(c) histone demethylases;

(d) histone deacetylase inhibitors (HDAC inhibitors) including, but not limited to, vorinostat, romidepsin, chidamide, panobinostat, belinostat, valproic acid, mocetinostat, abexinostat, entinostat, resminostat, givinostat, or quisinostat;

(e) histone acetyltransferase inhibitors (also referred to as HAT inhibitors) including, but not limited to, C-646, (4-[4-[[5-(4,5-Dimethyl-2-nitrophenyl)-2-furanyl]methylene]-4,5-dihydro-3-methyl-5-oxo-1H-pyrazol-1-yl]benzoic acida), CPTH2 (cyclopentylidene-[4-(4'-chlorophenyl)thiazol-2-yl]hydrazine), CTPB (N-(4-chloro-3-trifluoromethyl-phenyl)-2-ethoxy-6-pentadecyl-benzamide), garcinol ((1R,5R,7R)-3-(3,4-Dihydroxybenzyol)-4-hydroxy-8,8-dimethyl-1,7-bis(3-methyl-2-buten-1-yl)-5-[(2S)-5-methyl-2-(1-methylethenyl)-4-hexen-1-yl]bicyclo[3.3.1]non-3-ene-2,9-dione), anacardic acid, EML 425 (5-[(4-hydroxy-2,6-dimethylphenyl)methylene]-1,3-bis(phenylmethyl)-2,4,6 (1H,3H,5H)-pyrimidinetrione), ISOX DUAL ([3-[4-[2-[5-(Dimethyl-1,2-oxazol-4-yl)-1-[2-(morpholin-4-yl)ethyl]-1H-1,3-benzodiazol-2-yl]ethyl]phenoxy]propyl] dimethylamine), L002 (4-[O-[(4-methoxyphenyl)sulfonyl]oxime]-2,6-dimethyl-2,5-cyclohexadiene-1,4-dione), NU 9056 (5-(1,2-thiazol-5-yldisulfanyl)-1,2-thiazole), SI-2 hydrochloride (1-(2-pyridinyl)ethanone 2-(1-methyl-1H-benzimidazol-2-yl)hydrazone hydrochloride); or (f) other chromatin remodelers.

In some embodiments, the epigenetic modulator is vorinostat, romidepsin, belinostat, or panobinostat.

In some embodiments, compositions are provided that include a therapeutically effective amount of any one or more compound(s) as described herein (e.g., Compound I or a salt thereof, or any a solid or amorphous form of Compound I) and at least one pharmaceutically acceptable carrier, excipient, and/or diluent. In some embodiments, compositions are provided that include a therapeutically effective amount of any two or more compound(s) as described herein (e.g., Compound I or a salt thereof, or a solid or amorphous form of Compound I) and at least one pharmaceutically acceptable carrier, excipient, and/or diluent. In some embodiments, the compositions can further include a plurality of different pharmacologically active compounds, which can include a plurality of compounds as described herein. In some embodiments, the composition can include any one or more compound(s) as described herein along with one or more compounds that are therapeutically effective for the same disease indication. In some embodiments, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer. The compounds can be administered simultaneously or sequentially.

In some embodiments, the present disclosure provides a composition, e.g., a pharmaceutical composition comprising any one or more solid or amorphous forms of Compound I as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), in combination with a FMS inhibitor, such as quizartinib or pexidartinib. In some embodiments, the present disclosure provides a pharmaceutical composition comprising: any one or more solid or amorphous forms of Compound I as described herein; a pharmaceutically acceptable carrier; and quizartinib or pexidartinib.

In some embodiments, the present disclosure provides a composition, e.g., a pharmaceutical composition comprising a free acid amorphous form of Compound I as described herein, or a pharmaceutically acceptable salt thereof, in combination with a FMS inhibitor, such as quizartinib or pexidartinib. In some embodiments, the present disclosure provides a pharmaceutical composition comprising: a free acid amorphous form of Compound I as described herein, or a pharmaceutically acceptable salt thereof; a pharmaceutically acceptable carrier; and quizartinib or pexidartinib.

In some embodiments, the present disclosure provides a composition, e.g., a pharmaceutical composition comprising Compound I or a salt thereof, in combination with a FMS inhibitor, such as quizartinib or pexidartinib. In some embodiments, the present disclosure provides a pharmaceutical composition comprising: Compound I or a salt thereof; a pharmaceutically acceptable carrier; and quizartinib or pexidartinib.

In some embodiments, the present disclosure provides a composition, e.g., a pharmaceutical composition comprising any one or more of the solid or amorphous forms of Compound I as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), in combination with quizartinib. In some embodiments, the present disclosure provides a pharmaceutical composition comprising: any one or more of the solid or amorphous forms of Compound I as described herein; a pharmaceutically acceptable carrier; and quizartinib.

In some embodiments, the present disclosure provides a composition, e.g., a pharmaceutical composition comprising a free acid amorphous form of Compound I as described herein, or a pharmaceutically acceptable salt thereof, in combination with quizartinib. In some embodiments, the present disclosure provides a pharmaceutical composition comprising: a free acid amorphous form of Compound I as described herein, or a pharmaceutically acceptable salt thereof; a pharmaceutically acceptable carrier; and quizartinib.

In some embodiments, the present disclosure provides a composition, e.g., a pharmaceutical composition comprising Compound I or a salt thereof in combination with quizartinib. In some embodiments, the present disclosure provides a pharmaceutical composition comprising: Compound I or a salt thereof; a pharmaceutically acceptable carrier; and quizartinib.

In some embodiments, the present disclosure provides a composition, e.g., a pharmaceutical composition comprising any one or more solid or amorphous forms of Compound I as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), in combination with pexidartinib. In some embodiments, the present disclosure provides a pharmaceutical composition comprising: any one or more of the solid or amorphous forms of Compound I as described herein; a pharmaceutically acceptable carrier; and pexidartinib.

In some embodiments, the present disclosure provides a composition, e.g., a pharmaceutical composition comprising a free acid amorphous form of Compound I as described herein, or a pharmaceutically acceptable salt thereof, in combination with pexidartinib. In some embodiments, the present disclosure provides a pharmaceutical composition comprising: a free acid amorphous form of Compound I as described herein, or a pharmaceutically acceptable salt thereof; a pharmaceutically acceptable carrier; and pexidartinib.

In some embodiments, the present disclosure provides a composition, e.g., a pharmaceutical composition comprising Compound I or a salt thereof, in combination with pexidartinib. In some embodiments, the present disclosure provides a pharmaceutical composition comprising: Compound I or a salt thereof; a pharmaceutically acceptable carrier; and pexidartinib.

In some embodiments, the present disclosure provides a composition, e.g., a pharmaceutical composition comprising any one or more of the solid or amorphous forms of Compound I as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), in combination with a hypomethylating agent (HMA). In some embodiments, the present disclosure provides a pharmaceutical composition comprising: any one or more of the solid or amorphous forms of Compound I as described herein; a pharmaceutically acceptable carrier; and a hypomethylating agent (HMA).

In some embodiments, the present disclosure provides a composition, e.g., a pharmaceutical composition comprising a free acid amorphous form of Compound I as described herein, or a pharmaceutically acceptable salt thereof, in combination with a hypomethylating agent (HMA). In some embodiments, the present disclosure provides a pharmaceutical composition comprising: a free acid amorphous form of Compound I as described herein, or a pharmaceutically acceptable salt thereof; a pharmaceutically acceptable carrier; and a hypomethylating agent (HMA).

In some embodiments, the present disclosure provides a composition, e.g., a pharmaceutical composition comprising Compound I or a salt thereof, in combination with a hypomethylating agent (HMA). In some embodiments, the present disclosure provides a pharmaceutical composition comprising: Compound I or a salt thereof; a pharmaceutically acceptable carrier; and a hypomethylating agent (HMA).

In some embodiments, the present disclosure provides a composition, e.g., a pharmaceutical composition comprising any one or more solid or amorphous forms of Compound I as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), in combination with a Bruton's Tyrosine Kinase (BTK) inhibitor. In some embodiments, the present disclosure provides a pharmaceutical composition comprising: any one or more of the solid or amorphous forms of Compound I as described herein; a pharmaceutically acceptable carrier; and a Bruton's Tyrosine Kinase (BTK) inhibitor. In some embodiments, the BTK inhibitor is ibrutinib or alacabrutinib. In some embodiments, the BTK inhibitor is ibrutinib. In some embodiments, the BTK inhibitor is alacabrutinib.

In some embodiments, the present disclosure provides a composition, e.g., a pharmaceutical composition comprising a free acid amorphous form of Compound I as described herein, or a pharmaceutically acceptable salt thereof, in combination with a Bruton's Tyrosine Kinase (BTK) inhibitor. In some embodiments, the present disclosure provides a pharmaceutical composition comprising: a free acid amorphous form of Compound I as described herein, or a pharmaceutically acceptable salt thereof; a pharmaceutically acceptable carrier; and a Bruton's Tyrosine Kinase (BTK) inhibitor. In some embodiments, the BTK inhibitor is ibrutinib or alacabrutinib. In some embodiments, the BTK inhibitor is ibrutinib. In some embodiments, the BTK inhibitor is alacabrutinib.

In some embodiments, the present disclosure provides a composition, e.g., a pharmaceutical composition comprising Compound I or a salt thereof, in combination with a Bruton's Tyrosine Kinase (BTK) inhibitor. In some embodiments, the present disclosure provides a pharmaceutical composition comprising: Compound I or a salt thereof; a pharmaceutically acceptable carrier; and a Bruton's Tyrosine Kinase (BTK) inhibitor. In some embodiments, the BTK inhibitor is ibrutinib or alacabrutinib. In some embodiments, the BTK inhibitor is ibrutinib. In some embodiments, the BTK inhibitor is alacabrutinib.

In some embodiments, the present disclosure provides a composition, e.g., a pharmaceutical composition comprising any one or more solid or amorphous forms of Compound I as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), in combination with a B-cell lymphoma 2 (BCL-2) inhibitor. In some embodiments, the present disclosure provides a pharmaceutical composition comprising: any one or more of the solid or amorphous forms of Compound I as described herein; a pharmaceutically acceptable carrier; and a B-cell lymphoma 2 (BCL-2) inhibitor. In some embodiments, the BCL-2 inhibitor is venetoclax.

In some embodiments, the present disclosure provides a composition, e.g., a pharmaceutical composition comprising a free acid amorphous form of Compound I as described herein, or a pharmaceutically acceptable salt thereof in combination with a B-cell lymphoma 2 (BCL-2) inhibitor. In some embodiments, the present disclosure provides a pharmaceutical composition comprising: a free acid amorphous form of Compound I as described herein, or a pharmaceutically acceptable salt thereof; a pharmaceutically acceptable carrier; and a B-cell lymphoma 2 (BCL-2) inhibitor. In some embodiments, the BCL-2 inhibitor is venetocalx.

In some embodiments, the present disclosure provides a composition, e.g., a pharmaceutical composition comprising Compound I or a salt thereof, in combination with a B-cell lymphoma 2 (BCL-2) inhibitor. In some embodiments, the present disclosure provides a pharmaceutical composition comprising: a free acid amorphous form of Compound I as described herein, or pharmaceutically acceptable salt thereof; a pharmaceutically acceptable carrier; and a B-cell lymphoma 2 (BCL-2) inhibitor. In some embodiments, the BCL-2 inhibitor is venetocalx.

In some embodiments, the present disclosure provides a composition, e.g., a pharmaceutical composition comprising any one or more solid or amorphous forms of Compound I as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), in combination with a phosphatidylinositol-4,5-bisphosphate 3-kinase(PI3K) inhibitor. In some embodiments, the present disclosure provides a pharmaceutical composition comprising: any one or more of the solid or amorphous forms of Compound I as described herein; and a phosphatidylinositol-4,5-bisphosphate 3-kinase(PI3K) inhibitor. In some embodiments, the PI3K inhibitor is venetocalx, idelalisib, IDH1, IDH2 or EZH2.

In some embodiments, the present disclosure provides a composition, e.g., a pharmaceutical composition comprising a free acid amorphous form of Compound I as described herein, or a pharmaceutically acceptable salt thereof, in combination with a phosphatidylinositol-4,5-bisphosphate 3-kinase(PI3K) inhibitor. In some embodiments, the present disclosure provides a pharmaceutical composition comprising: a free acid amorphous form of Compound I as described herein, or a pharmaceutically acceptable salt thereof; a pharmaceutically acceptable carrier; and a phosphatidylinositol-4,5-bisphosphate 3-kinase(PI3K) inhibitor. In some embodiments, the PI3K inhibitor is venetocalx, idelalisib, IDH1, IDH2 or EZH2.

In some embodiments, the present disclosure provides a composition, e.g., a pharmaceutical composition comprising Compound I or a salt thereof, in combination with a phosphatidylinositol-4,5-bisphosphate 3-kinase(PI3K) inhibitor. In some embodiments, the present disclosure provides a pharmaceutical composition comprising: Compound I or a salt thereof; a pharmaceutically acceptable carrier; and a phosphatidylinositol-4,5-bisphosphate 3-kinase(PI3K) inhibitor. In some embodiments, the PI3K inhibitor is venetocalx, idelalisib, IDH1, IDH2 or EZH2.

In some embodiments, the present disclosure provides a composition, e.g., a pharmaceutical composition comprising any one or more solid or amorphous forms of Compound I as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), in combination with a CTLA-4 inhibitor or a checkpoint inhibitor. In some embodiments, the present disclosure provides a pharmaceutical composition comprising: any one or more of the solid or amorphous forms of Compound I as described herein; and a CTLA-4 inhibitor or a checkpoint inhibitor. In some embodiments, the CTLA-4 inhibitor is ipilimumab. In some embodiments, the checkpoint inhibitor is a PD-1 or PDL-1 inhibitor. In some embodiments, the PD-1 inhibitor is nivolumab. In some embodiments, the PDL-1 inhibitor is pembrolizumab.

In some embodiments, the present disclosure provides a composition, e.g., a pharmaceutical composition comprising a free acid amorphous form of Compound I as described herein, or a pharmaceutically acceptable salt thereof, in combination with a CTLA-4 inhibitor or a checkpoint inhibitor. In some embodiments, the present disclosure provides a pharmaceutical composition comprising: a free acid amorphous form of Compound I as described herein, or a pharmaceutically acceptable salt thereof; a pharmaceutically acceptable carrier; and a CTLA-4 inhibitor or a checkpoint inhibitor. In some embodiments, the CTLA-4 inhibitor is ipilimumab. In some embodiments, the checkpoint inhibitor is a PD-1 or PDL-1 inhibitor. In some embodiments, the PD-1 inhibitor is nivolumab. In some embodiments, the PDL-1 inhibitor is pembrolizumab.

In some embodiments, the present disclosure provides a composition, e.g., a pharmaceutical composition comprising Compound I or a salt thereof, in combination with a CTLA-4 inhibitor or a checkpoint inhibitor. In some embodiments, the present disclosure provides a pharmaceutical composition comprising: Compound I or a salt thereof; a pharmaceutically acceptable carrier; and a CTLA-4 inhibitor or a checkpoint inhibitor. In some embodiments, the CTLA-4 inhibitor is ipilimumab. In some embodiments, the PD-1 inhibitor is nivolumab. In some embodiments, the PDL-1 inhibitor is pembrolizumab.

In some embodiments, the present disclosure provides methods for treating a bromodomain mediated or mutant bromodomain mediated disease or condition in a subject in need thereof, the method comprising administering to the subject an effective amount of any one or more compounds as described herein (e.g., Compound I or a salt thereof, or any one or more solid or amorphous forms of Compound I), or a composition comprising any one or more compounds as described herein, in combination with one or more other therapeutic agents as described herein. In some embodiments, the bromodomain modulator, particularly a compound as described herein (e.g., Compound I or a salt thereof, or any one or more solid or amorphous forms of Compound I), may be administered simultaneously, sequentially or separately in combination with the one or more other therapeutic agents as described above.

In some embodiments, the present disclosure provides methods for treating a bromodomain mediated or mutant bromodomain mediated disease or condition in a subject in need thereof, the method comprising administering to the subject an effective amount of any one or more solid or amorphous forms of Compound I as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), or a composition comprising any one or more solid or amorphous forms of Compound I as described herein, in combination with one or more other therapeutic agents as described herein, wherein the disease or condition is a cancer, a neurological condition, an autoimmune condition, an inflammatory condition, a metabolic disease, or combinations thereof. In some embodiments, the bromodomain modulator, particularly a solid or amorphous form of Compound I as described herein, may be administered simultaneously, sequentially or separately in combination with the one or more other therapeutic agents as described above.

In some embodiments, the present disclosure provides methods for treating a bromodomain mediated or mutant bromodomain mediated disease or condition in a subject in need thereof, the method comprising administering to the subject an effective amount of Compound I or a salt thereof, or a composition comprising Compound I or a salt thereof, in combination with one or more other therapeutic agents as described herein, wherein the disease or condition is a cancer, a neurological condition, an autoimmune condition, an inflammatory condition, a metabolic disease, or combinations thereof. In some embodiments, the bromodomain modulator, particularly Compound I or a salt thereof, may be administered simultaneously, sequentially or separately in combination with the one or more other therapeutic agents as described above.

In some embodiments, the present disclosure provides methods for treating a bromodomain mediated or mutant bromodomain mediated disease or condition in a subject in need thereof, the method comprising administering to the subject an effective amount of any one or more solid or amorphous forms of Compound I as described herein (e.g., Compound I or a salt thereof, Compound I Form A, Compound I Form B, Compound I Form C, Compound I Form D, Compound I Material E, Compound I Material F, Compound I Material G, Compound I Free Acid Amorphous, a free acid amorphous salt form of Compound I, or Compound I sodium Material A), or a composition comprising any one or more solid or amorphous forms of Compound I as described herein, in combination with one or more other therapeutic agents as described herein, wherein the disease or condition is rheumatoid arthritis, uveal melanoma, chronic lymphocytic leukemia, acute myeloid leukemia, synovial sarcoma, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes, or acute rejection of transplanted organs. In some embodiments, the bromodomain modulator, particularly a compound as described herein (e.g., any one or more solid or amorphous forms of Compound I), may be administered simultaneously, sequentially or separately in combination with the one or more other therapeutic agents as described above.

In some embodiments, the present disclosure provides methods for treating a bromodomain mediated or mutant bromodomain mediated disease or condition in a subject in need thereof, the method comprising administering to the subject an effective amount of Compound I or a salt thereof, or a composition comprising Compound I or a salt thereof, in combination with one or more other therapeutic agents as described herein, wherein the disease or condition is rheumatoid arthritis, uveal melanoma, chronic lymphocytic leukemia, acute myeloid leukemia, synovial sarcoma, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes, or acute rejection of transplanted organs. In some embodiments, the bromodomain modulator, particularly a compound as described herein (e.g., any one or more solid or amorphous forms of Compound I), may be administered simultaneously, sequentially or separately in combination with the one or more other therapeutic agents as described above.

In one embodiment, the present disclosure provides methods for treating a cancer mediated by bromodomain or mutant bromodomain in a subject in need thereof by administering to the subject an effective amount of any one or more compounds as described herein (e.g., Compound I or a salt thereof, or any one or more solid or amorphous forms of Compound I), or a composition including any one or more compound(s) as described herein. In some embodiments, the bromodomain modulator, particularly a compound as described herein (e.g., Compound I or a salt thereof, or any one or more solid or amorphous forms of Compound I), may be administered simultaneously, sequentially or separately in combination with one or more agents as described above.

In one embodiment, the present disclosure provides methods for treating a cancer mediated by bromodomain in a subject in need thereof by administering to the subject an effective amount of any one or more compounds as described herein (e.g., Compound I or a salt thereof, or any one or more solid or amorphous forms of Compound I), or a composition comprising any one or more compound(s) as described herein, in combination with one or more suitable anticancer therapies, such as one or more chemotherapeutic drugs or agents as described herein.

In one embodiment, the present disclosure provides a method of treating a cancer in a subject in need thereof, comprising administering to the subject an effective amount of any one or more solid or amorphous forms of Compound I as described herein (e.g., Compound I Form A, Compound I Form B, Compound I Form C, Compound I Form D, Compound I Material E, Compound I Material F, Compound I Free Acid Amorphous, a free acid amorphous salt form of Compound I, or the sodium salt of Compound I), or a composition comprising any one or more solid or amorphous forms of Compound I as described herein, in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib. In one embodiment, the present disclosure provides a method of treating a cancer in a subject in need thereof, comprising administering to the subject an effective amount of Compound I or a salt thereof, or a composition comprising Compound I or a salt thereof, in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib. In some embodiments, the bromodomain modulator, particularly a compound as described herein (e.g., Compound I or a salt thereof, or any one or more solid or amorphous forms of Compound I), may be administered simultaneously, sequentially or separately in combination with one or more agents as described above.

In one embodiment, the chemotherapeutic agent is a Mek inhibitor. Exemplary Mek inhibitors include, but are not limited to, AS703026, AZD6244 (Selumetinib), AZD8330, BIX 02188, CI-1040 (PD184352), GSK1120212 (also known as trametinib or JTP-74057), cobimetinib, PD0325901, PD318088, PD98059, RDEA119(BAY 869766), TAK-733 and U0126-EtOH.

In one embodiment, the chemotherapeutic agent is a tyrosine kinase inhibitor. Exemplary tyrosine kinase inhibitors include, but are not limited to, AEE788, AG-1478 (Tyrphostin AG-1478), AG-490, Apatinib (YN968D1), AV-412, AV-951(Tivozanib), Axitinib, AZD8931, BIBF1120 (Vargatef), BIBW2992 (Afatinib), BMS794833, BMS-599626, Brivanib (BMS-540215), Brivanib alaninate (BMS-582664), Cediranib (AZD2171), Chrysophanic acid (Chrysophanol), Crenolanib (CP-868569), CUDC-101, CYC116, Dovitinib Dilactic acid (TKI258 Dilactic acid), E7080, Erlotinib Hydrochloride (Tarceva, CP-358774, OSI-774, NSC-718781), Foretinib (GSK1363089, XL880), Gefitinib (ZD-1839 or Iressa), Imatinib (Gleevec), Imatinib Mesylate, Ki8751, KRN 633, Lapatinib (Tykerb), Linifanib (ABT-869), Masitinib (Masivet, AB1010), MGCD-265, Motesanib (AMG-706), MP-470, Mubritinib(TAK 165), Neratinib (HKI-272), NVP-BHG712, OSI-420 (Desmethyl Erlotinib, CP-473420), OSI-930, Pazopanib HCl, PD-153035 HCl, PD173074, Pelitinib (EKB-569), PF299804, Ponatinib (AP24534), PP121, RAF265 (CHIR-265), Raf265 derivative, Regorafenib (BAY 73-4506), Sorafenib Tosylate (Nexavar), Sunitinib Malate (Sutent), Telatinib (BAY 57-9352), TSU-68 (SU6668), Vandetanib (Zactima), Vatalanib dihydrochloride (PTK787), WZ3146, WZ4002, WZ8040, quizartinib, Cabozantinib, XL647, EGFR siRNA, FLT4 siRNA, KDR siRNA, Antidiabetic agents such as metformin, PPAR agonists (rosiglitazone, pioglitazone, bezafibrate, ciprofibrate, clofibrate, gemfibrozil, fenofibrate, indeglitazar), and DPP4 inhibitors (sitagliptin, vildagliptin, saxagliptin, dutogliptin, gemigliptin, alogliptin).

In one embodiment, the agent is an EGFR inhibitor. Exemplary EGFR inhibitors include, but are not limited to, AEE-788, AP-26113, BIBW-2992 (Tovok), CI-1033, GW-572016, Iressa, LY2874455, RO-5323441, Tarceva (Erlotinib, OSI-774), CUDC-101 and WZ4002.

In one embodiment, the therapeutic agent for combination is a c-Fms and/or c-Kit inhibitor as described in US Patent Application Publication Nos. 2009/0076046 and 2011/0112127, which are incorporated herein by reference in their entirety and for all purposes.

In one embodiment, the present disclosure provides methods for treating a disease or condition mediated by a bromodomain or mutant bromodomain protein in a subject in need thereof, by administering to the subject an effective amount of any one or more solid or amorphous forms of Compound I as described herein (e.g., Compound I Form A, Compound I Form B, Compound I Form C, Compound I Form D, Compound I Material E, Compound I Material F, Compound I Free Acid Amorphous, a free acid amorphous salt form of Compound I, or the sodium salt of Compound I), in combination with quizartinib for treating the disease or condition.

In one embodiment, the present disclosure provides methods for treating a disease or condition mediated by a bromodomain or mutant bromodomain protein in a subject in need thereof, by administering to the subject an effective amount of Compound I or a salt thereof, in combination with quizartinib for treating the disease or condition.

In some embodiments, the disclosure provides a method of treating a subject suffering from a disease or condition described in this disclosure, said method comprising administering to the subject an effective amount of any one or more solid or amorphous forms of Compound I as described herein (e.g., Compound I Form A, Compound I Form B, Compound I Form C, Compound I Form D, Compound I Material E, Compound I Material F, Compound I Free Acid Amorphous, a free acid amorphous salt form of Compound I, or the sodium salt of Compound I), in combination with a mutant c-Kit protein kinase inhibitor. In some embodiments, the disclosure provides a method of treating a subject suffering from a disease or condition described in this disclosure, said method comprising administering to the subject an effective amount of Compound I or a salat thereof, in combination with a mutant c-Kit protein kinase inhibitor. In some embodiments, the mutant c-Kit protein kinase inhibitor is selected from (2-phenyl-1H-pyrrolo[2,3-b]pyridin-5-yl)-(3-pyridyl)methanol, (2-phenyl-1H-pyrrolo[2,3-b]pyridin-5-yl)-(3-pyridyl)methanone, N-(3-carbamoylphenyl)-2-phenyl-1H-pyrrolo[2,3-b]pyridine-5-carboxamide, 2-phenyl-N-(1H-pyrazol-3-yl)-1H-pyrrolo[2,3-b]pyridine-5-carboxamide, 4-bromo-N-(2-phenyl-1H- pyrrolo[2,3-b]pyridin-5-yl)-1H-pyrazole-5-carboxamide, ethyl 3-[(2-phenyl-1H-pyrrolo[2,3-b]pyridin-5-yl)carbamoylamino]propanoate, 3,4-dimethyl-N-(2-phenyl-1H-pyrrolo[2,3-b]pyridin-5-yl)-1H-pyrazole-5-carboxamide, 4-methyl-3-phenyl-N-(2-phenyl-1H-pyrrolo[2,3-b]pyridin-5-yl)-1H-pyrazole-5-carboxamide, 3-cyclopropyl-N-(2-phenyl-1H-pyrrolo[2,3-b]pyridin-5-yl)-1H-pyrazole-5-carboxamide, 5-fluoro-N-(2-phenyl-1H-pyrrolo[2,3-b]pyridin-5-yl)-1H-indazole-3-carboxamide, N-(2-phenyl-1H-pyrrolo[2,3-b]pyridin-5-yl)pyrimidine-4-carboxamide, 3-fluoro-N-(2-phenyl-1H-pyrrolo[2,3-b]pyridin-5-yl)pyridine-2-carboxamide, 3,5-dimethyl-N-(2-phenyl-1H-pyrrolo[2,3-b]pyridin-5-yl)isoxazole-4-carboxamide, N-(2-phenyl-1H-pyrrolo[2,3-b]pyridin-5-yl)pyridazine-3-carboxamide, N-(2-phenyl-1H-pyrrolo[2,3-b]pyridin-5-yl)-2H-triazole-4-carboxamide, 3-methyl-N-(2-phenyl-1H-pyrrolo[2,3-b]pyridin-5-yl)pyridine-2-carboxamide, 4,5-dimethyl-N-(2-phenyl-1H-pyrrolo[2,3-b]pyridin-5-yl)isoxazole-3-carboxamide or N-(2-phenyl-1H-pyrrolo[2,3-b]pyridin-5-yl)-1H-pyrazole-4-sulfonamide. In some embodiments, a compound as described herein is combined with any of the mutant c-Kit mutant inhibitiors described in this specification for treating GIST—which includes, without limitation, $1^{st}$ line, $2^{nd}$ line and neoadjuvant GIST.

In some embodiments, the present disclosure provides methods for treating a subject suffering or at risk of a disease or condition mediated by a bromodomain, said method comprising administering to the subject in need thereof an effective amount of any one or more solid or amorphous forms of Compound I as described herein (e.g., Compound I Form A, Compound I Form B, Compound I Form C, Compound I Form D, Compound I Material E, Compound I Material F, Compound I Free Acid Amorphous, a free acid amorphous salt form of Compound I, or the sodium salt of Compound I), and a pharmaceutical acceptable excipient or carrier, in combination with quizartinib.

In some embodiments, the present disclosure provides methods for treating a subject suffering or at risk of a disease or condition mediated by a bromodomain, said method comprising administering to the subject in need thereof an effective amount of a free acid amorphous form of Compound I as described herein, or a pharmaceutically acceptable salt thereof, and a pharmaceutical acceptable excipient or carrier, in combination with quizartinib.

In some embodiments, the present disclosure provides methods for treating a subject suffering or at risk of a disease or condition mediated by a bromodomain, said method comprising administering to the subject in need thereof an effective amount of Compound I or a salt thereof, and a pharmaceutical acceptable excipient or carrier, in combination with quizartinib.

In some embodiments, the present disclosure provides methods for treating a subject suffering or at risk of a disease or condition mediated by a bromodomain, said method comprising administering to the subject in need thereof an effective amount of a pharmaceutical composition comprising: any of one or more solid or amorphous forms of Compound I as described herein (e.g., Compound I Form A, Compound I Form B, Compound I Form C, Compound I Form D, Compound I Material E, Compound I Material F, Compound I Free Acid Amorphous, a free acid amorphous salt form of Compound I, or the sodium salt of Compound I); at least one pharmaceutically acceptable excipient or carrier; and quizartinib.

In some embodiments, the present disclosure provides methods for treating a subject suffering or at risk of a disease or condition mediated by a bromodomain, said method comprising administering to the subject in need thereof a composition comprising: an effective amount of a free acid amorphous form of Compound I as described herein, or a pharmaceutically acceptable salt thereof; at least one pharmaceutically acceptable excipient or carrier; and quizartinib.

In some embodiments, the present disclosure provides methods for treating a subject suffering or at risk of a disease or condition mediated by a bromodomain, said method comprising administering to the subject in need thereof a composition comprising: an effective amount of Compound I or a salt thereof; at least one pharmaceutically acceptable excipient or carrier; and quizartinib In some embodiments, the present disclosure provides a method of treating myelodysplastic syndromes (MDS) or acute myeloid leukemia (AML) in a subject in need thereof by administering to the subject an effective amount of a free acid amorphous form of Compound I as described herein, or a pharmaceutically acceptable salt thereof, in combination with an effective amount of a hypomethylating agent (HMA).

In some embodiments, the present disclosure provides a method of treating myelodysplastic syndromes (MDS) or acute myeloid leukemia (AML) in a subject in need thereof by administering to the subject an effective amount of any one or more solid or amorphous forms of Compound I as described herein (e.g., Compound I Form A, Compound I Form B, Compound I Form C, Compound I Form D, Compound I Material E, Compound I Material F, Compound I Free Acid Amorphous, a free acid amorphous salt form of Compound I, or the sodium salt of Compound I), in combination with an effective amount of a hypomethylating agent (HMA).

In some embodiments, the present disclosure provides a method of treating myelodysplastic syndromes (MDS) or acute myeloid leukemia (AML) in a subject in need thereof by administering to the subject an effective amount of Compound I or a salt thereof, in combination with an effective amount of a hypomethylating agent (HMA).

In some embodiments, the present disclosure provides a method of treating chronic lymphocytic leukemia (CLL) or Richter's Syndrome in a subject in need thereof by administering to the subject an effective amount of a free acid amorphous form of Compound I as described herein, or a pharmaceutically acceptable salt thereof, optionally in combination with an effective amount of a Bruton's Tyrosine Kinase (BTK) inhibitor. In some embodiments, the BTK inhibitor is ibrutinib or alacabrutinib. In some embodiments, the BTK inhibitor is ibrutinib. In some embodiments, the BTK inhibitor is alacabrutinib.

In some embodiments, the present disclosure provides a method of treating chronic lymphocytic leukemia (CLL) or Richter's Syndrome in a subject in need thereof by administering to the subject an effective amount of any one or more solid or amorphous forms of Compound I as described herein (Compound I Form A, Compound I, Form B, Compound I Form C, Compound I Form D, Compound I Material E, Compound I Material F, Compound I Free Acid Amorphous, or the sodium salt of Compound I), optionally in combination with an effective amount of a Bruton's Tyrosine Kinase (BTK) inhibitor. In some embodiments, the BTK inhibitor is ibrutinib or alacabrutinib. In some embodiments, the BTK inhibitor is ibrutinib. In some embodiments, the BTK inhibitor is alacabrutinib.

In some embodiments, the present disclosure provides a method of treating chronic lymphocytic leukemia (CLL) or Richter's Syndrome in a subject in need thereof by administering to the subject an effective amount of Compound I or a salt thereof, in combination with an effective amount of a Bruton's Tyrosine Kinase (BTK) inhibitor. In some embodiments, the BTK inhibitor is ibrutinib or alacabrutinib. In some embodiments, the BTK inhibitor is ibrutinib. In some embodiments, the BTK inhibitor is alacabrutinib.

In some embodiments, the present disclosure provides a method of treating chronic lymphocytic leukemia (CLL) in a subject in need thereof by administering to the subject an effective amount of a free acid amorphous form of Compound I as described herein, or a pharmaceutically acceptable salt thereof, in combination with an effective amount of a B-cell lymphoma 2 (BCL-2) inhibitor. In some embodiments, the BCL-2 inhibitor is venetocalx.

In some embodiments, the present disclosure provides a method of treating chronic lymphocytic leukemia (CLL) in a subject in need thereof by administering to the subject an effective amount of any one or more solid or amorphous forms of Compound I as described herein (Compound I Form A, Compound I, Form B, Compound I Form C, Compound I Form D, Compound I Material E, Compound I Material F, Compound I Free Acid Amorphous, or the sodium salt of Compound I), in combination with an effective amount of a (BCL-2) inhibitor. In some embodiments, the BCL-2 inhibitor is venetocalx.

In some embodiments, the present disclosure provides a method of treating chronic lymphocytic leukemia (CLL) in a subject in need thereof by administering to the subject an effective amount of Compound I or a salt thereof, in combination with an effective amount of a B-cell lymphoma 2 (BCL-2) inhibitor. In some embodiments, the BCL-2 inhibitor is venetocalx.

In some embodiments, the present disclosure provides a method of treating chronic lymphocytic leukemia (CLL) in a subject in need thereof by administering to the subject an effective amount of a free acid amorphous form of Compound I as described herein, or a pharmaceutically acceptable salt thereof, in combination with an effective amount of a phosphatidylinositol-4,5-bisphosphate 3-kinase(PI3K) inhibitor. In some embodiments, the PI3K inhibitor is venetocalx, idelalisib, IDH1, IDH2 or EZH2.

In some embodiments, the present disclosure provides a method of treating chronic lymphocytic leukemia (CLL) in a subject in need thereof by administering to the subject an effective amount of any one or more solid or amorphous forms of Compound I as described herein (Compound I Form A, Compound I, Form B, Compound I Form C, Compound I Form D, Compound I Material E, Compound I Material F, Compound I Free Acid Amorphous, or the sodium salt of Compound I), in combination with an effective amount of a (PI3K) inhibitor. In some embodiments, the PI3K inhibitor is venetocalx, idelalisib, IDH1, IDH2 or EZH2.

In some embodiments, the present disclosure provides a method of treating chronic lymphocytic leukemia (CLL) in a subject in need thereof by administering to the subject an effective amount of Compound I or a salt thereof, in combination with an effective amount of a phosphatidylinositol-4,5-bisphosphate 3-kinase(PI3K) inhibitor. In some embodiments, the PI3K inhibitor is venetocalx, idelalisib, IDH1, IDH2 or EZH2.

In some embodiments, the present disclosure provides a method of treating uveal melanoma in a subject in need thereof by administering to the subject an effective amount of a free acid amorphous form of Compound I as described herein, or a pharmaceutically acceptable salt thereof, in combination with an effective amount of a CTLA-4 inhibitor or a checkpoint inhibitor. In some embodiments, the CTLA-4 inhibitor is ipilimumab. In some embodiments, the checkpoint inhibitor is a PD-1 or PDL-1 inhibitor. In some embodiments, the PD-1 inhibitor is nivolumab. In some embodiments, the PDL-1 inhibitor is pembrolizumab.

In some embodiments, the present disclosure provides a method of treating uveal melanoma in a subject in need thereof by administering to the subject an effective amount of any one or more solid or amorphous forms of Compound I as described herein (e.g., Compound I Form A, Compound I Form B, Compound I Form C, Compound I Form D, Compound I Material E, Compound I Material F, Compound I Free Acid Amorphous, a free acid amorphous salt form of Compound I, or the sodium salt of Compound I), in combination with an effective amount of a CTLA-4 inhibitor or a checkpoint inhibitor. In some embodiments, the CTLA-4 inhibitor is ipilimumab. In some embodiments, the checkpoint inhibitor is a PD-1 or PDL-1 inhibitor. In some embodiments, the PD-1 inhibitor is nivolumab. In some embodiments, the PDL-1 inhibitor is pembrolizumab.

In some embodiments, the present disclosure provides a method of treating uveal melanoma in a subject in need thereof by administering to the subject an effective amount of a Compound I or a salt thereof, in combination with an effective amount of a CTLA-4 inhibitor or a checkpoint inhibitor. In some embodiments, the CTLA-4 inhibitor is ipilimumab. In some embodiments, the checkpoint inhibitor is a PD-1 or PDL-1 inhibitor. In some embodiments, the PD-1 inhibitor is nivolumab. In some embodiments, the PDL-1 inhibitor is pembrolizumab.

In some embodiments, the present disclosure provides a method of treating acute myeloid leukemia (AML) in a subject in need thereof by administering to the subject an effective amount of a free acid amorphous form of Compound I as described herein, or a pharmaceutically acceptable salt thereof, in combination with an effective amount of a flt3 inhibitor, such as quizartinib.

In some embodiments, the present disclosure provides a method of treating AML in a subject in need thereof by administering to the subject an effective amount of any one or more solid or amorphous forms of Compound I as described herein (e.g., Compound I Form A, Compound I Form B, Compound I Form C, Compound I Form D, Compound I Material E, Compound I Material F, Compound I Free Acid Amorphous, a free acid amorphous salt form of Compound I, or the sodium salt of Compound I), in combination with an effective amount of a flt3 inhibitor, such as quizartinib.

In some embodiments, the present disclosure provides a method of treating acute myeloid leukemia (AML) in a subject in need thereof by administering to the subject an effective amount of Compound I or a salt thereof, in combination with an effective amount of a flt3 inhibitor, such as quizartinib.

In some embodiments, the present disclosure provides methods for treating a bromodomain or mutant bromodomain mediated disease or condition in a subject in need thereof, the method comprising administering to the subject any one or more compounds as described herein (e.g., Compound I or a salt thereof, or any one or more solid or amorphous forms of Compound I), or a composition comprising any one or more compounds as described herein, in combination with one or more other suitable therapies for treating the disease or condition. In some embodiments, the bromodomain modulator, particularly a compound as described herein (e.g., Compound I or a salt thereof, or any one or more solid or amorphous forms of Compound I), may be administered simultaneously, sequentially or separately in combination with one or more the one or more other suitable therapies.

In one embodiment, the present disclosure provides methods for treating a cancer mediated by bromodomain or mutant bromodomain by administering to the subject an effective amount of a composition including any one or more compound(s) as described herein. In one embodiment, the present disclosure provides methods for treating a cancer mediated by bromodomain by administering to the subject an effective amount of a composition including any one or more compound(s) as described herein in combination with one or more suitable anticancer therapies, such as one or more chemotherapeutic drugs or agents as described herein.

In some embodiments, the present disclosure provides a method of treating a cancer as described herein in a subject in need thereof by administering to the subject an effective amount of any one or more solid or amorphous forms of Compound I as described herein (Compound I Form A, Compound I Form B, Compound I Form C, Compound I Form D, Compound I Material E, Compound I Material F, Compound I Free Acid Amorphous, a free acid amorphous salt form of Compound I, or the sodium salt of Compound I), or a composition including any one or more solid or amorphous forms of Compound I as described herein, in combination with one or more other therapies or medical procedures effective in treating the cancer. In some embodiments, the present disclosure provides a method of treating a cancer as described herein in a subject in need thereof by administering to the subject an effective amount of Compound I or a salt thereof, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or a particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-C SF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), oncolytic viral or bacterial therapy, surgery, or bone marrow and stem cell transplantation. In some embodiments, the present disclosure provides a method of treating a cancer in a subject in need thereof by administering to the subject an effective amount of a compound as described herein and applying a radiation treatment as described herein either separately or simultaneously.

In one embodiment, the present disclosure provides a method for treating a cancer in a subject in need thereof by administering an effective amount of any one or more solid or amorphous forms of Compound I as described herein (e.g., Compound I Form A, Compound I Form B, Compound I Form C, Compound I Form D, Compound I Material E, Compound I Material F, Compound I Free Acid Amorphous, a free acid amorphous salt form of Compound I, or the sodium salt of Compound I) to the subject followed by a radiation treatment (e.g. x-ray, γ-ray, or electron, proton, neutron, or α particle beam). In one embodiment, the present disclosure provides a method for treating a cancer in a subject in need thereof by administering an effective amount of Compound I or a salt thereof to the subject followed by a radiation treatment (e.g. x-ray, γ-ray, or electron, proton, neutron, or α particle beam).

In some embodiments, the present disclosure provides a method for treating a cancer in a subject in need thereof by applying a radiation treatment (e.g. x-ray, γ-ray, or electron, proton, neutron, or α particle beam) to the subject followed by administering an effective amount of a compound as described herein to the subject. In yet another embodiment, the present disclosure provides a method for treating a cancer in a subject in need thereof by administering a compound as described herein and a radiation therapy (e.g. x-ray, γ-ray, or electron, proton, neutron, or α particle beam) to the subject simultaneously.

In some embodiments, the present disclosure provides kits or containers that include a compound as described herein (e.g., Compound I or a salt thereof, or any one or more solid or amorphous forms of Compound I), or a composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a bromodomain protein mediated disease or condition; the kit or container disclosed herein may include written instructions for use and/or other indication that the compound or composition is suitable or approved for administration to a mammal, e.g., a human, for a bromodomain-mediated disease or condition; and the compound or composition may be packaged in unit dose or single dose form, e.g., single dose pills, capsules, or the like.

EXAMPLES

A. Experimental Methods

Solubility Estimates

Aliquots of various solvents were added to measured amounts of Compound I or forms of Compound I as described herein with agitation (typically sonication) at ambient temperature until complete dissolution was achieved, as judged by visual observation. Solubilities were calculated based on the total solvent used to give a solution; actual solubilities may be greater because of the volume of solvent portions utilized or a slow rate of dissolution. If dissolution did not occur as determined by visual assessment, the value was reported as "<". If dissolution occurred at the first aliquot the value was reported as ">".

Anti-Solvent Additions

Solutions comprising Compound I or forms of Compound I as described herein were contacted with anti-solvents of Compound I to induce crystallization.

Cooling

Solutions comprising Compound I or forms of Compound I as described herein were chilled below room temperature for varying lengths of time to induce nucleation, after which the presence of absence of solids was noted. Solids were isolated for analysis wet or as dry powders.

Crystallization From Solution

Saturated solutions comprising Compound I or forms of Compound I as described herein were generated at room temperature and capped. Nucleation was observed to occur in such systems.

Fast Evaporation

Solutions comprising Compound I or forms of Compound I as described herein were prepared in selected solvents and agitated between aliquot additions to assist in dissolution. Once a mixture reached complete dissolution, as judged by visual observation, the solution was allowed to evaporate at ambient temperature in an uncapped vial or under nitrogen. The solids that formed were isolated for evaluation.

Slurry

Solutions of Compound I or forms of Compound I as described herein were prepared by adding sufficient solids to a given solvent or solvent system at ambient conditions such that undissolved solids were present. The mixture was then agitated in a closed vial at ambient or elevated temperature for an extended period of time. Solids were collected by vacuum filtration and analyzed.

Temperature and Relative Humidity (RH) Stress

Solids of Compound I or forms of Compound I as described herein were placed in an RH chamber of approximately 75% RH containing a saturated aqueous solution of a NaCl with excess salt present. The chamber was sealed and left at ambient temperature or placed in an oven at elevated temperature.

Vacuum

Selected materials were dried under reduced pressure for a set time period. Drying was conducted with absolute pressure readings <500 mTorr, typically 30 to 50 mTorr (0.030 to 0.05 mm Hg).

B. Instrumental Techniques

Differential Scanning calorimetry (DSC)

DSC was performed using a TA Instruments Q2000 differential scanning calorimeter. Temperature calibration was performed using NIST-traceable indium metal. The sample was placed into an aluminum DSC pan, covered with a lid, and the weight was accurately recorded. A weighed aluminum pan configured as the sample pan was placed on the reference side of the cell. The data acquisition parameters and pan configuration for each thermogram are displayed in the image in the Data section of this report. The method code on the thermogram is an abbreviation for the start and end temperature as well as the heating rate; e.g., −30-250-10 means "from −30° C. to 250° C., at 10° C./min." The abbreviation used in each image for pan configurations, TOC means "Tzero crimped pan."

Dynamic Vapor Solution

DVS data were collected on a VTI SGA-100 Vapor Sorption Analyzer. NaCl and PVP were used as calibration standards. Samples were not dried prior to analysis. Adsorption and desorption data were collected over a range from 5 to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

Proton Solution Nuclear Magnetic Resonance Spectroscopy ($^1$H NMR)

Samples were prepared for NMR spectroscopy as ~5-50 mg solutions in deuterated DMSO. The specific acquisition parameters are listed on the plot of the first full spectrum of each sample in the data section for samples run at SSCI. The chemical shift observed at approximately 2.5 ppm is assigned to residual protons in the NMR solvent (DMSO-d6) and the chemical shift observed at approximately 3.3 ppm is due to water.

Thermogravimetric Analysis (TGA)

TG analyses were performed using a TA Instruments 2050 thermogravimetric analyzer. Temperature calibration was performed using nickel and Alumel™. Each sample was placed in an aluminum pan and inserted into the TG furnace. The furnace was heated under a nitrogen purge. The data acquisition parameters are displayed above each thermogram in the Data section of this report. The method code on the thermogram is an abbreviation for the start and end temperature as well as the heating rate; e.g., 25-350-10 means "from 25° C. to 350° C., at 10° C./min." The use of 00 as the initial temperature indicates sample run initiated from ambient.

X-Ray Powder Diffraction (XRPD)

(i) Inel: XRPD patterns were collected with an Inel XRG-3000 diffractometer. An incident beam of Cu Kα radiation was produced using a fine-focus tube and a parabolically graded multilayer mirror. Prior to the analysis, a silicon standard (NIST SRM 640d) was analyzed to verify the Si 111 peak position. A specimen of the sample was packed into a thin-walled glass capillary, and a beam-stop was used to minimize the background from air. Diffraction patterns were collected in transmission geometry using Windif v. 6.6 software and a curved position-sensitive Equinox detector with a 2θ range of 120°. The data-acquisition parameters for each pattern are displayed above the image in the Data section of this report.

(ii) PANalytical: XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the Si 111 peak position. A specimen of the sample was sandwiched between 3 μm thick films and analyzed in transmission geometry. A beam-stop, short antiscatter extension, and an antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data-acquisition parameters for each pattern are displayed above the image in the Data section of this report including the divergence slit (DS) before the mirror and the incident-beam antiscatter slit (SS).

Supercritical Fluid Chromatography

Supercritical fluid chromatography (SFC) was used to purify certain compounds disclosed herein. Purification via SFC employed the following materials and conditions:

| Analytical SFC Method | |
|---|---|
| Column | 4.6 × 100 mm (S, S) Whelk0-1 from Regis Technologies (Morton Grove, IL) |
| CO$_2$ co-solvent | Methanol w/ 0.1% isopropylamine |
| Isocratic method | 45% co-solvent at 4 mL/min |
| System pressure | 100 bar |
| Column temperature | 25° C. |
| Sample diluent | Ethanol |
| Preparative SFC method | |
| Column | 2.1 × 25 cm (S, S) Whelk0-1 from Regis Technologies (Morton Grove, IL) |

-continued

| | |
|---|---|
| CO₂ co-solvent | Methanol w/ 0.5% isopropylamine |
| Isocratic method | 45% co-solvent at 80 g/min |
| System pressure | 100 bar |
| Column temperature | 40° C. |
| Sample diluent | Methanol/methylene chloride (1:1) with 1% isopropylamine |

C. Preparation and Characterization of Solid Forms of Compound I

Several solid form screening experiments were conducted using Compound I Form A or Compound I Form D as the starting material. Compound I Form A and Form D were prepared according to the following scheme.

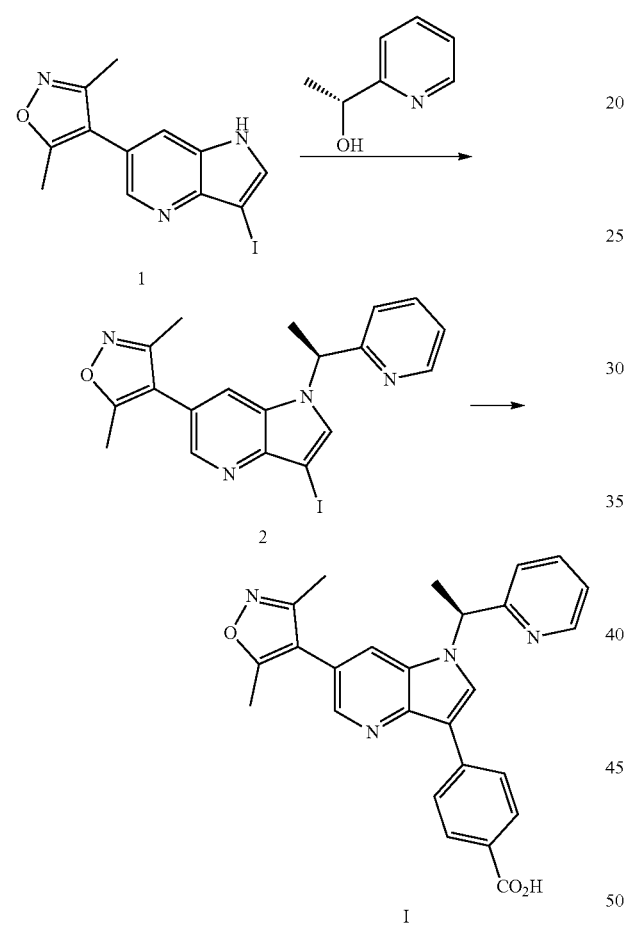

4-(3-iodo-1H-pyrrolo[3,2-b]pyridin-6-yl)-3,5-dimethyl-isoxazole (1) was synthesized as described in WO 2017/053243. To (1) was added triphenylphosphate (TPP) and diisopropyl azodicarboxylate (DIAD) under Mitsunobu reaction conditions to form (S)-4-(3-iodo-1-(1-(pyridin-2-yl)ethyl)-1H-pyrrolo[3,2-b]pyridin-6-yl)-3,5-dimethylisoxazole (2). To (2) was added 2,6-difluorophenylboronic acid, (Pd(dppf)Cl₂, and HCl under Suzuki coupling reaction conditions to obtain Compound I Form A. Compound I Form A was purified via supercritical fluid chromatography (SFC) to obtain Compound I Form D.

All forms discussed below in Table 1 were obtained starting from Compound I Form A using a wide range of solvents and solvent mixtures under kinetic and thermodynamic conditions.

TABLE 1

Solid Form Screening Experiments Using Compound I Form A

| Solvent | Method | Observation | XRPD Results |
|---|---|---|---|
| Acetone | Precipitated from solution | Irregular blades, and fine particles, birefringent | Form B |
| | Precipitated from solution, and refrigerated | Fine blades, birefringent, and sheets | Not analyzed based on above |
| | Dissolved; treated with ether; fast evaporation seeded with a sample of a form B + C; rinsed solids into vial and sonicated; resulting solids filtered and dried in vacuum oven | Fine particles | Form B + Form C |
| ACN | Precipitated from solution | Solids | Form B + Form C |
| | Sonicated for about 5 minutes; left at ambient conditions overnight; solids harvested and dried in vacuum oven | Fine particles, very small rectangular blades, birefringent | Form B + Form C |
| ACN/acetone (filtrates from a sample of a form B and a sample of a form B + C) | Treated with activated charcoal; N₂ evaporated; scratched | Fine particles and rosettes of Fine particles, birefringent, oil present and nucleated | Form C + Form B (minor) |
| ACN/acetone (filtrates from samples of a form B + C) | Filtrates added together, left overnight and filtered | Fine particles, birefringent | Form C |
| DCM | Contacted with solvent then sonicated; filtered; and evaporated | Solids, glassy film, small tablets, birefringent | Form B |
| | Added solvent (59 mg/mL); treated with water and DCM; organic layer isolated and dried, MgSO₄; treated with activated carbon; evaporated, N₂; small amount DCM/sonicated and evaporated | Fine particles, birefringent | Form B |
| DCM/ether 1: 1 v/v | 7 mg/ml suspension in 1:1 ether/DCM; treated with MgSO₄ and filtered; stored at ambient conditions | Aciculars and blades, birefringent | Form B |
| MeOH | Dissolved; treated with activated charcoal; evaporation (partial); evaporation to dryness | Dendritic and plates, singles | Form B + Form C |
| | Isolated single crystals | In solution and dry | Form B (racemate) |
| | Rapid addition of solvent, sonicated; filtered and rinsed in MeOH; vacuum dried | Fine particles, birefringent | Form B + Form C |
| | Sonicated in filtrate from a sample of a form B + C; filtered, wet cake | Solids | Form B + Form C |

TABLE 1-continued

Solid Form Screening Experiments Using Compound I Form A

| Solvent | Method | Observation | XRPD Results |
|---|---|---|---|
| | isolated; wet cake treated with MeOH, filtered, rinsed with MeOH and vacuum dried | | |
| Toluene | Slurry, ambient | Solids with some aggregated portions being less soluble | Form A |

All forms discussed below in Table 2 were obtained starting from Compound I Form D using a wide range of solvents and solvent mixtures under kinetic and thermodynamic conditions.

TABLE 2

Solid Form Screening Experiments Using Compound I Form D

| Solvent | Method | Observation | XRPD Results |
|---|---|---|---|
| Acetone | Fast evaporation | Fine aciculars, birefringent | Form D |
| ACN | Slurry, ambient | Capillary preparation | Form D (shifted) |
| Chloroform | Evaporation heated, 2x; oil contacted with heptane | Solids, glassy, NB | Amorphous |
| | Solution, seeded with sample of a form C overnight; drop of water added; left overnight | Seeds remained | — |
| | Sample with above seeds added; heated, 50° C.; filtered, cooled; seeded with sample of a form C; treated with heptane and sonicated; ambient, 3 days filtered, dried under N₂ | Fine particles, no birefringence | Form D (shifted) |
| DCM | Fast evaporation | Fine particles, birefringent | Form D (shifted peaks) |
| Diethyl ether | Slurry, ambient | Capillary preparation | Form D (shifted) |
| Dioxane | Fast evaporation | Film no birefringence, areas with nucleated fines | Form C |
| EtOH | Fast evaporation (partial) | Single crystals, off white film tablets, chunks birefringent | Form C + Form D |
| EtOAc | Slurry, ambient | Capillary preparation | Form D (shifted) |
| | Slurry, ambient using sample of amorphous form | Fine particles, birefringent | Form D (shifted) |
| IPA | Fast evaporation | Fine particles and tablets, birefringent | Form D (shifted) + Form C |
| MEOH | Fast evaporation | Cracked glass and film, few plates, birefringent | Form D (shifted peaks) |
| THF | Fast evaporation | Sheets of fine aciculars in upper vial, lower brittle glassy material | Amorphous |
| Toluene | Slurry, ambient | Capillary preparation | Form D (shifted) |
| Water | Fast evaporation | Aciculars and dendritic, birefringent | Form C + Material E |
| | Saturated solution; seeded with sample of a form C and sonicated; seeded with Sample of Material E + Form C and sonicated; ambient storage overnight and filtered; dried briefly, N₂ | Blades, birefringent, some singles present | Material F + Form C (minor) |

— No results observed/obtained

D. Solubility Estimates

Compound I Form A

Solubility estimates of Compound I Form A in various solvents are provided in Table 3 below. It is of note that an impurity observed in some of the samples of Compound I Form A, as well as the presence of precipitation of Compound I Form B may have affected the solubility estimates.

TABLE 3

Solubility Estimates of Compound I Form A

| Solvent | Solubility (mg/ml) |
|---|---|
| Acetone | 36 |
| Acetonitrile (ACN) | 6 |
| Dichloromethane (DCM) | 12 |
| Methanol (MeOH) | 6 |
| Toluene | <4 |

Compound I Form D

Solubility estimates of Compound I Form D in various solvents are provided in Table 4 below. It is of note that such solubility estimates may have been influenced due to the solvated nature of Compound I Form D.

TABLE 4

Solubility Estimates of Compound I Form D

| Solvent | Solubility (mg/ml) |
|---|---|
| acetone | 4 |
| acetonitrile (ACN) | <3 |
| chloroform | >59 |
| dichloromethane (DCM) | 24 |
| diethyl ether | <2 |

TABLE 4-continued

Solubility Estimates of Compound I Form D

| Solvent | Solubility (mg/ml) |
|---|---|
| dioxane | <2 |
| ethanol (EtOH) | 9 |
| ethyl acetate (EtOAc) | <2 |
| isopropyl alcohol (IPA) | 4 |
| methanol (MeOH) | >72 |
| tetrahydrofuran (THF) | 4 |
| toluene | <2 |
| water | 23 |

E. Preparation and Characterization of Compound I Sodium Material A

The formation of sodium salts of Compound I discussed below in Table 5 below were obtained starting from Compound I Form A using various solvents and solvent mixtures under kinetic and thermodynamic conditions.

TABLE 5

Sodium Salt Screening From Compound I Form A

| Source | Method | Observation | Results |
|---|---|---|---|
| Compound I Form A | 53 mg/mL suspension in DCM, filtered; treated with charcoal; molar eq. of NaOH in MeOH added; DCM added; sub sample indicated material exhibiting B after evaporation seeded bulk solution; placed in freezer overnight; $N_2$ evaporated; ether added, formed slurry and left overnight | Solids, NB | Diffuse scattering with some Sodium Material A peaks |
| Compound I Form A | 121 mg/ml suspension in MeOH, sonicated about 5 minutes; filtered, dried under $N_2$ with heat; molar eq. of NaOH in MeOH added to solids; treated with EtOAc; sub sample evaporated; seeded bulk with sub sample, partial evaporation; freezer overnight, filtered | Powder, free flowing | Compound I Sodium Material A |
| Filtrate from Sample of Compound I Form A | Reduced volume using water aspirator by about ¼ capillary sub sample bulk collected and dried under $N_2$ | Fine aciculars, birefringent  White solids | Diffuse scattering with limited reflections  Compound I Sodium Material A |
| Filtrate from Sample of Compound I sodium Material A | Reduced volume using water aspirator by about ¼ and stored in freezer; reduced volume under $N_2$ to increase yield; sonicated, left for about 1 hr at ambient, isolated sub sample on slide, bulk stored in freeze; sub sample isolated and evaporated; decanted | Wet paste | Compound I Sodium diffuse scattering + peaks, wet |
| Compound I sodium Material A | Filtered and $N_2$ dried | White opaque solids, birefringent in areas | Compound I Sodium Material A |
| Sample of a form B + Form C | 8 mg/ml suspension in acetone, slurry; molar eq. of NaOH in water added, slurry and sonication; reduced volume under $N_2$ to about ¼ of initial; left at ambient, capped; filtered | Solids collapsed, oil/gel present | Compound I Sodium similar to Material A, disordered |
|  | Solution of sample of Compound I sodium similar to Material A (disordered) added to ether; evaporated under $N_2$ | Solids, not, powder like | Generation of seed material |
|  | Solution of sample of Compound I sodium similar to Material A (disordered) wet | — | Diffuse scattering + peaks |

TABLE 5-continued

Sodium Salt Screening From Compound I Form A

| Source | Method | Observation | Results |
|---|---|---|---|
| | 18 mg/ml suspension in MeOH, slurry; molar eq. of NaOH in MeOH added; reduced volume under $N_2$ to about ½ of initial; treated with ether; stored in freezer; and evaporated | Glassy, not birefringent | Compound I Sodium Amorphous |
| | Sub sample of Compound I sodium amorphous added to ether | Flocculent and fines, birefringent | generation of seed material |

— No results observed/obtained

F. Compound I Free Acid Amorphous

Figure 24A:
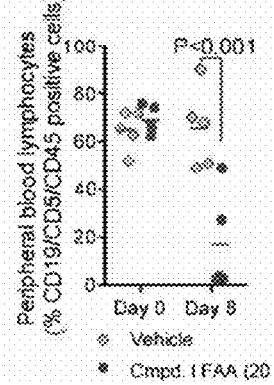
FIG. 24 panels A-H provide graphical representations demonstrating the potent anti-leukemic effects of targeting BRD4 with the free acid amorphous form of Compound I (Compound I Free Acid Amorphous, "Cmpd. I FAA") in disease models of aggressive chronic lymphocytic leukemia (CLL) and Richter's Transformation.
FIG. 24C is a representative immunoblot analysis of relative protein levels of cMYC, P21, BTK, IKZF1, IKZF3 and TCL1A protein at the end of the 8 day study.
FIG. 24D is a Kaplan-Meier curve showing overall survival (OS) (p<0.0001), with the median OS for Compound I Free Acid Amorphous and the vehicle being 93 days and 34 days, respectively. Survival comparisons for FIG. 24D were made with the log-rank test, and p-values were adjusted for multiple comparisons. Compound I Free Acid Amorphous decreased the percentage of circulating leukemic PBL (FIG. 24E), and reduced spleen mass (FIG. 24F).
FIG. 24G shows the HE and Ki67 staining of spleen, lung and blood from Compound I Free Acid Amorphous treated mice, where said mice are depleted of lymphocytes, and Ki67 staining is mostly absent.
FIG. 24H is a Kaplan-Meier curve showing overall survival for C57BL/6 mice engrafted with Eµ-TCL1 leukemic splenocytes treated with Ibrutinib or Compound I Free Acid Amorphous (20 mg/kg, qd, oral gavage) at leukemia onset, where the median OS is: 41 days (Compound I Free Acid Amorphous, n=7), 32 days (Ibrutinib, n=8) and 21 days (vehicle, n=7). Compound I Free Acid Amorphous significantly increased survival compared with vehicle (p=0.024) and Ibrutinib (p=0.049). Survival comparisons for FIG. 24H were made with the log-rank test, and p-values were adjusted for multiple comparisons.
Figure 24B:
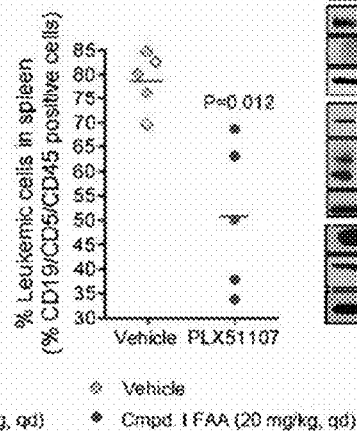
Figure 24C:
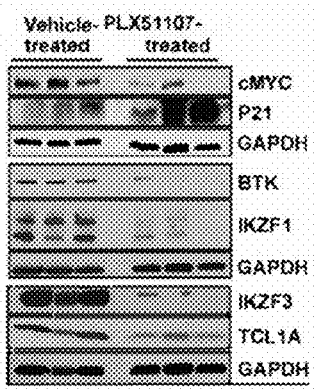

Targeting BRD4 with Compound I Free Acid Amorphous ("Cmpd. I FAA") shows potent anti-leukemic effects in disease models of aggressive CLL and Richter's Transformation. FIGS. 24-24C show the results of a pharmacodynamic evaluation of antitumor effects of Compound I Free Acid Amorphous in Eµ-TCL1 with advanced leukemia. Mice were stratified according to leukemic peripheral blood lymphocytes (PBLs) and spleen palpation score to receive either vehicle or Compound I Free Acid Amorphous (20 mg/kg, qd, oral gavage) for 8 days. Compound I Free Acid Amorphous reduced leukemic cells in systemic circulation (FIG. 24A) and locally in spleen (FIG. 24B), where the red line in FIGS. 24A-24B represents average values. FIG. 24C is a representative immunoblot analysis of relative protein levels of cMYC, P21, BTK, IKZF1, IKZF3 and TCL1A protein at the end of the 8 day study.

Figure 24D:
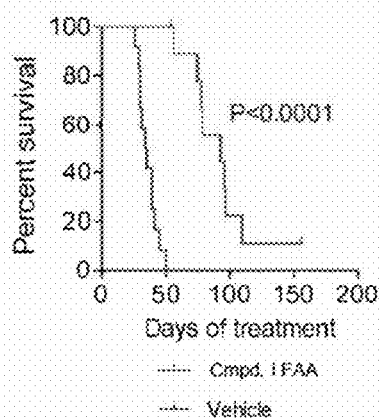
Figure 24E:
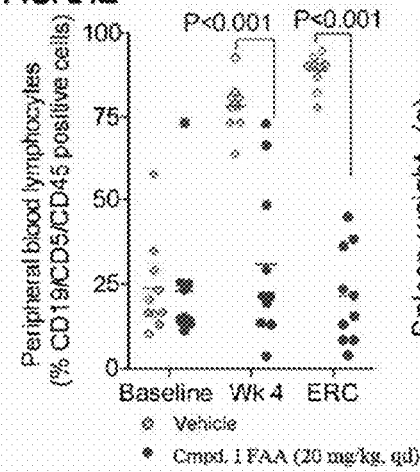
Figure 24F:
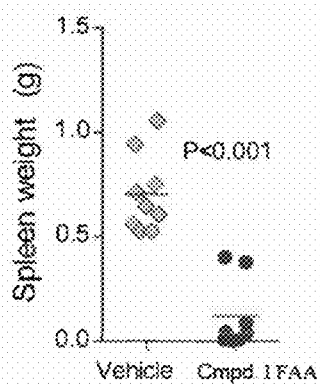
Figure 24G:
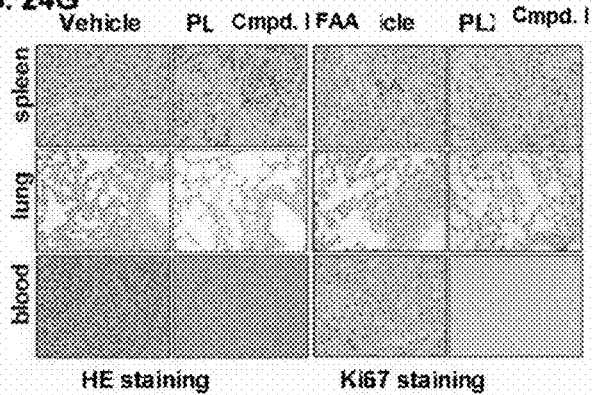

Using an adaptive transfer model of Eµ-TCL1, recipient wild type mice were randomized to receive vehicle (n=12) or Compound I Free Acid Amorphous (20 mg/kg, qd, oral gavage, n=10) at leukemia onset and disease progression was measured by flow cytometry as % CD19/CD5/CD45 positive PBL. Treatment was ended at 150 days. FIG. 24D is a Kaplan-Meier curve showing overall survival (OS) (p<0.0001), with the median OS for Compound I Free Acid Amorphous and the vehicle being 93 days and 34 days, respectively. Survival comparisons for FIG. 24D were made with the log-rank test, and p-values were adjusted for multiple comparisons. Compound I Free Acid Amorphous decreased the percentage of circulating leukemic PBL (FIG. 24E), and reduced spleen mass (FIG. 24F). FIG. 24G shows the HE and Ki67 staining of spleen, lung and blood from Compound I Free Acid Amorphous treated mice, where said mice are depleted of lymphocytes, and Ki67 staining is mostly absent.

G. Comparative Data

Compound I Free Acid vs. Ibrutinib

Figure 24H:
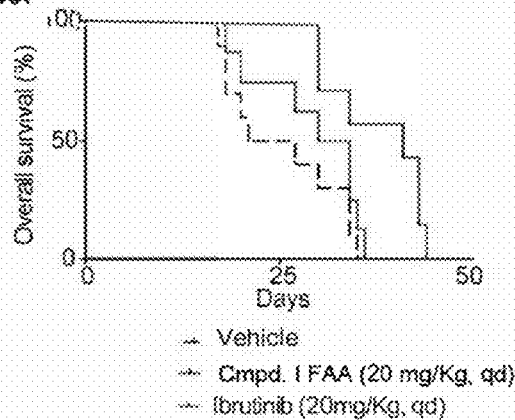

FIG. 24H is a Kaplan-Meier curve showing overall survival (OS) for C57BL/6 mice engrafted with Eµ-TCL1 leukemic splenocytes treated with Ibrutinib or Compound I Free Acid Amorphous (Cmpd. I FAA) (20 mg/kg, qd, oral gavage) at leukemia onset. Survival comparisons for FIG. 24H were made with the log-rank test, and p-values were adjusted for multiple comparisons.

Ibrutinib is currently the standard of care (first-in-line) treatment. Surprisingly, the median OS was 41 days for Compound I Free Acid Amorphous compared to 32 days for ibrutinib and 21 days for the vehicle. Compound I Free Acid Amorphous significantly increased survival compared with vehicle (p=0.024) and Ibrutinib (p=0.049).

All patents and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

What is claimed is:

1. A free acid amorphous form of Compound I:

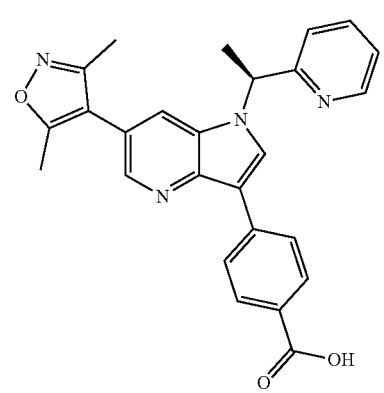

I characterized by an X-ray powder diffractogram as substantially shown in FIG. 18.

2. A free acid amorphous form of Compound I according to claim 1 characterized by a thermogravimetric analysis (TGA) thermogram showing a weight loss of about 17% up to about 250° C.

3. A free acid amorphous form of Compound I according to claim 1 characterized by a TGA thermogram as substantially shown in FIG. 19.

4. A free acid amorphous form of Compound I according to claim 1 characterized by a differential scanning calorimetry (DSC) curve that comprises an exotherm with a peak maximum at about 237° C.

5. A free acid amorphous form of Compound I according to claim 1 characterized by a DSC curve as substantially shown in FIG. 20.

6. A free acid amorphous form of Compound I according to claim 1 molecularly dispersed in a polymer matrix.

7. A free acid amorphous form of Compound I according claim 6, wherein the polymer matrix comprises hypromellose acetate succinate, hydroxypropyl methylcellulose phthalate, polymethylacrylate-based copolymers, or combinations thereof.

8. A pharmaceutical composition comprising one or more pharmaceutically acceptable carriers, and the free acid amorphous form of Compound I according to claim 1.

9. A method of treating chronic lymphocytic leukemia (CLL) or Richter's Syndrome in a subject in need thereof comprising administering to the subject an effective amount of the free acid amorphous form of Compound I according to claim 1, in combination with an effective amount of a Bruton's Tyrosine Kinase (BTK) inhibitor.

10. The method of claim 9, wherein the BTK inhibitor is ibrutinib.

11. A method of treating chronic lymphocytic leukemia (CLL) in a subject in need thereof comprising administering to the subject an effective amount of the free acid amorphous form of Compound I according to claim 1, in combination with an effective amount of a B-cell lymphoma 2 (BCL-2) inhibitor.

12. A method of treating uveal melanoma in a subject in need thereof comprising administering to the subject an effective amount of the free acid amorphous form of Compound I according to claim 1, in combination with an effective amount of a CTLA-4 inhibitor or a checkpoint inhibitor.

13. A method of treating acute myeloid leukemia in a subject in need thereof comprising administering to the subject an effective amount of the free acid amorphous form of Compound I according to claim 1, in combination with an effective amount of quizartinib.

14. The method of claim 11, wherein the BCL-2 inhibitor is venetoclax.

15. A method of treating acute myeloid leukemia in a subject in need thereof comprising administering to the subject an effective amount of the free acid amorphous form of Compound I according to claim 1, in combination with an effective amount of azacitidine.

16. A method of treating myelodysplastic syndromes (MDS) in a subject in need thereof comprising administering to the subject an effective amount of the free acid amorphous form of Compound I according to claim 1, in combination with an effective amount of azacitidine.

17. A method of treating ovarian cancer in a subject in need thereof comprising administering to the subject in need thereof an effective amount of the free acid amorphous form of Compound I according to claim 1.

18. A method of treating acute myeloid leukemia (AML) in a subject in need thereof comprising administering to the subject an effective amount of the free acid amorphous form of Compound I according to claim 1, in combination with an effective amount of a B-cell lymphoma 2 (BCL-2) inhibitor.

19. The method of claim 18, wherein the BCL-2 inhibitor is venetoclax.

* * * * *